United States Patent
Tyan et al.

(10) Patent No.: US 10,338,080 B2
(45) Date of Patent: Jul. 2, 2019

(54) METHODS AND COMPOSITIONS FOR DETECTION OF COMPLEMENT FIXING ANTIBODIES

(75) Inventors: Dolly B. Tyan, Palomar Park, CA (US); Ge Chen, Los Angeles, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 372 days.

(21) Appl. No.: 13/129,554

(22) PCT Filed: Nov. 25, 2009

(86) PCT No.: PCT/US2009/065984
§ 371 (c)(1),
(2), (4) Date: Aug. 3, 2011

(87) PCT Pub. No.: WO2010/065425
PCT Pub. Date: Jun. 10, 2010

(65) Prior Publication Data
US 2011/0281757 A1 Nov. 17, 2011

Related U.S. Application Data

(60) Provisional application No. 61/118,949, filed on Dec. 1, 2008.

(51) Int. Cl.
| | |
|---|---|
| *C40B 30/04* | (2006.01) |
| *C40B 40/10* | (2006.01) |
| *G01N 33/554* | (2006.01) |
| *G01N 33/82* | (2006.01) |
| *G01N 21/75* | (2006.01) |
| *G01N 33/68* | (2006.01) |
| *G01N 33/543* | (2006.01) |

(52) U.S. Cl.
CPC ....... *G01N 33/6854* (2013.01); *G01N 33/543* (2013.01); *G01N 2333/4716* (2013.01)

(58) Field of Classification Search
None
See application file for complete search history.

(56) References Cited

U.S. PATENT DOCUMENTS

| | | | |
|---|---|---|---|
| 4,708,871 A | 11/1987 | Geysen | |
| 5,035,995 A * | 7/1991 | Taguchi et al. | 435/4 |
| 5,223,397 A | 6/1993 | Pouletty | |
| 5,270,169 A * | 12/1993 | Chang | G01N 33/564 435/7.21 |
| 5,851,829 A | 12/1998 | Marasco et al. | |
| 5,965,371 A | 10/1999 | Marasco et al. | |
| 6,146,589 A | 11/2000 | Chandler | |
| 6,150,122 A * | 11/2000 | Lee | G01N 33/54313 435/7.1 |
| 6,159,748 A * | 12/2000 | Hechinger | C12Q 1/6816 435/5 |
| 6,514,714 B1 | 2/2003 | Lee et al. | |
| 7,332,349 B2 | 2/2008 | Yang et al. | |
| 8,828,664 B2 | 9/2014 | Fekete et al. | |
| 2005/0059095 A1 | 3/2005 | Yang et al. | |
| 2005/0277158 A1 * | 12/2005 | Chen | G01N 33/564 435/7.2 |
| 2005/0282172 A1 * | 12/2005 | Liu | 435/6 |
| 2007/0042414 A1 | 2/2007 | Hutchens et al. | |
| 2007/0042505 A1 | 2/2007 | Israel et al. | |
| 2012/0065092 A1 | 3/2012 | Wai et al. | |
| 2012/0070834 A1 | 3/2012 | Greinacher et al. | |
| 2016/0033524 A1 | 2/2016 | Tyan et al. | |
| 2016/0041185 A1 | 2/2016 | Tyan et al. | |

FOREIGN PATENT DOCUMENTS

| | | |
|---|---|---|
| CN | 1423130 | 6/2003 |
| CN | 1444044 | 9/2003 |
| CN | 1766616 | 5/2006 |
| EP | 0204522 | 12/1986 |
| JP | 61245060 | 10/1986 |
| JP | 63109371 | 5/1988 |
| JP | 1-501571 A | 6/1989 |
| JP | 2001521909 | 11/2001 |
| JP | 2008100986 | 5/2008 |
| JP | 2009080019 A | 4/2009 |

(Continued)

OTHER PUBLICATIONS

Wahrmann et al. J Immunological Methods 275 (2003)149-160.*

(Continued)

*Primary Examiner* — Tracy Vivlemore
*Assistant Examiner* — Sahana S Kaup
(74) *Attorney, Agent, or Firm* — Edward J. Baba; Shweta Chandra; Bozicevic, Field & Francis LLP

(57) ABSTRACT

The invention provides methods for sensitive and specific detection of complement fixing antibodies in a biological sample using complement factor C1q, including autologous complement factor C1q present in the biological sample and a detectably labeled antibody that binds the autologous complement factor C1q, exogenous human complement factor C1q and a detectably labeled antibody that binds the exogenous human complement factor C1q, detectably labeled exogenous human complement factor C1q, or a combination of autologous complement factor C1q and exogenous human complement factor C1q. The invention also features kits, systems, and devices for use in the methods of the invention.

18 Claims, 46 Drawing Sheets

(56) References Cited

FOREIGN PATENT DOCUMENTS

| WO | 2008035047 | 3/2008 |
|---|---|---|
| WO | 2010138456 | 12/2010 |
| WO | 2013029181 | 3/2013 |

OTHER PUBLICATIONS

Pei et al. Human Immunology 59, 313-322 (1998).*
Wahrmann et al. (Human Immunology 66, 526-534 (2005)).*
Suankratay et al. (Clin Exp Immunol. Sep. 1999;117(3):442-8).*
Steinberger et al. (Journal of Leukocyte Biology 71.1 (2002): 133-140).*
Schønau, Andreas, Henrik Stender, and Per Chr Grauballe. "A one-step solid phase immunoassay for simultaneous detection of serum IgG and IgM antibodies to Borrelia burgdorferi." Journal of immunological methods 218.1-2 (1998): 9-17. (Year: 1998).*
Anjaneyulu & Staros (1987) "Reactions of N-Hydroxysulfosuccinimide Active Esters" Int. J. Pept. Protein Res. 30(1):117-124.
Brinkley (1992) "A Brief Survey of Methods for Preparing Protein Conjugates with Dyes, Haptens, and Cross-Linking Reagents" Bioconjug. Chem. 3(1):2-13.
Geysen et al. (1986) "A priori Delineation of a Peptide Which Mimics a Discontinuous Antigenic Determinant" Mol. Immunol. 23(7):709-715.
Geysen et al. (1984) "Use of Peptide Synthesis to Probe Viral Antigens for Epitopes to a Resolution of a Single Amino Acid" Proc. Natl. Acad. Sci. USA 81(13):3998-4002.
Hashida et al. (1984) "More Useful Maleimide Compounds for the Conjugation of Fab' to Horseradish Peroxidase through Thiol Groups in the Hinge" J. Appl. Biochem. 6(1-2):56-63.
International Search Report for PCT Application No. PCT/US2009/065984, dated Mar. 30, 2010.
Kishore et al. (2004) "C1q and Tumor Necrosis Factor Superfamily: Modularity and Versatility" Trends Immunol. 25(10):551-561.
Smith et al. (1994) "β-Sheet Secondary Structure of the Trimeric Globular Domain of C1q of Complement and Collagen Types VIII and X by Fourier-Transform Infrared Spectroscopy and Averaged Structure Predictions" Biochem. J. 301(Pt 1):249-256.
Smith et al. (2007) "C4d Fixing, Luminex Binding Antibodies—A New Tool for Prediction of Graft Failure after Heart Transplantation" Am. J. Transplant. 7(12):2809-2815.
Wahrmann et al. (2003) "Flow Cytometry Based Detection of HLA Alloantibody Mediated Classical Complement Activation" J. Immunol. Methods. 275(1-2):149-160.
Chen et al. (2011) "Novel C1q assay reveals a clinically relevant subset of human Leukocyte antigen antibodies independent of immunoglobulin G strength on single antigen beads" Hum. Immunol. 72(10):849-858.
Wahrmann et al. (2005) "[C4d]FlowPRA Screening—A Specific Assay for Selective Detection of Competent-Activating Anti-HLA Alloantibodies" Hum. Immunol. 66(5):526-534.
Billen et al. (2008) "Luminex donor-specific crossmatches" Tissue antigens 71(6):507-513.
Chen et al. (2013) "C1q Assay for the Detection of Complement Fixing Antibody to HLA Antigens" Methods in Molecular Biology 1034:305-311.
Elshal & McCoy (2006) "Multiplex Bead Array Assays: Performance Evaluation and Comparison of Sensitivity to ELISA" Methods, 38(4):317-323.
Kishore et al., (1997) "Release of calreticulin from neutrophils may alter C1q-mediated immune functions" Biochem J 322(pt 2):543-550.
Kishore et al., (2003) "Modular Organization of the Carboxyl-Terminal, Globular Head Region of Human C1q A, B, and C Chains" Journal of Immunology, 171(2):812-820.
Yabu et al., (2011) "C1q-fixing human leukocyte antigen antibodies are specific for predicting transplant glomerulopathy and late graft failure after kidney transplant" Transplantation, 91(3):342-347.

* cited by examiner

COMPARISON OF ONE- AND TWO-STEP LUMINEX-C1q

Observed/Expected

| SERUM | HLA-Abs Called ||
|---|---|---|
| | Two-Step | One-Step |
| Positive | 47/50 | 50/50 |
| B8,59 | 0/2 | 2/2 |

FIG 7

SUMMARY OF CDC/LUMINEX-C1q IVIG INHIBITION ASSAY

| No. | SAMPLE | CDC Pre-IVIG Prediction | CDC Post-IVIG | CDC In vitro/in vivo Correlation | Luminex-C1q Pre-IVIG Prediction | Luminex-C1q Post-IVIG | Luminex-C1q In vitro/in vivo Correlation |
|---|---|---|---|---|---|---|---|
| 1 | | Unclear | Inhibition | ? | Inhibition | Inhibition | Yes |
| 2 | | Negative | N/A | N/A | C-II Inhibition | C-II Inhibition | Yes |
| 3 | | w/ Rituxin C-II unclear | C-I Inhibition | Yes | Inhibition | Inhibition | Yes |
| 4 | | Unclear | C-I Inhibition | N/A | Inhibition | Inhibition | Yes |
| 5 | | Negative | N/A | N/A | Negative | N/A | Yes |
| 6 | | D. Inhibition | D. Inhibition | Yes | D. Inhibition | D. Inhibition | Yes |
| 7 | | Negative | N/A | N/A | Inhibition | Inhibition | Yes |
| 8 | | * C-I Negative C-II Inhibition | C-II Inhibition? | Yes | Inhibition | Inhibition | Yes |
| 9 | | IgM-Abs | N/A | N/A | Inhibition | Inhibition | Yes |
| 10 | | Undefined IgM-Abs | Negative | N/A | No Inhibition | No Inhibition | Yes |
| 11 | | Non-Specific Reactivity | N/A | N/A | Negative | Negative | Yes |
| 12 | | C-I Negative C-II Weak Rx. | N/A | N/A | Inhibition | Inhibition | Yes |
| 13 | | N/A | N/A | N/A | Inhibition | Inhibition | Yes |
| 14 | | M. Inhibition | Inhibition | Yes | No Inhibition | No Inhibition | Yes |

*Differential Inhibition

FIG 10

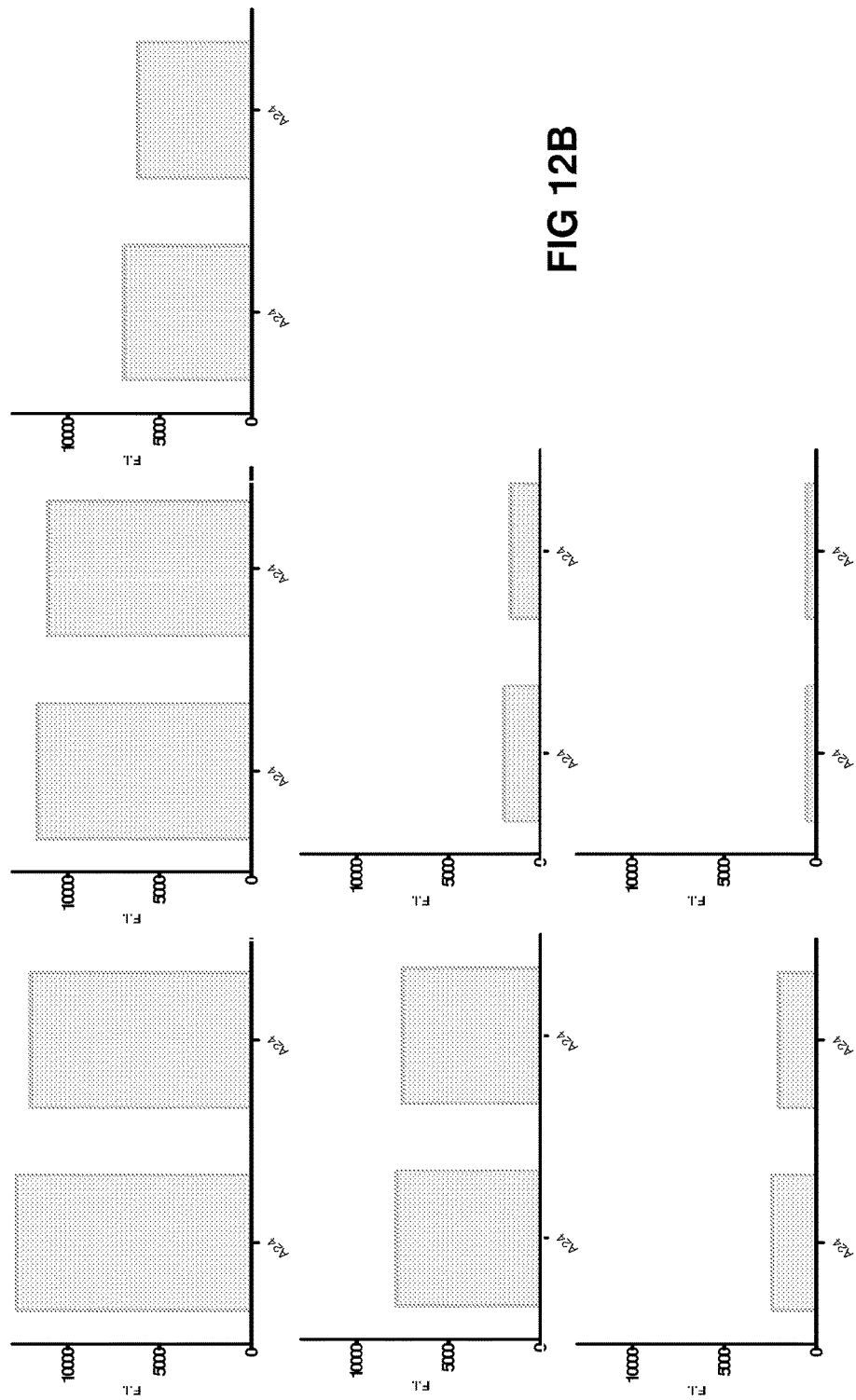

Luminex-C1Q Validation Experiment Results

| PATIENT No. | PRA-CDC | PRA-IgG | CDC | LUMINEX-C1q NEAT | LUMINEX-C1q 1:2 | LUMINEX-IgG |
|---|---|---|---|---|---|---|
| 1 | | CI-20<br>CII-45 | NEG. | DQ7 | same | B53,63,51,52,78,49,54<br>DR51,16 DQ4,7. |
| 2 | CI-91 | CI-89<br>CII-89 | A1,9,10,11,32<br>BW4<br>RPT- BROAD | A24,32,23,25,11,66<br>BW4, B76,45,82<br>DR4,53. DQ7,8,9,DP | same | A1,9,10,11,32,80<br>BW4,12,4005,56,76,82<br>BROAD |
| 3 | CI-29<br>CII-0 | CI-54<br>CII-0 | B7,27,42,54 (Test date?)<br>RPT- negative 10/25/07 | NEGATIVE | same | B7,27,22,42,51,54,55,<br>56,67,73,75,78,81,82.<br>A24,CW1,14. |
| 4 | CI-49<br>CII-81 | CI-68<br>CII-96 | A2<br>DR1,4,8,13,DQ7,8,9. | A2, wk68<br>DR1,4,wk11,DQ7 | same<br>DR11, | A2,68,69,B15,18,57,62,63<br>75,76,77.<br>DR1,0103,2,4,8,9,10,11,12<br>13,14,15,16,51,DQ4,5,6,7,<br>8,9. |
| 5 | CI-0<br>CII-0 | CI-58<br>CII-7 | CI-NEGATIVE<br>KILLED ALL B CELLS | NEGATIVE | same | B12,13,21,37,40,41,42,<br>44,45,47,48,49,50,52,60<br>61,62,72,75,76,77,DQ8. |
| 6 | | CI-67<br>CII-59 | UNCLEAR SPECS. | B57,58<br>DQ7,8,9. | same | A1,2,36. B57,58<br>DQ7,8,9. |
| 7 | CI-49<br>CII-20 | CI-55<br>CII-39 | A2, DR7<br>RPT- NEGATIVE | NEGATIVE | same | A2,B57,58.<br>DR1,7,9,10. |
| 8 | CI-62 | CI-71<br>CII-14 | B5,12,15,17,18,21,<br>35,70,78<br>RPT-B5,49.-10/25/07<br>CII- NEG. | A30, wk25,B5,15,17,<br>21,35,53,56.<br>CII- NEG. | B78 enhanced | A2,9,25,28,30,32. BW4<br>B50,78,62,56,75,35,71,72,<br>45,46,18,64,54,76.CW6,17,<br>10,18,9,2,16,14,1,4,5,15<br>DR7,12,9,53 DQ4,9. |

FIG 16A

| | | | | BROAD |
|---|---|---|---|---|
| 9 | CI-100 | CI-100<br>CI-100 | A29,66 B7,27,42,55,<br>60,61,73.<br>CII- cannot tell. | same |
| 10 | CI-30 | CI-31<br>CII-99 | A25,26,30,31,32,68<br>RPT-Negative | NEGATIVE TWICE<br>wk DQ5,6, | A10,29,31,32,34,43,66<br>B46,63,75<br>DQ4,5,6,7,8,9. |
| 11 | CI-0<br>CII-68 | CI-1<br>CII-86 | DR4,17,DQ7,8,9<br>Rpt-1/16/08MM DR4 | CW17,18,5,15,2,6<br>DR4 | same | CW5,2,6,15,17,18<br>DR4,15,16,11,13,17<br>DQ7,8,9. |
| 12 | CI-84 | CI-78<br>CII-74 | B5,15,18,35,53,70 | B53,51,35,75,18,78 | NT(not enough | A28,33. B5,14,18,35,53,<br>75,78.<br>DR3,6,9. |
| 13 | CI-56 | CI-84<br>CII-71 | A2,68,69,23,24<br>B57,58.<br>CII-NT( No serum left)<br>A23, B57, B58 in 8/9/07<br>but not in 8/10/07 | A2,68,69<br>CII-NT | same+B57,58 | A2,23,24,68,69<br>B8,12,57,58,37,41,42,45<br>DR1,9,10,103,51 DQ4,5,6 |
| 14 | CI-0<br>CII-63 | CI-0<br>CII-63 | DQ1,5,6 | DQ1,5,6 | same | DR1,4,103<br>DQ1,5,6,2,8. |
| 15 | CI-46<br>CII-43 | CI-98<br>CII-79 | A23,24. B44,57 | A23,24,32,25. B45,76,<br>57,58,75,53,82,44,62<br>63<br>DR8,11,13,17 DQ2. | | A1,2,23,24,25,28,32,33<br>B8,14,18,35,39,45,67,62,73<br>75,76,78,82, BW4<br>DR3,5,6,7,8,9,11,12,13,14<br>17,18. DQ2 |
| 16 | CI-21<br>CII-0 | CI-76<br>CII-0 | A23,24,25,32,Bw4 | A23,24,25,32, Bw4 | same | A23,24,25,30,32,<br>B50,62,BW4. |
| 17 | CI-84 | CI-88<br>CII-34 | A2,28 B17,35,49,50<br>53,62,63,71,72. | A2,68,69,24,B49,56,63<br>B57,58,49,62,50,75,71 | same+<br>Cw10,12,15 | A2,9,11,28. B17,21,35,49<br>50,53,56,63,70,75,77,62.. |

FIG 16B

| # | | CI/CII | | | |
|---|---|---|---|---|---|
| 18 | | CI-48 CII-95 | CI- NOT CLEAR DQ1,5,6. | CW7 B37,63,65,48,81, 73 DQ5,6,2. | same | A23,24 B7,53,37,48,63,65, 73,81,CW7,8,1,10,12,15, 16,17,18 DR2,3,7,11,12,14,15,16,17 18,103,51 DQ2,5,6. |
| | | | | 72,77,35,53. | | DR17,DQ2. |
| 19 | | CI-32 CII-0 | CI-84 CII-74 | A11,26,29,32,34,36, Possible wrong calls. CII-NEGATIVE | A30,11,25,26,66,43, 31,29,wk34 DQ5,6 | same+ A1 enhanced B57 added. | A1,3,10,11,19,28,43,66, 74,80 B8,18,64,73 DR15,16,DQ4,5,6,8,9. DP Possibles |
| 20 | | CI-23 CII-68 | A1,36. DQ1,5,6; wk RPT-NEGATIVE | NEGATIVE | same | A1,36. DQ4,5,6. |
| 21 | | CI-23 CII-63 | BROAD | ONLY B LOCUS Pos. | NT | BROAD AI & BII |
| 22 | | | B57,58 | B57,58,53,49,27,63. | same | A2,23,24,32 B57, 58,49,53,63,51,27, 77,44,38,52,59,37 13,44. DR17 |
| 23 | | | A25,26,34,29,31,32, 33,74. | A25,32,33,68,74,29, 34,66,31,2,69,26,43 30 CII NEG. | same | A32,34,29,68,74, 29,26,34,66,2,25, 31,33,66,69,43,30, CII NEG. |
| 24 | | | B7,27,42,48,60 61,81,54,55,56 RPT-B7,60,48,81,54, ?B56 DR4,53 | B7,27,67,60,81,42,73 48 DR4,53 | same | A25,66,26,30,34,43 31,29,11. B7,27,67,60,81,42,47,13,82, 54,55,56,51,64,78,73,48, 63,75. DR4,7,11,53,9,52DQ7,8,9 DP17,3,10,2,14,9. |
| 25 | | | A2 | A2,69 B57,58 CII NEG | same | A2,69 B57,58. DR1,7 |

FIG 16C

| | | | | | |
|---|---|---|---|---|---|
| 26 | | NEG | NEG | NT | NEG |
| 27 | | A24,25,26,32,66,74 | NEG | NT | A30. |
| 28 | | A1,2,3,11,29,32,68 ?34,?74. | NEG | NT | DR4 |
| 29 | | CI NT (No serum). CII-NEG. | CI NEG. DR1 | same | A10,28,29,30,33, 34,43,66 B16,42, 55,67. DR1,4,10,103,DQ5 |
| 30 | | CI NT (No serum). DR15. | CI NEG. DR15,16. | same | B7,81 DR 15,16. |
| 31 | | B8 | B8,63. CII-Negative | same | B8,B18,B14,B37,B59, B46,B42,B54,A33,A34 ?DQ2. |
| 32 | | B51,52,59. | A25,32. B51,63,49,57,53,78,7, 58,67,52,38,77,18, 59,8201,42,13,39,56,8 DQ7,8,9. | same+A24, B81. | A25,A32,A9,A33,A30,A1, B51,B63,B17,B49,B78,B53, B5,18,77,67,59,16,8201,13, 42,14,35,7,8,22,75,81,40,73 46,80. |
| 33 | | BW4 XTRA RXNS | A32,66,34,26,68,25,43 24,23,29,66,69,11,33, 2,31,30 BW4,CW7,17. DR53,1,4,DQ7,8,9. | same | A25,A9,A32,A10,A28,11,19,2 BW4,B73,B67,B39 CW7,CW17 DQ3,DR53,DR4,DR1,DR103 DQ8,2,4,DR10,11,7,51,9,6,8, DR2 DP17. |
| 34 | | weak B57 | A2,11,80,1,69,29,25,3 24,30,36,66,23,43,68, 26 B57,58,63,73, CW6,17,16,7,9,2,15, 14,10. DQ6,7 | same + more specificities bec.of higher | high BG |

FIG 16D

| | | | | |
|---|---|---|---|---|
| 35 | | A30,31,B13 | Same +B47<br>Same +DP9. | A30,31,25,34,32,29,66,33,74<br>26,43. B13,62,75,76,47,49,<br>45,50,63,77,57,44,60,61,41,46.<br>DR7,9,12,11,4,17,13,53,52<br>DQ2,9,4,7 DP17,3,10,1,5,19<br>14,2,9,13,11,4. |
| | | A30,31 B13,75,62,76.<br>DR7,9,53 DQ2, DP17,<br>3,10. | | BROAD C I. |
| 36 | CI-99<br>CII-83 | BROAD IgG | NT | CII-DR11,13,17,14,8,18,52<br>DQ2,5,6,7,4,DP10,17,3,2,14,<br>9,4. |
| | | A1,2,3,11,25,26,29,30,<br>31,33,34,43,66,68,69<br>74,80.B7,8,13,18,27,<br>35,41,44,45,47,48,49,<br>50,51,53,56,57,58,60<br>61,62,63,67,73,76,78<br>81,8201<br>CII-NT | | |
| 37 | CI-99<br>CII-75 | BROAD IgG | NT | A2,9,29,30,31,33,34,43,66,<br>68,69,74.BW6,49,44,63,52,<br>47,13,51,27.<br>DQ5,6,4,8. |
| | | A29.B18,27,35,44,45,<br>49,50,56,62,71,75,76,<br>78,8201,67.<br>CII-NT | | |
| 38 | CI-98<br>CII-96 | IgM-A2,68,69<br>IgG-wk68 | NT | A2,11,25,26,29,30,31,32,<br>33,34,36,43,66,68,69,74<br>B7,8,13,18,27,42,47,48,49<br>51,55,60,61,63,64,65<br>73,81,CW7,17.<br>DR7,17,11,18,13,8,14,12,16.<br>DQ2,7,4,9,4,5 DP3,19,1,17,5,<br>13,11,10,14,9,4.. |
| | | A2,25,26,33,34,68,69<br>B64<br>CII-NT | | |
| 39 | CI-98<br>CII-80 | A2,3,11,36,68.<br>RPT-A2,3,11,36<br>B17??<br>wrong called A36! | NT | A68,11,69,3,11,2,24,30,36,1,<br>32,24,74,80,31,29,<br>B57,58 CW18,5,17,2,15,6,4,<br>8.<br>DR1,4,7 DQ5,6,7,4,8. |
| | | A2,3,11,68,69<br>B57,58<br>CII-NT | | |
| 40 | CI-96<br>CII-86 | BROAD IgG | NT | A24,32,23,25,30 BW4,62,75,<br>76,45,60,61,50,46,35,27,41,<br>54,39,48,56,73,67,72,8201<br>81,18. |
| | | A32,25,24,23, BW4,62<br>45,75,76,50,60,61, | | |

FIG 16E

| | | | CII-NT | | BROAD C.I. |
|---|---|---|---|---|---|
| | CI-56 | CI-99 | A2,68,69. B7,42,55 IgM-B57,58. | A2,68,69 B7,42,55,56 57,58,67,81,8201. CII-NT(No serum) | DR9,12,7,10,53,52 DQ2,5,9, 5,4. |
| 41 | | | | | CII-NT |
| 42 | CI-95 | CI-95 | BROAD IgG | A1,3,11,24,25,26,29, 30,31,32,33,34,36,43 66,74.B -ALL except 46,51,57,58,59,63,65. DR11 DQ5,4 DP2, 17,3,10,9,14. | same | A24,1,32,11,29,31,74,36,3, 30,34,33,80,66,33,26,25,43, 68. BW6,B44,47,27,49,13, 53,77,37,51,38,52,59,63. DR11,4,1,103,13 DQ5,6,4,8 2 DP17,3,10,2,14,9,1,5,19, 13,4,11. |
| 43 | CI-63 | CI-97 | A1,3,11,23,24,25,36. B44 CII-NT | A1,25,36,74,80. B44,45,76,8201. Rpt-A11pos.1/17/08 CII-Negative | same+A29,3 B57 | A1,2,3,11,25,29,30,31,32 33,36,74,80. B44,45,49,50, 52,56,57,58,63,76,8201. DP17,19,1,5,3,10,13,14,9,11. |
| 44 | CI-20 | | B62,75, Undefined. IVIG inhibition. | BW6, CW9,10 IVIG inhibition. DR11,DQ5,6 DP2,19. | same | A34,80. BW6, B57,63,77,13 49. CW2,6,9,10. DR11,7,15,16,53 DQ5,6,4 DP19,1,4,5,2,10,13,3,11,4. |
| 45 | CI-29 | CI-99 CII-98 | A1,36. A1 no inhibition Rest inhibited. | A1,11,23,24,25,26,29 36,43,66,80,B60,70. CW9,10. A1 no inhibition Rest inhibited in C1q. | same+A30. | A1,11,23,24,25,26,29,30,31 32,33,34,36,43,66,68,74,80 B7,8,13,18,35,38,39,41,42, 44,45,46,47,48,49,50,51,52 53,56,59,60,61,62,63,64,71 72,73,75,76,77,78,81,8201. Cw1,7,8,9,10,12,14,15,16,17 Ser date-6/19/07 |
| 46 | CI-50 | CI-92 CII-89 | A1,3,11,36.?B51. A1,3 ? inhibited A11,36likely not inhibited. | A1,3,11,25,36. B18,35,51,53,78. A3,11 not inhibited Rest inhibited. | same | A1,3,11,23,24,25,26,29,30, 31,33,34,36,43,66,68,74,80 B18,35,37,38,39,51,52,53, 64,75,76,77,78. |
| 47 | | | B57,62. | B46,50,56,58,49,77, | same | A1,3,11,23,24,25,26,29,32, |

FIG 16F

| | | | | |
|---|---|---|---|---|
| 48 | | A25,26,34. | 35,76,63,53,57,78,51,71,75,72,62. CW9,10. | 34,36,43,66. B56,58,50,35,49,78,46,71,51,53,72,77,57,76,63,52,13,45,75,62,44,67,55,42,8201,59,38,64,18,41,39,54. CW9,10,7,18,15,2,5,6. |
| | | | DQ4,5,6 DP17,19,3,1,5,10,9. | DR1,4,52 DQ4,5,6,8,9 DP17,19,1,5,3,10,13,14,9,11. |
| | | A25,26,34. | A25,66,26,43,34,66,68,33. B45,76,8201. | A26,66,25,43,34,68,66,33,69,1,11,33,36,29,30,24,23,30,80. B45,76,8201,44,50,49,62. |
| 49 | | | DR7,11,9,53 DQ2,9,7,4 DP10 | DR7,119,10,12,4,17,53 ,52 DQ2,4,7,8,9 |
| | | | A26,66,43,25,34,68,30,11,68,29,33,23,29,69,32,24. BW4 DR4,53 DQ7,8,9,4. | A26,66,34,25,68,43,11,23,33,69,32,30,24,66,29,2,31,74 BW4, B39. DR4,1,7,9,11,103,53 DQ7,8,9,2,4. |
| 50 | | B7 | B67,27,81,7,42,8201,27,56,55,60,73,61,54,48,38,57,46,8,62, | A66,32,24,23,74,25. B67,56,8201,27,42,81,7,27,55,60,73,61,48,8,54,47,57,13,63,41,62,78,51,75,58,64,46,71,39,76,37,59,35,52,53,77,38,65. |
| | | | CII-Negative. | CII-Negative. |
| 51 | | A1 | A1,29,36,26,80,43,24 B76. | A1,29,36,26,80,43,24,23,30 B76,45,44,8201,27. DR1,103. |
| | | | CII-Negative. | |
| 52 | | A2,68,69. | A2,24,69,68,25,34,66,33,26,29,30,23,31,30. | A69,2,34,68,24,25,33,34,66 26,66,29,30,33,31,43,23,32,11,74,36. B55,67,46,42,63. |
| | | CII-Negative. | CII-Negative. | CII-Negative. |

FIG 16G

| | | | | | |
|---|---|---|---|---|---|
| 53 | | A32 (POSS A25) B51,52,59. B51,B52,B18,B49,B63,B7 B77 | A25,32,24. B53,63,49 51,78,57,67,58,52,38, 77,18,59,8201,42,39 13,56,8. DQ7,8,9. | NT | A25,32,24,23,33 B51,63,57 49,53,78,58,52,77,18,67,59, 38,8201,13,42,35,64,7,39,8, 56,65,75,81,61,55,60,46,73 54. DR7,15,16 DQ7,8,9,2,4 |
| 54 | | B57,62. | B76,57,63,75,62,77,46 50,49,56,13,53,35. CW9,10. DR4,53 DQ7,8,9. | same | A23,24,68,69,2 B76,57,75,63 62,57,77,49,50,56,46,13,35, 53,7,81,8201,71,72,27,67,58 78,27,42,51,55,52,73,60,45. Cw9,10,8. |
| 55 | | A26 | A26,66,34,11,25,43,1, 36,80,30,29,66. DR7 | same | A26,25,11,1,43,34,66,36,30, 80,29,24,66,3,33,68,23,68, 69,31. B76,62,75,45,8201, 44,77,46,50,63,57,49,72,53 35,71,56,58,78,47,13. DR7,11 DQ2,9 DP10,2,17. |
| 56 | | B13 | B13,27,81 CW18,17,2,6,15,5. DR7. | NT | A66,30. B13,27,81,60,7,47, 61,53,73,35,75,48,49,50,77. CW18,17,5,6,2,15,4. DR7,9,53,52 DQ2,4,9. |
| 57 | | A1. B62 | A1,24,3,11,30,80,36, 29,34,25,29,32,23 B77,46,63,50,57,49,56 76,53,35,75,62,58,71, 78,72,45,51. CII-Negative. | same | ALL except A2,68,69. B7,8 48,41,61,60,73,81,42. CW9,10 DR8 |
| 58 | CI-0 CII-0 | CI-26 CII-9 | NEGATIVE | NEGATIVE | same | A203 B7,22,42,54,55,56,67, 81,8201 DQ4 |
| 59 | CI-0 CII-0 | CI-71 CII-0 | Negative | NEGATIVE | same | A25,26,34,66,2,68,69,29,32, 43,74. B63 |

FIG 16H

| | | | | | |
|---|---|---|---|---|---|
| 60 | CI-0<br>CII-0 | CI-0<br>CII-0 | CI,II-NEGATIVE | CI,II-NEGATIVE | same | CI,II-NEGATIVE |
| 61 | CI-0<br>CII-0 | CI-0<br>CII-51 | CI- NEGATIVE<br>CII-Weak reactivity. | CI- NEGATIVE<br>DR53 | same | CI- NEGATIVE<br>DR53 |
| 62 | CI-48<br>CII-55 | CI-95<br>CII-88 | IgM Undefined.<br><br>DQ2,6, Undefined. | NEGATIVE<br><br>DQ2,5,6. | A2,25.<br><br>same | A2,26,50,1,10,11,25,28,30,34<br>43,66,68,69 B17,21,35,44,49<br>53,56,57,58,62,63,75.<br>DR7,DQ2,6,4,5,9. |
| 63 | CI-34<br>CII-58 | CI-98<br>CII-91 | A24,68,69.<br>In Vitro inhibition.<br>DR15,51,DQ1,5,6. | A24,2,68,69,11,3,34,<br>36,80.<br>DR51, DQ5,6. | same | A1,2,3,11,24,29,31,33,34,36<br>66,68,69,80.-Ser.D-3/5/07<br>DR1,2,9,10,15,16,103,51,53,<br>DQ5,6,8,9. |
| 64 | CI-17<br>CII-40 | CI-99<br>CII-96 | IgM, IgG of broad<br>specificity for both<br>CI and CII.<br>Moderate inhibition. | A30,31,34 B49,50,45,<br>62,75,44,76,13,57,58,<br>47,60,63,61,53,64,41,<br>8,8201,27,65,56.<br><br>DR13,11,17,14,13,12,<br>8,18,7,15,52 DQ5,6,4 | same<br>66,3,33,11<br>67,7,71,59,35,81,5<br>72,37.<br><br>same | A1,11,26,28,30,31,32,33,34<br>36,43,66,74,80. B7,8,12,13,<br>14,15,16,17,21,27,35,40,41,<br>42,47,48,52,53,55,56,59,67<br>70,81,2708,4005,8201.<br>DR7,8,11,12,13,14,15,17,18<br>52 DQ1,4,5,6. |
| 65 | CI-0<br>CII-0 | CI-70<br>CII-67 | NEGATIVE | A30<br>CII- NEGATIVE | same | A1,80. B7,8,22,35,42,50,53,<br>55,56,62,67,75,76,78,81,<br>2708,8201<br>DR8,11,12,13,14,17,18. |
| 66 | CI-0<br>CII-0 | CI-0<br>CII-999 | NEGATIVE | A11<br>CII- NEGATIVE | same | Invalid test. High BG. |
| 67 | CI-78<br>CII-93 | CI-99<br>CII-88 | IgG, IgM- A1,3,11<br>CII- unclear.<br>Significant inhibtion. | A24,1,3,36,80,34,23,11<br>25,66,33,30,43,68<br>B7,81,27,56,67,42,76,<br>60,73,53,78,55,35,78,<br>8,62,51,48,75,13,47,61.<br>DR17,11,13,8,14,18<br>DQ7,2,9,6,8DQA1*ST456 | same | A24,1,3,36,80,34,23,11,26,69<br>25,66,33,30,43,68,31,32,<br>B7,81,27,56,67,42,76,<br>60,73,53,78,55,35,78,<br>8,62,51,48,75,13,47,61.<br>DR17,11,13,8,14,18,7,9,12,52<br>DQ7,2,9,6,8,DQA1*ST456 |

FIG 16I

| | | | | | |
|---|---|---|---|---|---|
| 68 | CI-0<br>CII-0 | NEGATIVE | NEGATIVE<br>CII-NT | same | B58<br>CII-NT |
| 69 | CI-33<br>CII-75 | ALL CELLS LYSED | B8<br>CII- NEGATIVE | same | B8<br>CII- NEGATIVE |
| 70 | CI-9<br>CII-32 | CI-99<br>CII-56 | IgM, IgG of undefined specificity for both CI and CII.<br>But inhibited. | B57,58<br><br>DQ2 | same+A1,11,24. | A24,11,2,3,25,1,32,80,36,68<br>23,69,33,29 B57,58,49,53,77<br>63,51,27,38,52,59,47,37,44<br>13,76.<br>DQ2,6,9. |
| 71 | CI-0<br>CII-0 | CI-12<br>CII-63 | Non specific IgG antibody. | NEGATIVE<br>Possible wh DQ5 | same | A30,31<br>DQ5,6,4. |
| 72 | CI-0<br>CII-0 | CI-25<br>CII-0 | NEGATIVE | NEGATIVE | same | A23,24,80. |
| 73 | CI-0 | CI-0<br>CII-70 | NEGATIVE<br><br>NEGATIVE | CI-Negative<br><br>DR53 | High back ground.<br>same | CI-Negative<br><br>DR1,9,10,17,53<br>DQ8,9. |
| 74 | CI-64<br>CII-80 | CI-99<br>CII-52 | A3,23,24,11<br>Significant inhibition.<br>CII-? Rituxan | A24,11,3,80,1,36,<br>23,32,30,25,B82,<br>56,67,42,55,7,76<br>81,54.<br><br>DR53,DQ7,8,9<br>?DQA3 | same<br><br><br><br><br>NT | A,1,3,23,24,11,25,26,<br>29,30,31,32,33,34,36<br>66,68,69,74,80. B44,<br>7,8,12,14,17,18,22,27<br>35,37,42,45,51,53,59<br>63,67,76,78,81,8201.<br>DR53,DQ7,8,9.<br>?DQA3 |
| 75 | CI-0<br>CII-100 | CI-0<br>CII-69 | CI- NEGATIVE<br>CII- ?RITUXIMAB | CI NEG.<br>DQ5 | same<br>DQ5,6,4 | CI NEG.<br>DR15 DQ6,4,5. |
| 76 | CI-22<br>CII-85 | CI-23<br>CII-96 | IgM-A11 by Long i.<br>DQ1,5,6.<br>RPT-NEGATIVE BY AHG<br>RPT-DQ2,5,6. | NEGATIVE<br>DR53 Rpt+DQ2,6 | same | A11,29,25,6601<br>DR15,51,53 DQ2,6,5,8.<br>Serum date-8/10/07 |

FIG 16J

| | | | | | | |
|---|---|---|---|---|---|---|
| 77 | CI-0<br>CII-0 | CI-91<br>CII-20 | NEGATIVE | NEGATIVE | same | A23,24,25,26,66,11,30,31,43<br>BW6<br>CII- NEG. |
| 78 | CI-0<br>CII-7 | CI-13<br>CII-0 | NEGATIVE | NEGATIVE | same | B51,75,78.<br>CII-Negative. |
| 79 | | | NT | NEGATIVE | NT | NEGATIVE |
| 80 | | | NT | NEGATIVE | NT | NEGATIVE |
| 81 | | | NT | NEGATIVE | NT | NEGATIVE |
| 82 | | | NT | NEGATIVE | NT | NEGATIVE |
| 83 | | | NT | NEGATIVE | NT | NEGATIVE |
| 84 | | | NT | NEGATIVE | NT | NEGATIVE |
| 85 | | | NT | NEGATIVE | NT | NEGATIVE |
| 86 | | | NT | NEGATIVE | NT | NEGATIVE |
| 87 | | | NT | NEGATIVE | NT | NEGATIVE |
| 88 | | | NT | NEGATIVE | NT | CI-B27 |
| 89 | | | NT | NEGATIVE | NT | NEGATIVE |
| 90 | | | NT | NEGATIVE | NT | NEGATIVE |
| 91 | | | NT | NEGATIVE | NT | NEGATIVE |
| 92 | | | NT | NEGATIVE | NT | NEGATIVE |
| 93 | | | NT | NEGATIVE | NT | NEGATIVE |

FIG 16K

| | | | | | |
|---|---|---|---|---|---|
| 94 | | | NT | NEGATIVE | NEGATIVE |
| 95 | | | NT | NEGATIVE | NEGATIVE |
| 96 | | | NT | NEGATIVE | NEGATIVE |
| 97 | | | NT | NEGATIVE | NEGATIVE |
| 98 | CI-12 CII-4 | CI-33 CII-0 | IgM?specificity. Inhibition cannot tell. | Negative. CII-Negative | CI-Wk B78 | A24,2403,9,23B51,78 |
| 99 | | | NEGATIVE | A26,34,66,43,25 DR4 | | A26,34,66,43,25,68,33 DR4,7,9,53,52 DQ4 |
| 100 | | | B18,65 | B18,64,65. | | A3,33 B18,64,65,8,78 51,54,35,56,8201,27, 53,67,7,81,42,37,55. DR1,103,9,17,8,12,15, 16,10,13,11,18,7,14,51 52, DQ5,6,4,8. |
| | | | | DR1,17,103,9,51 DQ5,6,4. | | |
| 101 | | | NEGATIVE | A11,25,66,43,1 | | A11,25,66,1,43,26,34, 36,80,3,30,24,32,30 B73 DR7,11,9 DP10,17,2 3,14,9,4,1,19. |
| | | | | DR7,11 | | |
| 102 | | | NEGATIVE | A25,32 B51,53,78,49,63 52,35,57,58. | | A32,25,23,24 B51,78 53,49,63,52,35,51,18 57,59,75,58,77,67,37 8201,13,38,64. CII-Negative |
| | | | | CII-Negative | | |
| 103 | CI-0 CII-33 | CI-31 CII-53 | NEGATIVE | NEGATIVE | SAME | A28,33,34,28 B8 DR7,10,53. |
| 104 | CI-0 CII-29 | CI-32 CII-56 | CI- NEGATIVE DR11,13-IgM | NEGATIVE | SAME | A23,24,25,32 DR11,13,14,17,18. |
| 105 | CI-100 | CI-98 | BROAD CI ,CII | A69,33,23,80,68,24,29, | SAME | A1,3,23,24,25,26,29,30,31,32, |

FIG 16L

| | | | | |
|---|---|---|---|---|
| | CII-100 | CII-96 | | 31,34,36,66,74,43,26,1,<br>32,3 B76,56,8201,47,55<br>60,8,27,67,61,46,7,57,58<br>81,42,13,73,54,63,48,41<br>CW9,10,8,18,14,16,1,7,6<br><br>DR11,17,7,13,52 DQ5,6 | 33,34,36,43,66,68,69,74,80<br>B7,8,13,27,37,41,42,44,45,46<br>47,48,49,50,54,55,56,57,58,<br>60,61,62,63,64,67,73,75,76,<br>81,2708,8201,CW1,2,3,9,10,6,<br>14,16,17,18,6,7,8,12,<br>DR7,8,9,11,12,13,14,17,18<br>DQ5,6,DR52-Possible |
| 106 | CI-0<br>CII-0 | CI-21<br>CII-0 | NEGATIVE | NEGATIVE | SAME | A24<br>CII-NEGATIVE |
| 107 | | CI-92<br>CII-60 | B44,45 | A1 B76 | SAME+B8201,44, | A1,23,24,25,29,32,36,80,2403<br>B7,13,27,37,41,42,44,45,47,<br>48,49,50,54,55,56,57,58,60,<br>61,62,63,67,75,76,77,81,2708<br>8201,CW1,4,5,14,18.<br>DR7,8,11,12,13,16,103 |
| | | | CII-NEGATIVE | CII-NEGATIVE | | |
| 108 | | | A29, B44<br>B44-Rechecked wrong<br>call per Tami<br>Rpt1/15/08-No B44 | A29,43 B7 | SAME | A3,11,23,25,26,29,30,31,32,<br>33,34,43,66,68,74,B7,8,13,27<br>42,44,45,47,48,54,55,56,60,61<br>67,73,76,81,2708,8201,CW2,3<br>9,10,5,6,15,16,17,18,1<br>DR8, DQ4 |
| | | | | CII-Negative | | |
| 109 | CI-0<br>CII-0 | CI-55<br>CII-64 | CI-Negative<br>DR3, DQ7,8 | CI-Negative<br>DQ8,7,9,4 | | A2 B52,57,58<br>DQ8,4,7,9 |
| 110 | CI-98<br>CII-96 | | A1,36 | A1,34,68,33,36,25,69,34<br>66,26,33,30,3,11,29,<br>BW6 | | |
| 111 | CI-21<br>CII-0 | CI-1<br>CII-0 | A3-IgM | CI,CII- NEGATIVE | SAME | CI,CII- NEGATIVE |
| 112 | CI-0<br>CII-30 | | CI- NEGATIVE<br>IgM- UNCLEAR | CI- NEGATIVE<br>Wk DR4 | SAME | DR4 |
| 113 | CI-2 | | CI- NEGATIVE | CI- NEGATIVE | same | CI- NEGATIVE |

FIG 16M

| | | CII-DR53, BROAD | DR53 DQ7,8,9 | DR53 DQ7,8,9,2,4 |
|---|---|---|---|---|
| | CII-88 | | | |
| 114 | CI-0<br>CII-0 | CI-66<br>CII-71 | CI-NEGATIVE<br>CII-NEGATIVE | A2,203 B7,17,81<br>DR1,4,DQ3,7,8,9 same |
| 115 | | CI-57<br>CII-38 | CDCXM B-DTT NEG<br>CDCXM B-POS | CI-NEGATIVE<br>CII-NEGATIVE A2,203,210,68,69 B75<br>DR15,51 DQ6 same |
| | | CI-0<br>CII-0 | CDCXM B-DTT NEG<br>CDCXM B-POS | CI-NEGATIVE<br>CII-NEGATIVE CI,CII- NEGATIVE same |

TOTAL:991 SPECS.   TOTAL:1034SPE
75 POSITIVE SAMPLES

FIG 16N

LUMINEX C1Q VALIDATION SUMMARY - IVIG SAMPLES

| NO. | SERUM D. | CDC RESULT | C1Q RESULT NEAT | C1Q RESULT 5%A/G/PBS | C1Q RESULT 5%IVIG | LUMINEX IgG |
|---|---|---|---|---|---|---|
| 1 | 8/2/2007 | NT | wk A2. B57,58 CII-NT | same | same inhibited | A1,2,36 B57,58. DQ7,8,9. |
|  | 8/2/07PRE | UNCLEAR SPEC CII- Rituxan Decreased. | B57,58 DQ7,8,9 | same |  | A1,2,36 B57,58. DQ7,8,9. |
|  | 8/2/07POST |  | B57 only CII NEG | same |  |  |
|  | 8/2/07PRE | NT | B57,58 DQ7,8,9 | same |  | A1,2,36 B57,58,63 CW2,5,6,15,17,18. DQ7,8,9. |
|  | 8/30/07POST | NT | B57 only CII NEG | same |  |  |
|  | 8/30/07PRE | NT | B57,58 | same |  | A1,2,36 B57,58,63 CW2,5,6,15,17,18 DQ8,7,9 |
|  | 8/30/07POST | NT | DQ7,8,9 B57 only CII NEG | same |  | Same as above |
|  | 8/30/07PRE | NT | B57,58 DQ7,8,9 | same |  | Same as above |
|  | 9/5/07POST | UNCLEAR SPEC | B57,58 DQ7 | same |  | Same as above |
|  | 10/25/2007PRE | NT | B57,58 | same |  | A1,2,36 B57,58 Cw2,5,6,15,17,18 DQ7,8,9 |
|  | 10/25/07POST | NT | Negative | same |  | Same as above |
|  | 11/19/07PRE | NT | Negative | same |  | A1,2,203 B57,58 CW6,17,18 DQ7,8,9 |

FIG 17A

| NO. | SERUM D. | CDC RESULT | C1Q RESULT | | | LUMINEX IgG |
|---|---|---|---|---|---|---|
| | | | NEAT | 5%A/G/PBS | 5%IVIG | |
| | 11/19/07POST | | | Negative | same | Same as above |
| 2 | 1/15/2007 ALSO PRE | NT | NEGATIVE | INVALID HIGH BG. | NEGATIVE | CI-Negative |
| | 8/21/07POST | NT | DR53 | same | DR53 partial inhibition | DR1,9,10,17,53 DQ8,9. |
| | | | CI-Negative DR53 | CI-Negative same | | CI-Negative DR1,9,10,17,53 DQ8,9. |

| NO. | SERUM D. | CDC RESULT | C1Q RESULT | | | LUMINEX IgG |
|---|---|---|---|---|---|---|
| | | | NEAT | 5%A/G/PBS | 5%IVIG | |
| 3 | 7/20/07PRE | A3,23,24,11 | A24,11,3,80,1,36, 23,32,30,25.B82, 56,67,42,55,7,76 81,54. | same | marked inhibition. | A1,3,23,24,11,25,26, 29,30,31,32,33,34,36 66,68,69,74,80. B44, 7,8,12,14,17,18,22,27 35,37,42,45,51,53,59 63,67,76,78,81,8201. DR53,DQ7,8,9. ?DQA3 |
| | 8/10/07POST | CII-?Rituxan | DR53,DQ7,8,9 ?DQA3 | NT | | |
| | | CI-decreased | A3,11,24 | NT | | A1,3,11,23,24,25,29, 30,32,34,36,68,80. B7,8,17,18,22,27,37, 42,63,64,67,76,81,82. DR53,DQ7,8,9. |
| | 11/6/2007PRE | CII-?Rituxan | DR53,DQ8 | NT | | |
| | 11/7/2007POST | | A24,11,3,80,1,36 DR53 DQ7,8 A24,11,3. DR53 DQ8 | same | same | |
| | 12/18/07PRE | | A24,11,3,1,80,36 | same | same | |

FIG 17B

| | | | | |
|---|---|---|---|---|
| | | | | B59,38,46,54, DR53 DQ7,8 A24 ONLY DR53 ONLY | same |
| 12/18/07POST | | | | | |

| NO. | SERUM D. | CDC RESULT | C1Q RESULT | | LUMINEX IgG |
|---|---|---|---|---|---|
| | | | NEAT | 5%A/G/PBS  5%IVIG | |
| 4 | 8/9/2007 | A2,68,69,23,24 B57,58. confusing CDC results | A68,69,2 | same+A24,  marked inhibition. | A2,23,24,68,69 B8,12 17,37,41,42,45, DR1,9,10,103 DQ4,5,6. |
| | 8/10/07PRE | A2,68,69 | CII-NT  A2,68,69,24 B57 | NT | A2,23,24,68,69 B42,37,44,41,8,57,58 45 DR1,10,103,51 DQ5,6 |
| | 8/12/07POST | CII-NEG  A2,69 A68 v.weak | DR1  A2,68,69  DR1 | NT  marked in vivo inhibition. | A2,203,210,68,69,23 24,2403 DR1,10,103,51 DQ5,6. |

| NO. | SERUM D. | CDC RESULT | C1Q RESULT | | LUMINEX IgG |
|---|---|---|---|---|---|
| | | | NEAT | 5%A/G/PBS  5%IVIG | |
| 5 | 8/16/07PRE | waiting for CDC | NEGATIVE | same  B44,82,some CW,DR 52added,possibly FP. in IVIG sample. | B51,75,78. CII-Negative. |
| | 8/16/07POST | NT | NEGATIVE | same | |

| NO. | SERUM D. | CDC RESULT | C1Q RESULT | | LUMINEX IgG |
|---|---|---|---|---|---|
| | | | NEAT | 5%A/G/PBS  5%IVIG | |
| 6 | 7/7/2007 ALSO PRE | A2,68,69-Long incu. | A24,2,68,69,11 B49,56,63,50,75, 62,57,58,53,35, 77,71,72. | same-A11, B77,72  partial inhib. A24 inhibited | A2,11,23,24,68,69. B17,21,35,49,50,53, 56,62,63,70,71,72,75, 77 |

FIG 17C

| | CDC RESULT | C1Q RESULT | | DR17 DQ2 |
|---|---|---|---|---|
| 7/22/07POST | CII NEG<br>A2,69; A2 not inhib.<br>A28 inhibited | CII NEG.<br>A2,68,69B57,58 | same+A11,<br>B49,62 | |
| 8/13/07PRE | A2,69 | A2,68,69wk 24<br>B57,58wk21,62. | NT | A2,24,68,69 B17,21,<br>35,42,52,53,55,56,62<br>63,70,71,72,75,77.<br>CII NEG. |
| 8/15/07POST | A2 | CII NEG.<br>A2,68,69<br>B57,58<br>CII NEG. | NT | Same as above, only<br>no B55. |
| 8/29/07PRE | NT | A2,68,69<br>B57,58 | same | A24,2,11,32,68,69.<br>B17,21,35,52,53,55,<br>56,62,63,67,70,71,72<br>75,77. |
| 8/29/07POST | NT | CII NEG.<br>A2,68,69<br>B57,58<br>CII NEG. | same | CII NEG.<br>Same as above. |
| 8/29/07PRE | NT | A2,68,69<br>B57,58<br>CII NEG. | same | Same as above. |
| 9/10/07POST | NT | A2,68,69<br>B57,58<br>CII NEG. | same | A2,68,69 B17,21,35,<br>52,53,56,62,63,70,71,<br>72,75,77.<br>CII NEG. |

| NO. | SERUM D. | CDC RESULT | C1Q RESULT | | | LUMINEX IgG |
|---|---|---|---|---|---|---|
| | | | NEAT | 5%A/G/PBS | 5%IVIG | |
| 7 | 3/1/2007 | NT | CI NEG.<br>DQ5 | same<br>DQ5,6,4 | same<br>inhibited | CI NEG.<br>DR15 DQ6,4,5. |

FIG 17D

| | | | |
|---|---|---|---|
| 8/29/07 PRE | NT | CI NEG. DQ5,4 | DQ5,6,4 | A2 B49,17. DR15,8,11,13,17 DQ6,4,5,DQA1-ST456 |
| 8/30/07 POST | NT | CI NEG. DQ5,4 | DQ5,6,4 | A2 B49,17. DR15,8,11,13,17 DQ6,4,5 |
| 10/3/07 PRE | IgM-A2 B57,58 CI-NT | CI NEG. DR11,13 DQ5,6,7 | same same +DQ2, 4,DR17. | A2 B57,58,49 DR13,17,11,8,14,103, 15,12,18,52 DQ7,4 6,5,.DQA1-ST456 |
| 10/5/07 4:00 POST | CI-NT (not enough serum) | CI NEG. | same | A2,25,69 B57,58,49, 63,27,7,51CW17,5,18,2 DR13,11,8,17,14,103, 15,12,18,16,7,52,51 DQ7,6,2,5,4,8.DQA1-ST456 |
| 10/5/07 16:00 POST | CI-NT(not enough serum) DR15,DQ2,5,6 | CII NEG. | DR11,13 DQ5,6,7. | A2,25,69,32,24,68,34 B57,58,49,63,51,27,7 47,27,8201CW17,5,18,2 DR13,11,8,17,14,103, 15,12,18,16,7,52,51,1 DQ7,6,5,4,8.DQA1-ST456 |
| | DR15,DQ5,6 | DR11,13 DQ5,6,7 | same | |
| 10/5/07 4:00 POST | | CI NEG. | same +DQ2, DQ4 | A2,25 B57,58,49,63 CW17. DR13,11,8,17,14,103, 15,12,18,16,7,52,51,1 DQ7,6,2,5,4,8.DQA1-ST456 |
| 10/5/07 4:00 PRE | NT | CII NEG. | DR11,13 DQ5,6,7. | A2,25 B57,58,49,63 CW17. DR13,11,8,17,14,103, 15,12,18,16,7,52,51,1 DQ7,6,5,4,8.DP19 DQA1-ST456 |
| 10/13/07 POST | NT | CI NEG. DR11,13DQ5,6,4 | same +DQ2,7. | A2,25 B57,58,49,63 CW17. DR13,11,8,17,14,103, 15,12,18,16,7,52,51,1 DQ7,6,5,4,8.DP19 DQA1-ST456 |

| | | | | LUMINEX IgG |
|---|---|---|---|---|
| 10/15/07POST | NT | CI NEG.<br>DR11,13 DQ5,6. | A29.<br>same | A2,25,32 B59,57,58<br>63,51,53 CW17.<br>DR13,11,8,17,14,103,<br>15,12,18,16,7,52,51.<br>DQ7,6,5,4,8.<br>DQA1-ST456 |

| NO. | SERUM D. | CDC RESULT | C1Q RESULT | | LUMINEX IgG |
|---|---|---|---|---|---|
| | | | NEAT | 5%A/G/PBS | 5%IVIG | |
| 8 | 9/4/2007 | CI NEG<br>DQ5,6- partial<br>inhibition. | B37,63,65,48<br>CW7,17,8,1,10. | same+B81<br>CW12,15. | B63,37,CW7,<br>Cw 6,17<br>inhibited. Rest neg.<br>DQ partial inhib. | A23,24 B7,53,37,48,<br>63,65,73,81. CW7,8<br>1,10,12,15,16,17,18.<br>DR9,13,52,1,2,7,11,12<br>14,17,18,103,51,<br>DQ2,5,6. |
| | 9/24/07PRE | NT | DQ5,6,2 | same | | B53,37,48,63,65,73,81<br>CW1,7,8,10,12,15,16<br>17 |
| | | | wk CW7 | same | | DR13 DQ2,5,6. |
| | 9/24/07POST | NT | DQ5,6<br>CI NEG<br>DQ5,6 | same<br>same<br>same | | Same as above. |
| | 10/30/07PRE | NT | B63,37 CW7 | same | | A23,24 B53,7,37,48,63<br>65,73,81 CW7,17,1,10<br>12,15,16,18,8<br>DR13,9,1,7,12,17,18,103<br>51 DQ2,6,5 |
| | 10/30/07POST | NT | Negative | DQ5,6,2 | | Same as above. |
| | | | B63,37 CW7<br>DQ5,6,2 | same | | |
| | 11/19/07PRE | NT | B63,37 CW7<br>DQ5,6 | same | | CI- SAME AS ABOVE<br>CII-SAME+DR10,11,14,<br>15,16. |
| | 11/19/07POST | NT | B63,37 CW7<br>DQ5,6 | same | | Same as above. |

| NO. | SERUM D. | CDC RESULT | C1Q RESULT NEAT | C1Q RESULT 5%A/G/PBS | C1Q RESULT 5%IVIG | LUMINEX IgG |
|---|---|---|---|---|---|---|
| 9 | 8/17/2007 | IgM-A11 DQ1,5,6. double doses-wrong call. | NEGATIVE DR53 | same | DR53 inhibited. | A11,29,25,6601 DR15,51,53 DQ2,6,5,8. Serum date-8/10/07 |
|  | 9/11/07PRE | NT | NEGATIVE DR53,DQ2,5,6. | same |  | A11,29,25 CW7 DR15,51,53,1,10 DQ2,6,5,8,9. |
|  | 9/12/07POST | NT | NEGATIVE DR53,DQ2,5,6. | same |  | A11,29,25 CW7,10,17 DR15,51. |
|  |  |  |  |  |  | DQ2,6,5,8,9. |

| NO. | SERUM D. | CDC RESULT | C1Q RESULT NEAT | C1Q RESULT 5%A/G/PBS | C1Q RESULT 5%IVIG | LUMINEX IgG |
|---|---|---|---|---|---|---|
| 10 | 10/3/2007 | IgM Undefined. | A2,25. | same | A25 not inhibited. | A2,26,50,1,10,11,25, 28,30,3443,66,68,69 B17,21,35,44,49 53,56,57,58,62,63,75. DR7,DQ2,6,4,5,9. |
|  |  | DQ2,6, undefined. Partial inhibition. | DQ2,5,6. | same | DQ2,5,6. |  |
|  | 10/12/07PRE | NT | Negative | same |  | A2,25,26,66 B57,58, 50,49. DQ2,5,6,4,9. |
|  | 10/13/2007 | NT | DQ2,5,6 Negative DQ2,5,6 | same |  | A2,25,26,66 B57,58, 50,49,63,44,62. DR1,7.DQ2,5,6,4,9. DP19. |

| NO. | SERUM D. | CDC RESULT | C1Q RESULT NEAT | C1Q RESULT 5%A/G/PBS | C1Q RESULT 5%IVIG | LUMINEX IgG |
|---|---|---|---|---|---|---|
| 11 | 8/6/2007 | Non specific IgG | NEGATIVE | same | NEGATIVE | A30,31 |

FIG 17G

| | | | | |
|---|---|---|---|---|
| | 10/11/07PRE | antibody. | NEGATIVE | same | DQ5,6,4. |
| | 10/12/07POST | NT | NEGATIVE | same | A30,31 DQ5,6 A30,31 B76,63,8201, 45 CW7,17,10. DR12,4,1,53,52 DQ5,6 DP19. |

| NO. | SERUM D. | CDC RESULT | C1Q RESULT | | LUMINEX IgG |
|---|---|---|---|---|---|
| | | | NEAT | 5%A/G/PBS 5%IVIG | |
| 12 | 9/19/2007 | CI- NEGATIVE CII-Weak reactivity. | CI- NEGATIVE DR53 | same  DR53 inhibited. | CI- NEGATIVE DR53 |
| | Post 3XPPs 9/27/07PRE | | NEGATIVE | same | CI- NEGATIVE DR53 |
| | 9/28/07POST | | NEGATIVE | same | CI- NEGATIVE DR53 |

| NO. | SERUM D. | CDC RESULT | C1Q RESULT | | LUMINEX IgG |
|---|---|---|---|---|---|
| | | | NEAT | 5%A/G/PBS 5%IVIG | |
| 13 | 11/5/2007 | | CI- NEGATIVE DR53 DQ7,8,9 | same  Partial inhibition. | CI- NEGATIVE DR53 DQ7,8,9,2,4 |
| | 11/5/2007PRE | | CI- NEGATIVE DR53 DQ7,8,9 | same | CI- NEGATIVE DR53 DQ7,8,9 |
| | 11/5/07POST | | CI- NEGATIVE DR53 DQ7,8,9 | same | CI- NEGATIVE DR53 DQ7,8,9,2,4 |

| NO. | SERUM D. | CDC RESULT | C1Q RESULT | | LUMINEX IgG |
|---|---|---|---|---|---|
| | | | NEAT | 5%A/G/PBS 5%IVIG | |
| 14 | 11/7/2007 | A29 B44 B44 Wrong called A29 NO INHIBITION | A29,43 B7 | same  A29 No inhibition | A29,30,29,43,32,33, 74,31,66,34,23,11,25 26,68 B7,81,27,76,45 27,60,44,61,42,47,82 48,13,67,73,56,55,8,54 CW2,10,16,17,9,18,5 |

FIG 17H

| NO. | SERUM D. | CDC RESULT | | CII-NEGATIVE | |
|---|---|---|---|---|---|
| | 11/7/2007PRE | CII-NEGATIVE | A29,43 B7 | same | 6,15. DR8 DQ4 |
| | 11/7/07POST | | CII-NEGATIVE A29 | same | |
| | | | CII-NEGATIVE | | |

| NO. | SERUM D. | CDC RESULT | C1Q RESULT | | | LUMINEX IgG |
|---|---|---|---|---|---|---|
| | | | NEAT | 5%A/G/PBS | 5%IVIG | |
| 15 | 7/31/2007 | A23,24,32 B44 | A23,2432,25 B76, 45,57,58,75,53,8201, 44,63,62,49,51,77 DR8,11,13,17 DQ2 | same | Partial inhibit. | A1,2,9,25,28,32,33, B8,14,18,35,39,45,62,73,75 76,78,8201,BW4 DR7,8,9,11,12,13,14,17,18 DQ2 |
| | 8/30/2007 | | Wk A24 | Negative | CII inhibited | |
| | 9/26/2007 | | Negative | same | | |
| | 11/1/07PRE | Weak Non-Specific Abs | CI-Negative CII-Negative | same | | A9,25,32; B12,15,17,35,38,49,51,53,67,82; CW7 DR11,12,7,8,13,17 |
| | 11/2/07POST | Negative | CI-Negative CII-Negative | same | | SAME AS ABOVE |
| | 11/16/2007 | | CI-Negative CII-Negative | same | | A9,25,32 B12,15,17,35 38,49,51,53,67,78,8201 CW7 DR5,6,7,8,17,DQ2 |
| | 11/29/07PRE | | CI-Negative CII-Negative | same | | A9,25,32 B17,35,38,49 51,53,63,75,76,77CW7 DR8,11,13 |
| | 11/30/07POST | | CI-Negative CII-Negative | same | | SAME AS ABOVE |

| NO. | SERUM D. | CDC RESULT | C1Q RESULT | LUMINEX IgG |
|---|---|---|---|---|

FIG 17I

| | NEAT | 5%A/G/PBS | 5%IVIG | |
|---|---|---|---|---|
| 12/5/2007 | A2,68,69,3 B78, 51,53 DR1 | same | A2 no inhibition Rest inhibited | A2,3,9,25,28,2403 B5, 14,18,35,53,71,75,77 78,8201 DR1,4,9,10,14,15,16 17,103,51 DQ5 |
| 16 | | | | |

FIG 17J

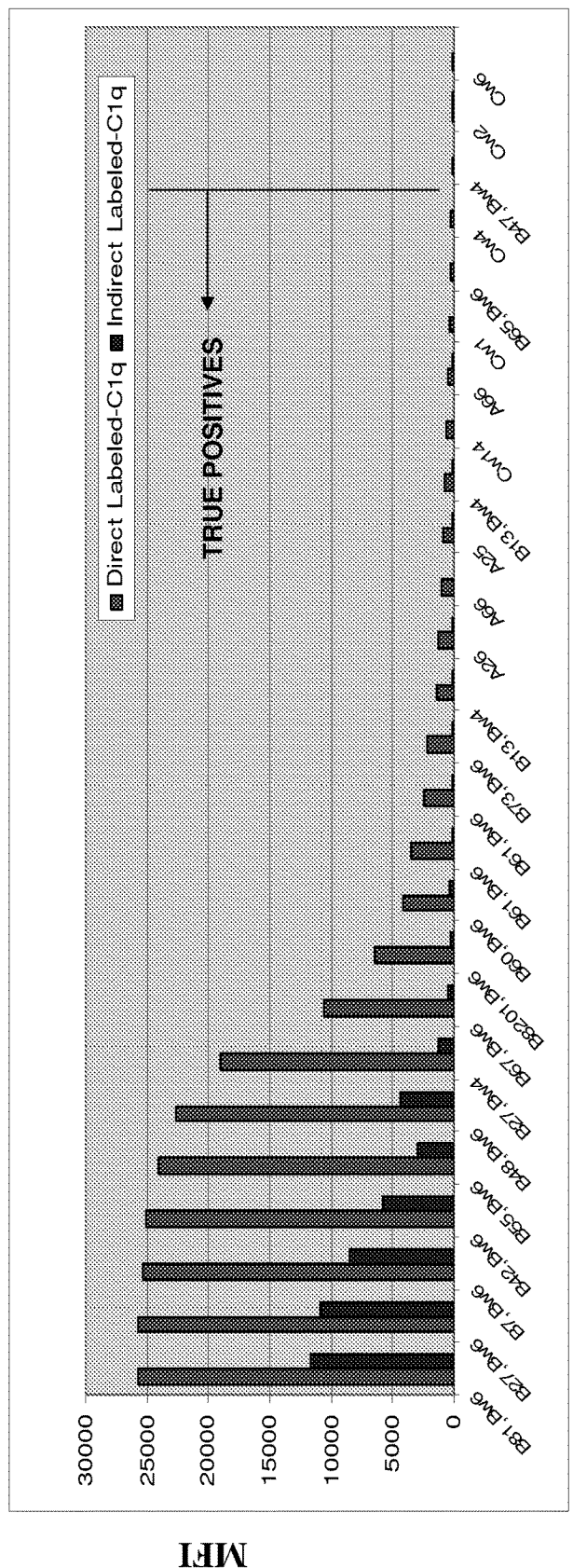

Subset of only the positive antibodies detected by directly labeled C1q (from slide 2) arranged by strength of indirectly labeled C1q reactions. Serum B.

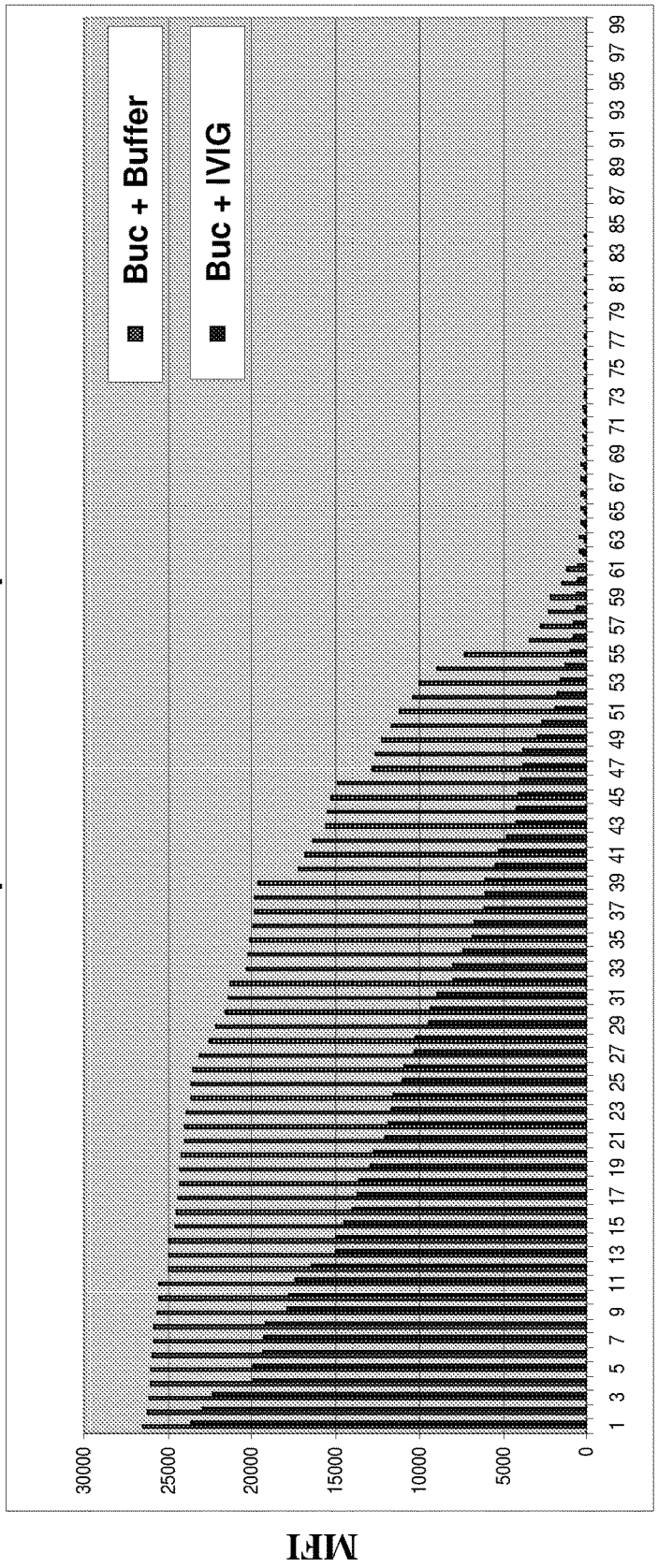

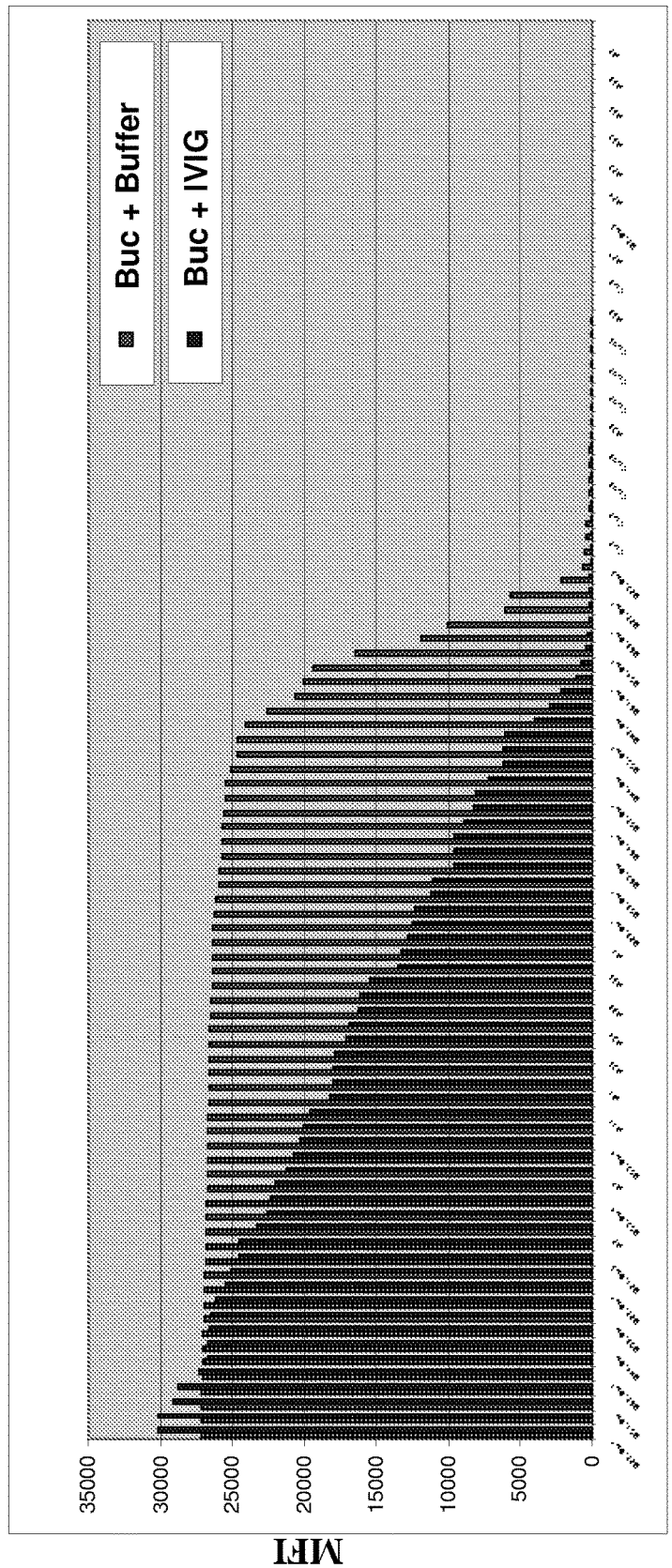

METHODS AND COMPOSITIONS FOR DETECTION OF COMPLEMENT FIXING ANTIBODIES

BACKGROUND OF THE INVENTION

The complement system is a complex group of proteins in blood that, in concert with antibodies and other factors, plays an important role as a mediator of immune, allergic, immunochemical and immunopathological reactions. Activation of the complement system can result in a wide range of reactions such as opsonization and lysis of various kinds of cells, bacteria and protozoa, inactivation of viruses, and the direct mediation of inflammatory processes. Through the hormone-like activity of several of its components, the complement system can recruit and enlist the participation of other humoral and cellular effector systems. These in turn can induce directed migration of leukocytes, trigger histamine release from mast cells, and stimulate the release of lysosomal constituents from phagocytes.

The complement system consists of at least twenty distinct plasma proteins capable of interacting with each other, with antibodies, and with cell membranes. Many of these proteins, when activated, combine with other proteins to form enzymes to cleave and activate still other proteins in the system. The sequential activation of these proteins, known as the complement cascade, follows two main pathways; the classical pathway and the alternative pathway. Both pathways converge at C3 and use a common terminal trunk which leads to cell lysis, bacterial opsonization and lysis, or viral inactivation.

The classical pathway can be activated by antigen-antibody complexes, aggregated immunoglobulins and non-immunological substances such as DNA and trypsin-like enzymes. The classical pathway of activation involves, successively, four components denominated C1, C4, C2 and C3. These components can be grouped into two functional units: C1 or recognition unit; and C4, C2, and C3 or activation unit. Five additional components denominated C5, C6, C7, C8, and C9 define the membrane attack complex (MAC) forming the terminal trunk common to both pathways that leads to cell lysis. The alternate pathway utilizes Factor B and bypasses the C1-C4-C2 steps, activating at C3.

The classical pathway begins with the C1-complex, which consists of one molecule of C1q and two molecules of both C1r and C1s. Activation of the C1-complex is triggered either by C1q's binding to antibodies from classes M and G, complexed with antigens, or by binding of C1q to the surface of a pathogen. Both C1r and C1s are serine proteases. Binding of C1q leads to conformational changes in the C1q molecule, which in turn leads to the activation of the two C1r molecules, followed by activation of the C1s molecules. In order to prevent spontaneous activation of this cascade, C1r and C1s are inhibited by C1-inhibitor, a serine protease inhibitor. Once activated, the C1-complex binds to and cleaves C2 and C4, producing C2a and C4b. C2a and C4b then bind to form a C4b2a complex, known as C3-convertase. Production of C3-convertase leads to cleavage of C3 into C3a and C3b; the latter joins with C2a and C4b (the C3 convertase) to make C5 convertase, which is the initial component of MAC.

Study and measurement of the activation of a complement pathway can provide an indication of many possible biological disorders. The complement pathway has been implicated in the pathogenesis or symptomatology of a broad spectrum of human diseases and pathologic conditions. Such diseases include immune complex diseases of several types, autoimmune diseases, in particular systemic lupus erythematosus, and infectious diseases, such as those found to be involved in infections with gram negative bacteria, viruses, parasites, fungi, and various dermatologic, renal, and hematologic diseases. Some disorders may be due to insufficient complement in the patient.

There remains a need in the field for methods for detecting complement fixing antibodies in a patient sample in a manner that is rapid, sensitive, and specific, particularly with respect to the ability to differentiate accurately and definitively among specific antigens.

The present invention addresses these needs.

Relevant Literature

U.S. Pat. Nos. 6,514,714 and 6,150,122; Wahrmann et al., J. Immunol. Methods. 275(1-2):149-60 (2003; and Smith et al., Am. J. Transplant. 7(12):2809-15 (2007).

SUMMARY OF THE INVENTION

The invention provides methods for sensitive and specific detection of complement fixing antibodies in a biological sample using complement factor C1q, including autologous complement factor C1q present in the biological sample and a detectably labeled antibody that binds the autologous complement factor C1q, exogenous human complement factor C1q and a detectably labeled antibody that binds the exogenous human complement factor C1q, detectably labeled exogenous human complement factor C1q, or a combination of autologous complement factor C1q and exogenous human complement factor C1q. The invention also features kits, systems, and devices for use in the methods of the invention.

In one aspect, the invention provides a method for determining the presence or absence of complement fixing antibodies in a biological sample from a subject that bind specifically to an antigen of interest, by contacting a solid substrate with an antigen of interest (AgI) immobilized thereon with a biological sample from a subject and complement factor C1q, wherein the contacting is for a sufficient time to allow anti-AgI complement fixing antibodies in the sample to bind to the AgI and to allow complement factor C1q to bind the anti-AgI complement fixing antibodies; incubating the solid substrate with at least one detectably labeled ligand capable of specifically binding the complement factor C1q bound to the anti-AgI complement fixing antibodies bound to the AgI; and detecting the presence or absence of the detectably labeled ligand bound to the complement factor C1q to determine the presence or absence of complement fixing antibodies that bind specifically to the AgI in the biological sample.

In some embodiments, the complement factor C1q is autologous complement factor C1q. In other embodiments, the complement factor C1q is exogenous complement factor C1q. In yet other embodiments, the complement factor C1q is a combination of autologous complement factor C1q and exogenous complement factor C1q.

In some embodiments, the solid substrate is a multiwell plate. In other embodiments, the solid substrate is a membrane. In yet other embodiments, the solid substrate is a microparticle, such as a polystyrene bead, a latex bead, or a magnetic bead. In some embodiments, the solid substrate is a cell. In other embodiments, the solid substrate is a cell membrane. In some embodiments, the biological sample is serum, blood, saliva, plasma, or urine. In some embodiments, the detectably labeled ligand is a detectably labeled antibody or binding fragment thereof. In some embodiments, the detectable label is a fluorochrome, a chromophore, an enzyme, a linker molecule, a biotin molecule, an electron donor, an electron acceptor, a dye, a metal, or a radionuclide.

In another aspect, the present invention provides a method for determining the presence or absence of complement fixing antibodies in a biological sample from a subject that bind specifically to an antigen of interest, by contacting a solid substrate with an antigen of interest (AgI) immobilized thereon with a biological sample from a subject and directly labeled exogenous complement factor C1q, wherein the contacting is for a sufficient time to allow anti-AgI complement fixing antibodies in the sample to bind to the AgI and to allow the directly labeled exogenous complement factor C1q to bind to the anti-AgI complement fixing antibodies; and detecting the presence or absence of the directly labeled exogenous C1q bound to the anti-AgI complement fixing antibodies to determine the presence or absence of complement fixing antibodies in the biological sample that bind specifically to the AgI.

In some embodiments, the solid substrate is a multiwell plate. In other embodiments, the solid substrate is a membrane. In yet other embodiments, the solid substrate is a microparticle, such as a polystyrene bead, a latex bead, or a magnetic bead. In some embodiments, the solid substrate is a cell. In other embodiments, the solid substrate is a cell membrane. In some embodiments, the biological sample is serum, blood, saliva, plasma, or urine. In some embodiments, the directly labeled exogenous C1q is labeled with a fluorochrome, a chromophore, an enzyme, a linker molecule, a biotin molecule, an electron donor, an electron acceptor, a dye, a metal, or a radionuclide.

In yet another aspect, the present invention provides a method for determining the presence or absence of complement fixing antibodies in a biological sample from a subject that bind specifically to human leukocyte antigens (HLAs), by incubating a biological sample from a subject with a collection of microparticles of different subtypes and complement factor C1q, wherein each microparticle is coated with a different purified HLA subtype, is derived from a cell population presenting the same HLAs, and wherein the incubating is for a sufficient time to allow anti-HLA complement fixing antibodies in the biological sample to bind to the HLAs and to allow the complement factor C1q to bind the anti-HLA complement fixing antibodies in the biological sample; incubating the microparticles with at least one detectably labeled ligand capable of specifically binding with the complement factor C1q bound to the anti-HLA complement fixing antibodies bound to the HLAs; and detecting the presence or absence of the detectably labeled ligand bound to the complement factor C1q to determine the presence or absence of complement fixing antibodies.

In some embodiments, the complement factor C1q is autologous complement factor C1q. In other embodiments, the complement factor C1q is exogenous complement factor C1q. In yet other embodiments, the complement factor C1q is a combination of autologous complement factor C1q and exogenous complement factor C1q.

In some embodiments, the microparticle is an agarose bead. In other embodiments, the microparticle is a latex bead. In yet other embodiments, the microparticle is a magnetic bead. In some embodiments, the biological sample is serum, blood, saliva, plasma, or urine. In some embodiments, the detectably labeled ligand is a detectably labeled antibody or binding fragment thereof. In some embodiments, the detectable label is a fluorochrome, a chromophore, an enzyme, a linker molecule, a biotin molecule, an electron donor, an electron acceptor, a dye, a metal, or a radionuclide. In some embodiments, the detecting is by flow cytometry.

In yet another aspect, the present invention provides a method for determining the presence or absence of complement fixing antibodies in a biological sample from a subject that bind specifically to human leukocyte antigens (HLAs), by incubating a biological sample from a subject with a collection of microparticles of different subtypes and directly labeled exogenous complement factor C1q, wherein each microparticle is coated with a different purified HLA subtype, is derived from a cell population presenting the same HLAs, and wherein the incubating is for a sufficient time to allow anti-HLA complement fixing antibodies in the biological sample to bind to the HLAs and to allow the complement factor C1q to bind the anti-HLA complement fixing antibodies in the biological sample; and detecting the presence or absence of the directly labeled exogenous complement factor C1q bound to the anti-HLA complement fixing antibodies to determine the presence or absence of complement fixing antibodies in the biological sample that bind specifically to HLAs.

In some embodiments, the microparticle is an agarose bead. In other embodiments, the microparticle is a latex bead. In yet other embodiments, the microparticle is a magnetic bead. In some embodiments, the biological sample is serum, blood, saliva, plasma, or urine. In some embodiments, the directly labeled exogenous C1q is labeled with is a fluorochrome, a chromophore, an enzyme, a linker molecule, a biotin molecule, an electron donor, an electron acceptor, a dye, a metal, or a radionuclide. In some embodiments, the detecting is by flow cytometry.

In yet another aspect, the present invention provides a kit for determining the presence or absence of complement fixing antibodies in a biological sample from a subject that bind specifically to an antigen of interest, including a solid substrate with an antigen of interest (AgI) immobilized thereon; a detectably labeled ligand capable of specifically binding to complement factor C1q; and instructions for determining the presence or absence of complement fixing antibodies in a biological sample from a subject against the antigen of interest.

In some embodiments, the solid substrate is a multiwell plate. In other embodiments, the solid substrate is a membrane. In yet other embodiments, the solid substrate is a microparticle, such as an agarose bead, a polystyrene bead, a latex bead, or a magnetic bead. In some embodiments, the solid substrate is a cell. In other embodiments, the solid substrate is a cell membrane. In some embodiments, the biological sample is serum, blood, saliva, plasma, or urine. In some embodiments, the detectably labeled ligand is a detectably labeled antibody or binding fragment thereof. In some embodiments, the detectable label is a fluorochrome, a chromophore, an enzyme, a linker molecule, a biotin molecule, an electron donor, an electron acceptor, a dye, a metal, or a radionuclide.

In yet another aspect, the present invention provides a kit for determining the presence or absence of complement fixing antibodies in a biological sample from a subject that bind specifically to an antigen of interest, including a solid substrate with an antigen of interest (AgI) immobilized thereon; a directly labeled exogenous C1q capable of binding to complement fixing antibodies; and instructions for determining the presence or absence of complement fixing antibodies in a biological sample from a subject against the antigen of interest.

In some embodiments, the solid substrate is a multiwell plate. In other embodiments, the solid substrate is a membrane or a cell. In yet other embodiments, the solid substrate is a microparticle, such as an agarose bead, a polystyrene bead, a latex bead, or a magnetic bead. In other embodiments, the solid substrate is a cell membrane. In some embodiments, the biological sample is serum, blood, saliva, plasma, or urine. In some embodiments, the directly labeled exogenous C1q is labeled with a fluorochrome, a chromophore, an enzyme, a linker molecule, a biotin molecule, an electron donor, an electron acceptor, a dye, a metal, or a radionuclide.

In yet another aspect, the present invention provides a kit for determining the presence or absence of complement fixing antibodies in a biological sample from a subject against human leukocyte antigens (HLAs), including a collection of microparticle subtypes wherein each microparticle subtype is coated with different purified HLAs to represent the HLA antigen population of a single cell line or multiple cell lines such that the collection simulates the distribution of HLAs in a normal human population; a detectably labeled ligand capable of specifically binding with a complement factor C1q; and instructions for determining the presence or absence of complement fixing antibodies in a sample from a subject against HLAs.

In some embodiments, the microparticle is an agarose bead, a latex bead, a magnetic bead, or a polystyrene bead. In some embodiments, the biological sample is serum, blood, saliva, plasma, or urine. In some embodiments, the detectably labeled ligand is a detectably labeled antibody or binding fragment thereof. In some embodiments, the detectable label is a fluorochrome, a chromophore, an enzyme, a linker molecule, a biotin, an electron donor, an electron acceptor, a dye, a metal, or a radionuclide.

In yet another aspect, the present invention provides a kit for determining the presence or absence of complement fixing antibodies in a biological sample from a subject against human leukocyte antigens (HLAs), including a collection of microparticle subtypes wherein each microparticle subtype is coated with different purified HLAs to represent the HLA antigen population of a single cell line or multiple cell lines such that the collection simulates the distribution of HLAs in a normal human population; a directly labeled exogenous C1q capable of binding to complement fixing antibodies; and instructions for determining the presence or absence of complement fixing antibodies in a sample from a subject against HLAs.

In some embodiments, the microparticle is an agarose bead, a latex bead, a magnetic bead, or a polystyrene bead. In some embodiments, the biological sample is serum, blood, saliva, plasma, or urine. In some embodiments, the directly labeled exogenous C1q is labeled with a fluorochrome, a chromophore, an enzyme, a linker molecule, a biotin, an electron donor, an electron acceptor, a dye, a metal, or a radionuclide.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 7 shows a comparison of ability of one-step vs two step C1q procedure to define expected antibodies.

FIG. 10 shows a comparison of the complement-dependent cytotoxic (CDC) assay and C1q assays for determination of inhibition by IVIG. The CDC assay is the only assay previously available for this determination.

FIGS. 12A-12B show a comparison of the LMX-C1q (FIG. 12A) and LMX-IgG (FIG. 12B) assays in the monitoring change in A24 antibody of Adult Heart patient's serum with each subsequent treatment. (Same patient as FIG. 11).

FIG. 16A-N is a table showing the results of the C1Q validation experiment.

FIG. 17A-J is a table showing the results of the C1Q-IVIG validation experiment.

FIG. 19A-B provide a comparison between direct and indirect labeling of C1q using an LMX-C1q assay.

FIG. 20A-B provide a comparison between indirect labeling of C1q in an in vitro LMX-C1q IVIG inhibition assay (FIG. 20A) and direct labeling of C1q in an in vitro LMX-C1q IVIG inhibition assay (FIG. 20B).

DEFINITIONS

Figure 1:
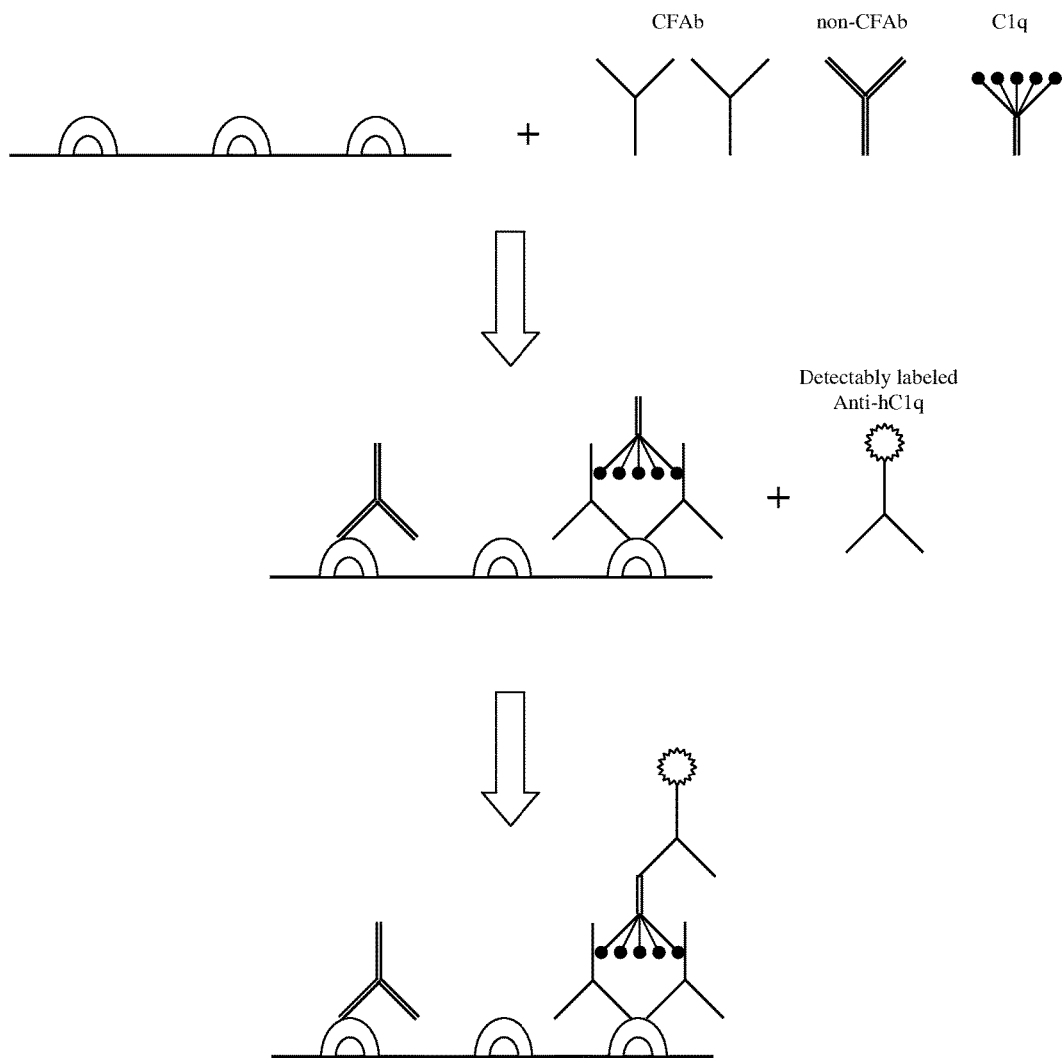
FIG. 1 provides a general schematic of one embodiment of the present disclosure. A solid substrate having an antigen or individually distinguishable antigens of interest (AgI) immobilized thereon is contacted with a biological sample suspected of containing anti-AgI complement fixing antibodies (CFAb). As shown in the figures, the sample will also likely include non-complement fixing antibodies (non-CFAb) as well as autologous and/or exogenous C1q that binds specifically to complement fixing antibodies in the same sample. Following incubation, if present, the anti-AgI complement fixing antibodies bind specifically to the immobilized AgI and the C1q binds specifically to the bound anti-AgI complement fixing antibodies. The solid substrate is contacted with detectably labeled anti-human C1q (anti-hC1q) antibodies that bind specifically to human C1q. The presence of the detectable label is then assayed using methods known in the art.

The term "complement fixing antibody" refers to an antibody that binds specifically to an antigen on a pathogen and initiates the complement cascade of the immune system that provides for clearance of the antigen bearing target (e.g., cell) or pathogen from the organism. In general, a complement fixing antibody is an IgM or an IgG antibody that is recognized and specifically bound by complement factor C1q.

The C1q complement factor is a subunit of the C1 enzyme complex that activates the serum complement system. It is composed of 9 disulfide-linked dimers of the chains A, B and C, which share a common structure consisting of an N-terminal non-helical region, a triple helical (collagenous) region, and a C-terminal globular head (Smith et al. Biochem. J. 1994. 301:249-256). C1q is involved in host defense, inflammation, apoptosis, autoimmunity, cell differentiation, organogenesis, hibernation and insulin-resistant obesity. Five strictly conserved residues have been identified in the C1q family (Kishore et al. Trends in Immunology 2004. 25(10):551-561). Each C1q domain exhibits a ten-stranded-sandwich fold with a jelly-roll topology, consisting of two five-stranded β-sheets (A', A, H, C, F) and (B', B, G, D, E), each made of antiparallel strands. In general, the C1q complement factor is present in the serum of animals and has both binding specificity and binding affinity for complement fixing antibodies, which are also present in the serum of the animal. Binding of C1q complement factor to complement fixing antibodies activates the complement cascade of the immune system.

By "autologous" is meant derived from the same patient sample as another element. For example, in reference to autologous C1q is meant that the C1q occurs in the same subject sample as the complement fixing antibodies.

By "exogenous" is meant an element that is not naturally derived from a particular organism. For example, in reference to exogenous C1q, it is meant that the C1q is derived from an organism or system different from the subject sample having the complement fixing antibodies.

An "affinity reagent" of the subject invention has an analyte binding domain, moiety, or component that has a high binding affinity for a target analyte. By high binding affinity is meant a binding affinity of at least about $10^{-4}$ M, usually at least about $10^{-6}$ M or higher, e.g., $10^{-9}$M or higher. The affinity reagent may be any of a variety of different types of molecules, so long as it exhibits the requisite binding affinity for the target protein when present as tagged affinity ligand.

As such, the affinity reagent may be a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand in size from about 10,000 daltons or greater in molecular weight.

Of particular interest as large molecule affinity ligands are antibodies, as well as binding fragments and mimetics thereof. Where antibodies are the affinity ligand, they may be derived from polyclonal compositions, such that a heterogeneous population of antibodies differing by specificity are each tagged with the same tag nucleic acid, or monoclonal compositions, in which a homogeneous population of identical antibodies that have the same specificity for the target protein are each tagged with the same tag (e.g., fluorophore). As such, the affinity ligand may be a monoclonal, oligoclonal, and/or polyclonal antibody. In yet other embodiments, the affinity ligand is an antibody binding fragment or mimetic, where these fragments and mimetics have the requisite binding affinity for the target protein. For example, antibody fragments, such as Fv, (Fab')$_2$, and Fab may be prepared by cleavage of the intact protein, e.g. by protease or chemical cleavage. Also of interest are recombinantly produced antibody fragments, such as single chain antibodies or scFvs, where such recombinantly produced antibody fragments retain the binding characteristics of the above antibodies. Such recombinantly produced antibody fragments generally include at least the VH and VL domains of the subject antibodies, so as to retain the binding characteristics of the subject antibodies. These recombinantly produced antibody fragments or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments and mimetics thereof may be obtained from commercial sources and/or prepared using any convenient technology, where methods of producing polyclonal antibodies, oligoclonal antibodies, monoclonal antibodies, fragments and mimetics thereof, including recombinant derivatives thereof, are known to those of the skill in the art.

By "epitope" is meant a site on an antigen to which specific B cells and T cells respond. The term is also used interchangeably with "antigenic determinant" or "antigenic determinant site." An epitope can comprise 1 or more amino acids, such as three or more amino acids, in a spatial conformation unique to the epitope. Generally, an epitope includes at least 5 such amino acids and, more usually, consists of at least 8-10 such amino acids. Methods of determining spatial conformation of amino acids are known in the art and include, for example, X-ray crystallography and 2-dimensional nuclear magnetic resonance. Furthermore, the identification of epitopes in a given protein is readily accomplished using techniques well known in the art. See, e.g., Geysen et al., Proc. Natl. Acad. Sci. USA (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., Molecular Immunology (1986) 23:709-715 (technique for identifying peptides with high affinity for a given antibody). Antibodies that recognize the same epitope can be identified in a simple immunoassay showing the ability of one antibody to block the binding of another antibody to a target antigen.

By "binds specifically" or "specifically binds" is meant high avidity and/or high affinity binding of an antibody to a specific antigen. Antibody binding to its epitope on a specific antigen is with a greater avidity and/or affinity than binding of the same antibody to different epitopes, particularly different epitopes that may be present in molecules in association with, or in the same sample, as a specific antigen of interest. Complement fixing antibodies may, however, have the same or similar avidity and/or affinity for various epitopes on different antigens of interest. As such, "binds specifically" or "specifically binds" is not meant to preclude a given complement fixing antibody from binding to more than one antigen of interest. Antibodies that bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g., by use of appropriate controls.

By "detectably labeled ligand", or "detectably labeled secondary ligand" is meant a ligand having an attached detectable label, where the ligand is capable of binding specifically to another compound. Examples of ligands include, but are not limited to, and antibody or an antibody fragment that retains binding specificity. The detectable label may be attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, chromophores, fluorophores, fluorochromes, enzymes (e.g., horseradish peroxidase), linker molecules or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled secondary antibodies to detect an antigen are well known in the art. [Note: See, e.g., Harlow and Lane, eds. (Antibodies: A Laboratory Manual (1988) Cold Spring Harbor Laboratory Press, Cold Spring Harbor, N.Y.)]

By "directly labeled C1q" is meant an exogenous C1q molecule having an attached detectable label. The detectable label may be attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, chromophores, fluorophores, enzymes (e.g., horseradish peroxidase), linker molecules or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled secondary antibodies to detect an antigen are well known in the art. [Note: See, e.g., Harlow and Lane, eds. (Antibodies: A Laboratory Manual (1988) Cold Spring Harbor Laboratory Press, Cold Spring Harbor, N.Y.)]

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which compound is unaccompanied by at least some of the material with which it is normally associated in its natural state. For example, the term "isolated" with respect to a polypeptide generally refers to an amino acid molecule devoid, in whole or part, of sequences normally associated with it in nature; or a sequence, as it exists in nature, but having heterologous sequences in association therewith.

"Purified" as used herein means that the recited material comprises at least about 75% by weight of the total protein, with at least about 80% being preferred, and at least about 90% being particularly preferred. As used herein, the term "substantially pure" refers to a compound that is removed from its natural environment and is at least 60% free, preferably 75% free, and most preferably 90% free from other components with which it is naturally associated.

As used herein, a "biological sample" refers to a sample of tissue or fluid isolated from a subject, which in the context of the invention generally refers to samples suspected of containing anti-AgI complement fixing antibodies, which samples, after optional processing, can be analyzed in an in vitro assay. Typical samples of interest include, but are not necessarily limited to, blood, plasma, serum, blood cells, urine, saliva, and mucous. Samples also include samples of in vitro cell culture constituents including but not limited to conditioned media resulting from the growth of cells and tissues in culture medium, e.g., recombinant cells, and cell components.

As used herein the terms "Human Leukocyte Antigen system" or "HLA" refers to the major histocompatibility complex, which spans approximately 3.5 million base pairs on the short arm of chromosome 6. It is divisible into 3 separate regions which contain the class I, the class II and the class III genes. In humans, the class I HLA complex is about 2000 kb long and contains about 20 genes. Within the class I region exist genes encoding the well characterized class I MHC molecules designated HLA-A, HLA-B and HLA-C. In addition, there are nonclassical class I genes that include HLA-E, HLA-F, HLA-G, HLA-H, HLA-J and HLA-X as well as a new family known as MIC. The class II region contains three genes known as the HLA-DP, HLA-DQ and HLA-DR loci. These genes encode the α and β chains of the classical class II MHC molecules designated HLA-DR, DP and DQ. In humans, nonclassical genes designated DM, DN and DO have also been identified within class II. The class III region contains a heterogeneous collection of more than 36 genes.

A "purified HLA subtype" as used herein refers to a substantially purified antigen of an HLA subtype as described in the table below. When used in reference to a microbead coated with "a different HLA subtype" it is meant that each population of a microbead is coated with a different HLA antigen subtype.

An "HLA antigen population" as used herein refers to a specific population of HLA antigens found in any one collections, that may be naturally occurring or non-naturally occurring, such as in a specific cell or tissue type.

As used herein "the distribution of HLAs in a normal human population" refers to a specific population of HLA antigens found in a normal human population, such as in a specific cell or tissue type or an individual.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

The term "solid substrate" refers to a solid support in which antigens and/or antibodies may be immobilized thereon. Exemplary solid substrates include multiwell plates, membranes including nitrocellulose membranes and polyethylene membranes, cell and cell membranes, beads, microparticles, microspheres and microbeads. The methods of the invention may be carried out with microparticles, microspheres, microbeads, or beads of any material, e.g. silica, gold, latex, polymers such as polystyrene, polysulfone, polyethyl, or hydrogel. In addition, the microparticles, microspheres, beads or microbeads may be a magnetic.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

The invention provides methods for sensitive and specific detection of complement fixing antibodies in a biological sample using complement factor C1q, including autologous complement factor C1q present in the biological sample and a detectably labeled antibody that binds the autologous complement factor C1q, exogenous human complement factor C1q and a detectably labeled antibody that binds the exogenous human complement factor C1q, detectably labeled exogenous human complement factor C1q, or a combination of autologous complement factor C1q and exogenous human complement factor C1q. The invention also features kits, systems, and devices for use in the methods of the invention.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Detection Methods

As summarized above, the subject invention provides a method of determining the presence or absence of complement fixing antibodies in a biological sample. The methods of the subject invention utilize complement factor C1q (e.g. autologous, or exogenous) to identify the complement fixing antibodies present in the same biological sample that bind specifically to an antigen of interest.

The methods generally include contacting a solid phase support having an antigen of interest (AgI) immobilized thereon with a biological sample suspected of containing complement fixing antibodies that bind specifically to the antigen of interest. If present, the complement fixing antibody will bind specifically to the immobilized antigen on the solid phase support, and C1q will bind to the complement fixing antibody. C1q binding can then be assayed by contacting the solid phase support with a detectably labeled anti-C1q antibody that binds specifically to the bound C1q. Alternatively, directly labeled C1q can be used in the assay, and binding of this directly labeled C1q can be measured directly, without the use of a detectably labeled anti-C1q antibody.

The biological sample will generally include non-complement fixing antibodies as well as complement fixing antibodies. One advantage of the present invention is that it can differentiate between the two different antibodies, either by using C1q present in the same sample, or by using exogenous C1q. By using C1q present in the same sample, the assay provides for sensitive and specific detection of the relevant complement fixing antibodies that would not occur if a xenogeneic C1q were used, such as one derived from rabbit serum.

As will be readily apparent, design of the assays described herein is subject to a great deal of variation, and many formats are known in the art. The following descriptions are merely provided as guidance and one of skill in the art can readily modify the described protocols, using techniques well known in the art.

Antigen of Interest (AgI)

An antigen or antigenic determinant capable of eliciting an antibody is suitable for use in the present invention. Such antigens or antigenic determinants can be, for example, those derived from normal human [e.g., human leukocyte antigens (HLA)], bacterial, viral, parasitic, or fungal sources, or abnormal tissues, such as tumor antigens. An antigen is generally any molecule toward which an antibody can be generated, including molecules which require the presence of an adjuvant or conjugation to another molecule to induce antibody formation. An antigen may be a peptide or protein, a carbohydrate, a nucleic acid, or a lipid. The term "antigen" also includes portions of naturally occurring molecules, such as, for example, a subunit of a protein, or a fragment of a protein containing a functional domain or biologically relevant motif. Suitable antigens include but are not limited to proteins associated with the cell cycle, tissue-specific proteins, tumor markers, cytokines, major histocompatability complex proteins, heat shock proteins, and pathogen-associated proteins (where a pathogen may be a bacterium, a virus, a fungus, a protozoan, a multicellular parasite, or a prion), as well as carbohydrate residues associated with blood transfusion antigens and tissue typing, lipopolysaccharides, sphingolipids, etc. Exemplary antigens are those that elicit an immune response that protects an animal from disease. Examples of such antigens include, but are not limited to, a protozoan parasite antigen, a helminth parasite antigen, an ectoparasite antigen, a fungal antigen, a bacterial antigen, and a viral antigen.

Examples of viral antigens include antigens derived from viruses such as the hepatitis B virus (HBV), human immunodeficiency virus (HIV), influenza A virus, Epstein Barr virus (EBV), herpes simplex virus (HSV), respiratory syncytial virus (RSV), human cytomegalovirus (HCMV), varicella zoster virus (VZV), and measles virus. Examples of bacterial antigens include, but are not limited to, antigens from Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia. Examples of fungal antigens include, but are not limited to, antigens from Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha. Example of protozoan and helminth parasite antigens include, but are not limited to, antigens from Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris. Uncinaria, and Wuchereria. Examples of ectoparasite antigens include, but are not limited to, antigens (including protective antigens as well as allergens) from fleas; ticks, including hard ticks and soft ticks; flies, such as midges, mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs.

Exemplary antigens include, but are not limited to, a calicivirus antigen, a coronavirus antigen, a herpesvirus antigen, an immunodeficiency virus antigen, an infectious peritonitis virus antigen, a leukemia virus antigen, a pan-leukopenia virus antigen, a parvovirus antigen, a rabies virus antigen, a Bartonella antigen, a Yersinia antigen, a Dirofilaria antigen, a Toxoplasma antigen, a tumor antigen, a flea antigen, a flea allergen, a midge antigen, a midge allergen, a mite antigen, and a mite allergen. Particularly preferred antigens include a rabies virus glycoprotein G antigen; heartworm PLA2, P39, P4, P22U, Gp29, astacin, cysteine protease, macrophage migration inhibitory factor, venom allergen, TPX-1, TPX-2, transglutaminase, ankyrin, and asparaginase antigens; flea serine protease, cysteine protease, aminopeptidase, serpin, carboxylesterase, juvenile hormone esterase, and epoxide hydrolase antigens; flea salivary antigens; Yersinia F1 and V antigens; and Toxoplasma gondii antigens.

The antigen used in the present invention may be that which is produced by a gene recombination method or is chemically synthesized on the basis of gene sequence or peptide sequence determined by gene recombination. Thus, it is a recombinant antigen which is prepared by such a manner that already-known genome sequence or DNA sequence obtained by a molecular cloning from natural virus or cell by utilization of gene recombination techniques is treated with enzymes or the like or subjected to chemical synthesis and the resulting DNA sequence or modified DNA sequence is expressed by a microbe, animal, plant, insect or the like to give a recombinant antigen or it is a peptide or a modified peptide which is prepared by means of a peptide chemical synthesis known as a liquid phase method or a solid phase method utilizing the above information. A solid phase synthetic method for peptide may be usually carried out by an automated peptide synthetic apparatus in an advantageous manner.

Preabsorption

In some embodiments, the biological sample is optionally first contacted with a cross-reactive antigen. In general, contacting the biological sample with a cross-reactive antigen will result in depletion of cross-reactive antibodies in a biological sample while also not depleting anti-AgI (antigen of interest) specific complement fixing antibodies, which if present, remains in the sample at detectable levels (e.g., by use of an assay to detect specific anti-AgI specific complement fixing antibodies as described herein). Therefore, the cross-reactive antigen used to contact the biological sample will generally not comprise the AgI that will be used to detect the presence or absence of anti-AgI specific complement fixing antibodies in the preabsorbed biological sample.

Contacting can be accomplished by, for example, contacting the biological sample with one or more cross-reactive antigens as described herein. The biological sample can be contacted with the cross-reactive antigen and then the specific solid support with immobilized AgI in sequential steps. In some embodiments, the biological sample is contacted with a cross-reactive antigen according to the invention to "preabsorb" non-specific antibodies from the sample prior to detection of specific anti-AgI specific complement fixing antibodies in the sample. Unless specifically indicated otherwise, "preabsorbtion" as used herein does not necessarily imply that the biological sample is contacted with the cross-reactive antigen first, followed by contacting the sample with an AgI, but rather means that specific anti-AgI specific complement fixing antibodies are not detected until after the sample has been exposed to the cross-reactive antigen.

Sample Preparation

In practicing the subject methods, a sample from a subject is assayed for the presence of anti-AgI specific complement fixing antibodies. In some embodiments, the sample that is assayed is a sample that is, or is derived from, any initial source that contains complement fixing antibodies that specifically bind to an AgI. In other embodiments, the sample is, or is obtained from, any initial source containing insufficient complement. Such samples include those in which the complement or C1q has been destroyed by heat inactivation, and those in which the C1q is supplied exogenously. Accordingly, a suitable sample source will be derived from fluids into which the complement fixing antibodies that specifically bind to an AgI have been released. Sample sources of interest include, but are not limited to, many different bodily fluids, particularly blood or blood products, e.g., serum, plasma, and whole blood, blood cells, and urine. The sample volume can be any volume that is compatible with the specific assay format. In some embodiments, the sample will be diluted in a suitable solution prior to assaying for the presence or absence of complement fixing antibodies that specifically bind to an AgI. In general, a solution suitable for diluting a biological sample will include a buffer, such as phosphate buffered saline (PBS), and may include additional items, such as, for example, a non-specific blocking agent, such as bovine serum albumin (BSA), a detergent, such as Triton-X-100, and the like.

Appropriate control samples for the assay include, but are not limited to, blood, serum, whole blood, or urine collected from human subjects who do not have anti-AgI specific complement fixing antibodies (i.e., negative control), or samples which contain a known, predetermined amount of anti-AgI specific complement fixing antibodies (i.e., a positive control).

In many embodiments, a suitable initial source for the human sample is a blood sample. As such, the sample employed in the subject assays is generally a blood-derived sample. The blood-derived sample may be derived from whole blood or a fraction thereof, e.g., serum, plasma, etc., where in some embodiments the sample is derived from blood allowed to clot and the serum separated and collected to be used to assay.

In embodiments in which the sample is plasma, serum, or a serum-derived sample, the sample is generally a fluid sample. Any convenient methodology for producing a fluid serum sample may be employed. In many embodiments, the method employs drawing venous blood by skin puncture (e.g., finger stick, venipuncture) into a clotting or serum separator tube, allowing the blood to clot, and centrifuging the serum away from the clotted blood. The serum is then collected and stored until assayed. Similarly, a plasma sample can be collected from the patient by drawing venous blood into a tube and centrifuging the blood so that the blood cells collect at the bottom of the tube. The liquid portion of the sample, which is blood plasma, can then be collected and stored until assayed. Once the patient-derived sample is obtained, the sample is assayed to determine the presence of anti-AgI specific complement fixing antibodies.

The subject sample may be treated in a variety of ways so as to enhance detection of the presence of anti-AgI specific complement fixing antibodies. For example, where the sample is blood, the red blood cells may be removed from the sample (e.g., by centrifugation) prior to assaying. Detection of the presence of anti-AgI specific complement fixing antibodies may also be enhanced by concentrating the sample using procedures well known in the art (e.g. acid precipitation, alcohol precipitation, salt precipitation, hydrophobic precipitation, filtration (using a filter which is capable of retaining molecules greater than 30 kD, e.g. Centrim 30™), affinity purification).

Assay Formats

Figure 2:
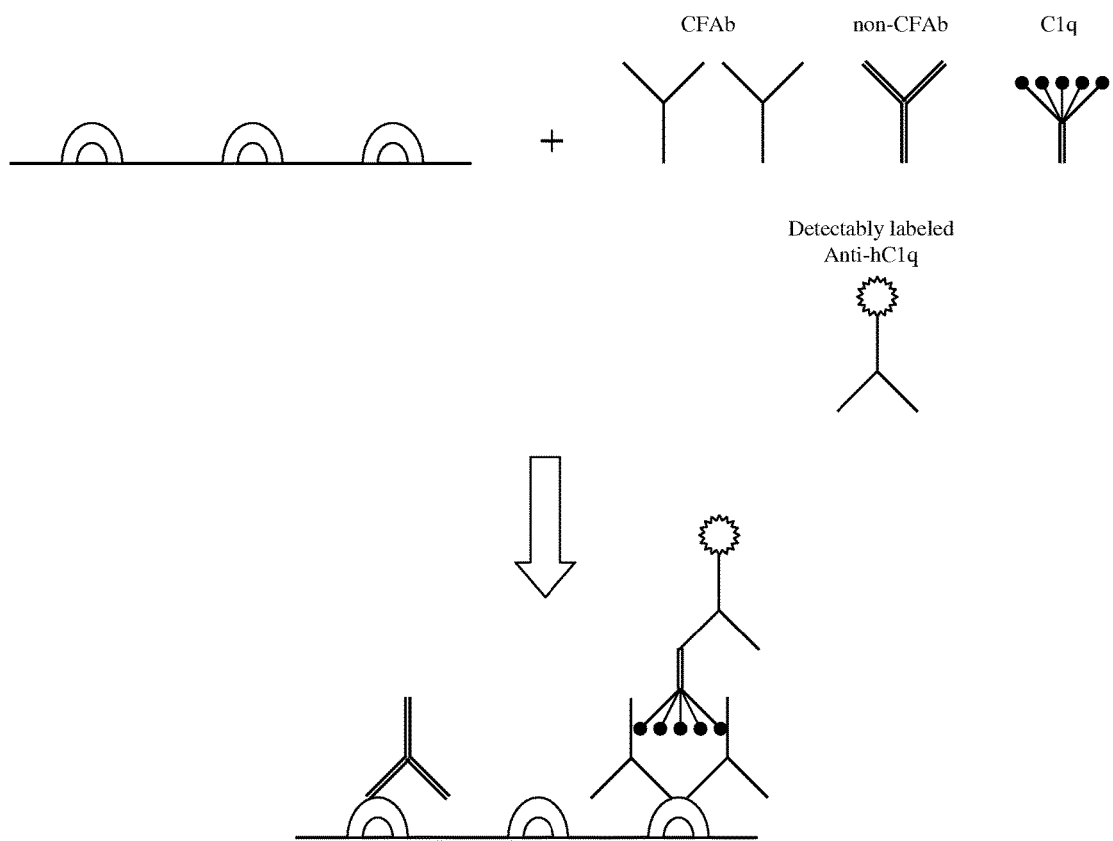
FIG. 2 provides a general schematic of another embodiment of the present disclosure. In this embodiment, the detectably labeled anti-C1q (anti-hC1q) antibodies are added directly to the biological sample before the solid substrate is contacted with the sample. Alternatively, the anti-hC1q antibodies and the biological sample can be introduced to the solid substrate at the same time.
Figure 3:
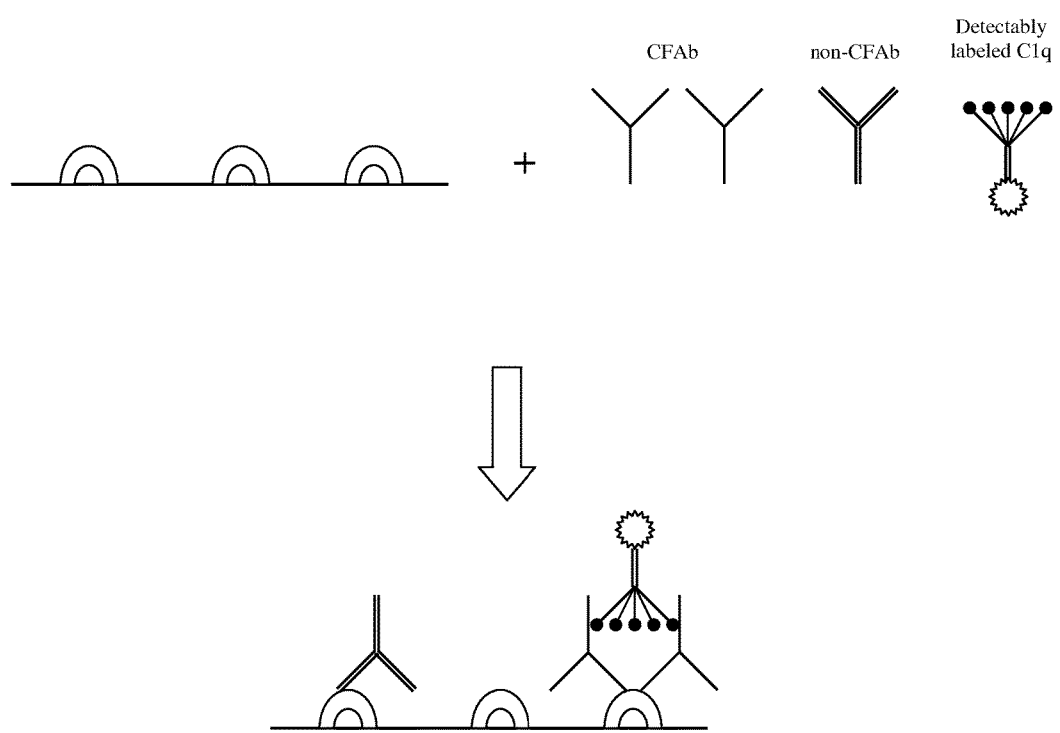
FIG. 3 provides a general schematic of another embodiment of the present disclosure. In this embodiment, detectably labeled exogenous C1q is added directly to the biological sample before the solid substrate is contacted with the sample. Alternatively, the detectably labeled exogenous C1q and the biological sample can be introduced to the solid substrate at the same time, or the detectably labeled exogenous C1q can be introduced to the solid substrate after the biological sample has been introduced to the substrate. In this embodiment, as with other embodiments, the presence of the detectably labeled exogenous C1q is assayed using methods known in the art.
Figure 4:
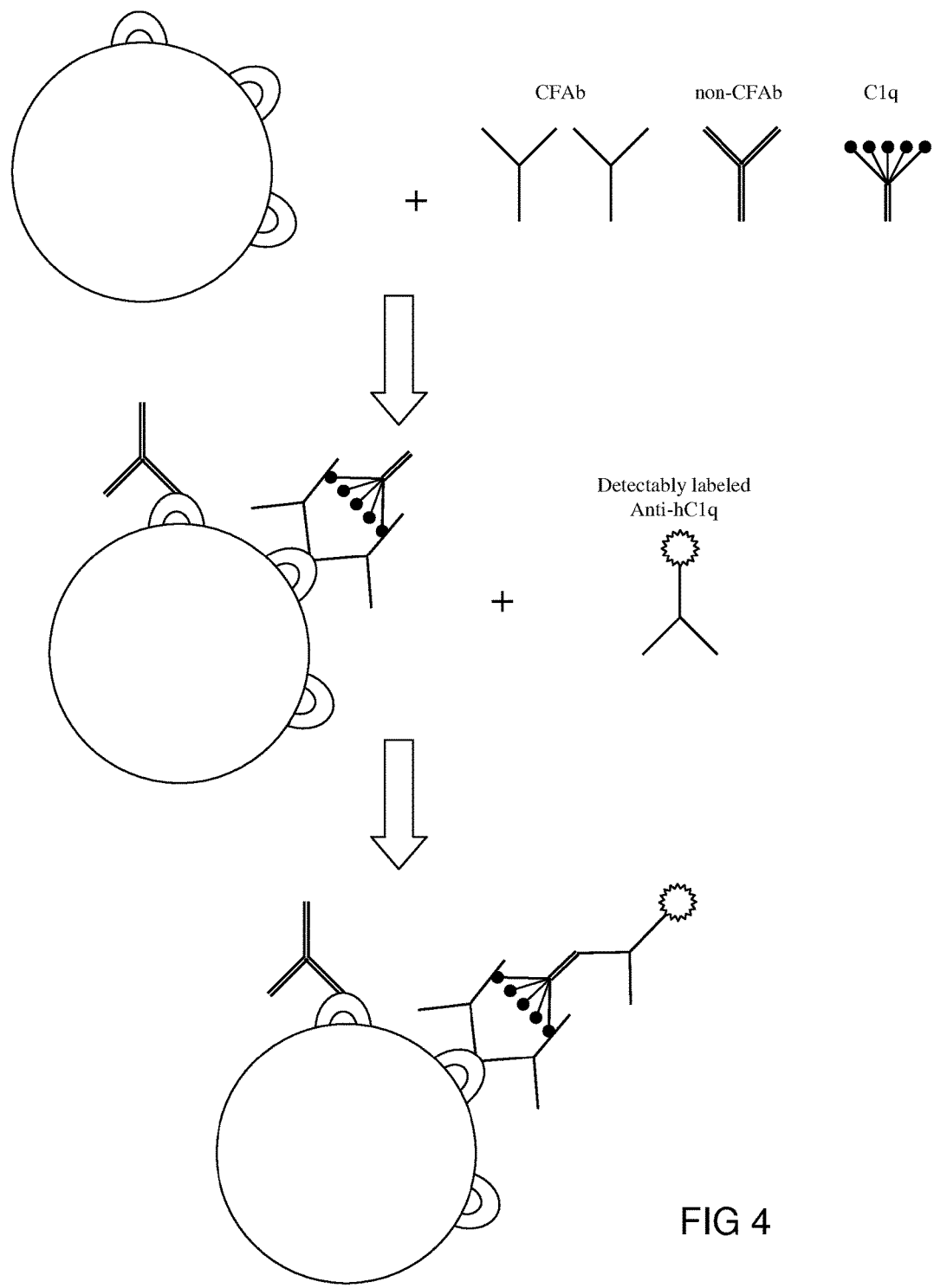
FIG. 4 provides a general schematic of another embodiment of the present disclosure. This embodiment is similar to the embodiment described in FIG. 1, and functions in a similar manner. In this embodiment, however, the solid substrate having an antigen or individually distinguishable antigens of interest (AgI) immobilized thereon is a bead, microbead, microsphere, microparticle, cell or membrane.
Figure 5:
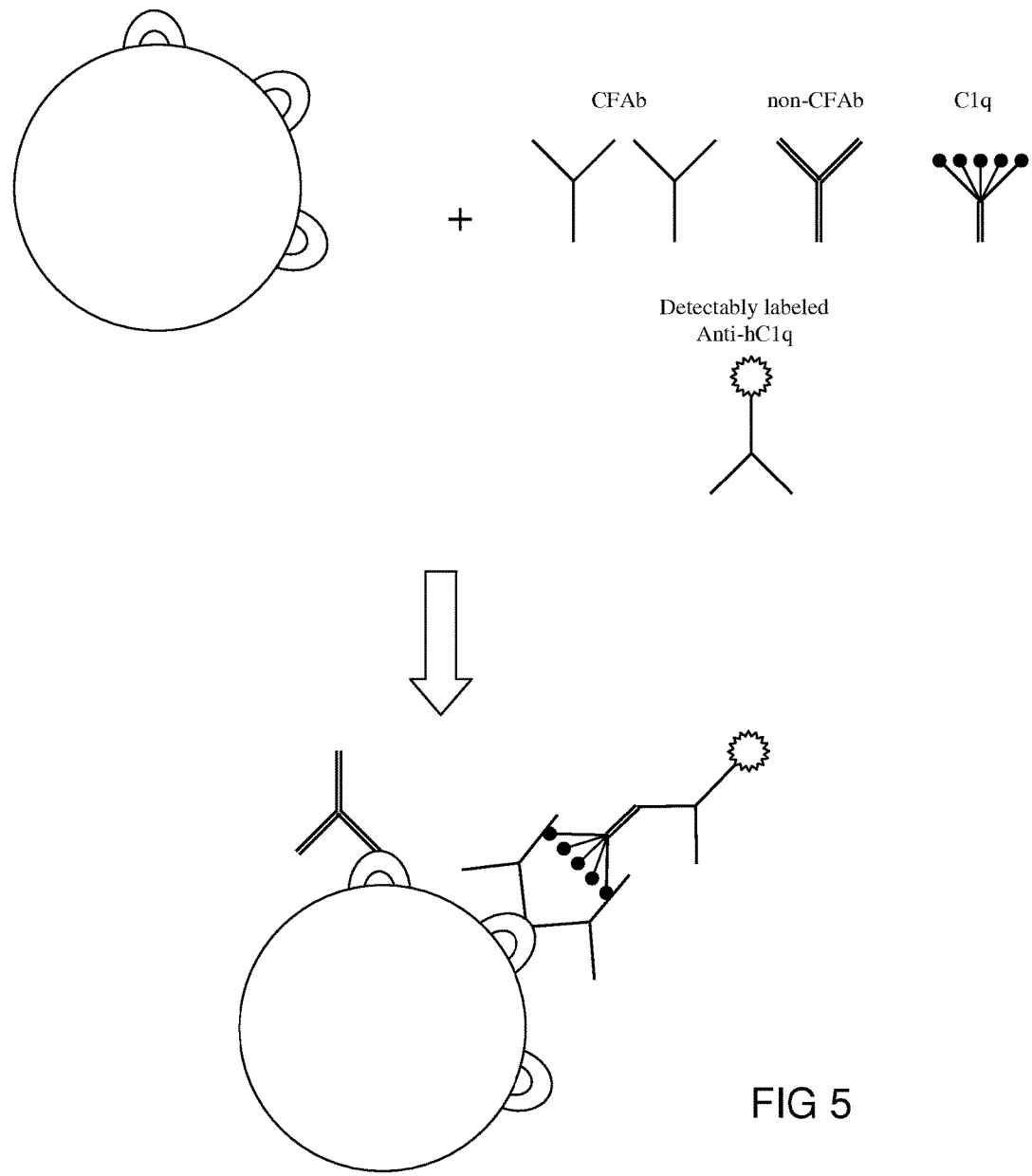
FIG. 5 provides a schematic of another embodiment of the present disclosure. This embodiment is similar to the embodiment described in FIG. 2, and functions in a similar manner. In this embodiment, however, the solid substrate having an antigen or individually distinguishable antigens of interest (AgI) immobilized thereon is a bead, microbead, microsphere, microparticle, cell or membrane.
Figure 6:
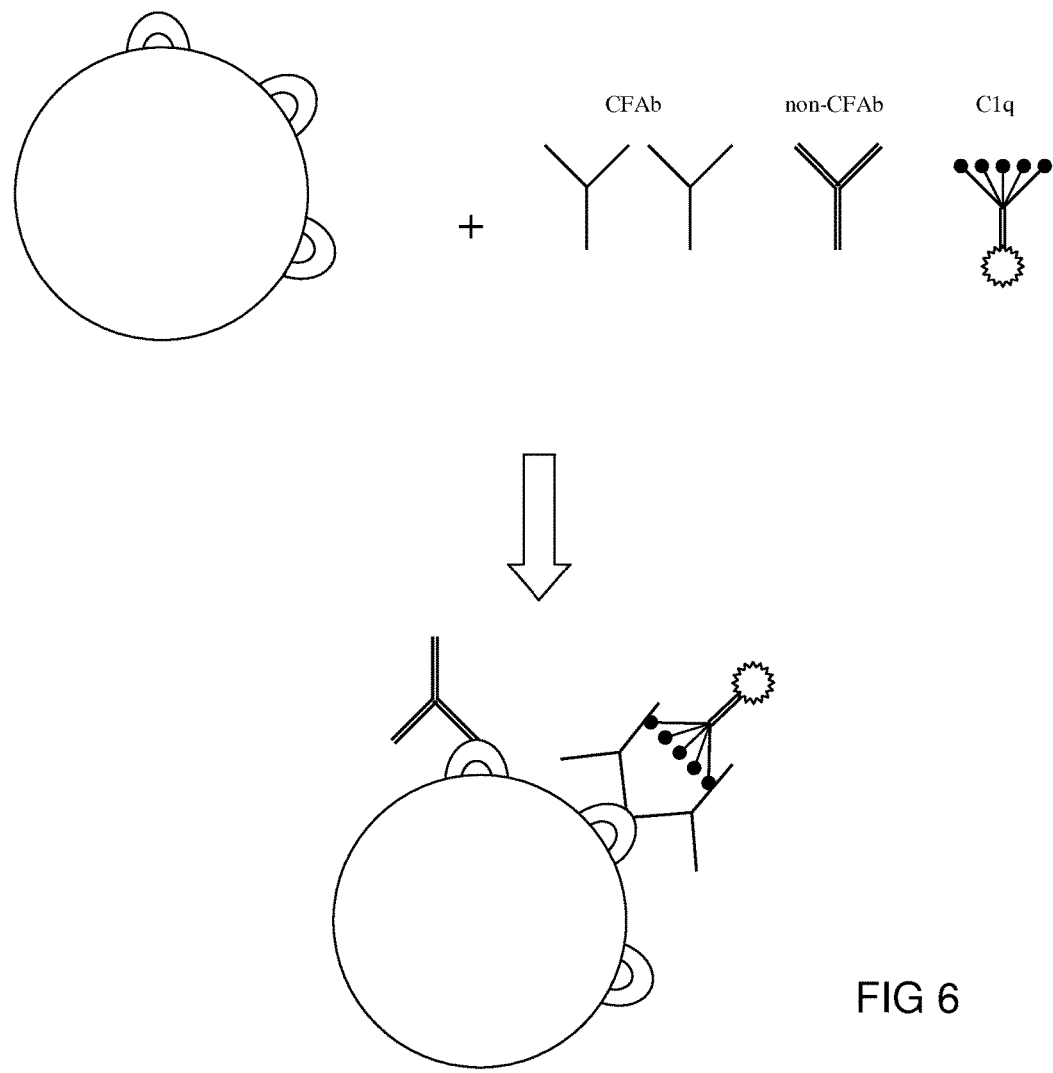
FIG. 6 provides a schematic of another embodiment of the present disclosure. This embodiment is similar to the embodiment described in FIG. 3, and functions in a similar manner. In this embodiment, however, the solid substrate having an antigen or individually distinguishable antigens of interest (AgI) immobilized thereon is a bead, microbead, microsphere, microparticle, cell or membrane.

The solid support immobilized AgIs are used herein as diagnostics to detect the presence or absence of reactive anti-AgI specific complement fixing antibodies in a biological sample. Typically, the assays generally involve separation of unbound antibody in a liquid phase from a solid phase support to which antigen-complement fixing antibody complexes are bound. The assay is generally described in FIG. 1, FIG. 2, and FIG. 3 with respect to a substantially flat solid support (e.g., membrane or microtiter well form) and in FIG. 4, FIG. 5, and FIG. 6 with respect to a microbead solid support. Solid supports which can be used in the practice of the invention include substrates such as nitrocellulose (e.g., in membrane or microtiter well form); polyvinylchloride (e.g., sheets or microtiter wells); polystyrene; latex (e.g., beads, microbeads, microparticles, microspheres or microtiter plates); polyvinylidine fluoride; diazotized paper; nylon membranes; polyethylene membranes, activated beads, magnetically responsive beads, cells, and cell membranes, and the like.

In some embodiments, the biological sample will be diluted in a suitable solution prior to assaying. In general, a solution suitable for diluting a biological sample will include a buffer, such as phosphate buffered saline (PBS), and may include additional items, such as, for example, a non-specific blocking agent, such as bovine serum albumin (BSA), a detergent, such as Triton-X-100, and the like.

In general, a solid support is first reacted with a liquid phase component (e.g., one or more specific antigens of interest (AgI)) under suitable binding conditions such that the component is sufficiently immobilized to the support. Optionally, immobilization of the antigen to the support can be enhanced by first coupling the AgI to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the AgI, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After contacting the solid support with the AgI, any non-immobilized AgI is removed from the support by washing. The support-bound AgI is then contacted with a biological sample suspected of containing anti-AgI complement fixing antibodies under suitable binding conditions. If present, the complement fixing antibodies will bind specifically to the immobilized AgI. C1q (e.g. autologous, or exogenous) present in the sample will bind to the complement fixing antibody bound to the AgI immobilized on the solid phase support. The C1q present in the sample may be autologous C1q from the biological sample itself, or may be exogenous C1q. In some embodiments, the bound C1q is then assayed by contacting the solid phase support with a detectably labeled anti-C1q antibody that binds specifically to the C1q. The presence of the detectably labeled anti-C1q antibody can then be detected using techniques well known in the art.

In some embodiments, the assay is carried out in a sequential manner, first contacting the solid phase support with the biological sample containing anti-AgI complement fixing antibodies and C1q, and then contacting the solid phase support with a detectably labeled anti-C1q antibody. This approach is described in FIG. 1. In other embodiments, the solid phase support is contacted with both the biological sample and the detectably labeled anti-C1q antibody at the same time. This approach is described in FIG. 2.

In some embodiments, detectably labeled exogenous C1q is used in the assay. In such embodiments, the solid phase support is contacted with both the sample of interest and the detectably labeled exogenous C1q at the same time. Bound C1q is then detected using techniques well known in the art. This approach is described in FIG. 3.

More particularly, in some embodiments, an ELISA method can be used, wherein the wells of a microtiter plate are coated with specific AgI (e.g., the specific AgI are immobilized on the surface). A sample containing or suspected of containing anti-AgI complement fixing antibodies and C1q (e.g. autologous, or exogenous) is then added to the coated wells. Optionally, a series of standards, containing known concentrations of anti-AgI complement fixing antibodies can be assayed in parallel with the samples or aliquots thereof to serve as controls. Generally from about 0.001 to 1 ml of sample, diluted or otherwise, is sufficient, usually about 0.01 ml sufficing. Furthermore, in certain embodiments, each sample and standard will be added to multiple wells so that mean values can be obtained for each. The test and control samples are each incubated with the solid support for a time sufficient for binding of an antibody to antigen to occur. Generally, from about 0.1 to 3 hour is sufficient, usually 1 hour sufficing.

After a period of incubation sufficient to allow antibody binding to the immobilized AgI and binding of C1q present in the sample to the complement fixing antibody bound to the immobilized AgI, the plate(s) can optionally be washed to remove unbound antibodies. Generally, a dilute non-ionic detergent medium at an appropriate pH, generally 7-8, can be used as a wash medium. An isotonic buffer, such as phosphate-buffered saline, may be employed in the washing step. In certain embodiments, no wash will be performed during the assay.

In an alternative embodiment, a biological sample containing or suspected of containing anti-AgI complement fixing antibodies is first contacted with cross-reactive antigen in a solution to provide a preabsorbed mixture. After a period of incubation sufficient to allow antibody binding to the cross-reactive antigen, the preabsorbed mixture containing "residual" antibody is then added to the wells of a microtiter plate coated with specific AgI. After a period of incubation sufficient to allow "residual" anti-AgI complement fixing antibodies from the preabsorbed mixture to bind to the immobilized AgI and binding of C1q (e.g. autologous, or exogenous) present in the sample to the complement fixing antibody bound to the immobilized AgI, the plate(s) can optionally be washed to remove unbound antibodies. In certain embodiments, no wash will be performed. A detectably labeled secondary binding molecule is added that binds to the C1q bound to the complement fixing antibodies. The secondary binding molecule is allowed to react with any C1q (e.g. autologous, or exogenous) bound to anti-AgI complement fixing antibodies (e.g., complement fixing antibodies bound to the specific AgI antigens immobilized on the surface), the plate is optionally washed, and the presence of the secondary binding molecule is detected using methods well known in the art.

Thus, in one particular embodiment, the presence of bound anti-AgI complement fixing antibodies and autologous C1q from a biological sample can be readily detected using a secondary binder comprising an antibody directed against the autologous C1q. In another embodiment, the presence of bound anti-AgI complement fixing antibodies from a biological sample can be readily detected using a secondary binder comprising a directly labeled exogenous C1q. A number of anti-human C1q molecules are known in the art (e.g., commercially available goat anti-human C1q, sheep anti-human C1q, etc) which can be readily conjugated to a detectable label to facilitate direct, or indirect detection of autologous of exogenous C1q. Examples of labels which permit direct measurement of immunocomplexes include radiolabels, such as $^3H$ or $^{125}I$, fluorophores, dyes, beads, chemilumninescents, colloidal particles, and the like. Examples of labels which permit indirect measurement of binding include enzymes where the substrate may provide for a colored or fluorescent product. The label may be detected directly (e.g. a radioisotope) or by binding to one or more additional molecules (e.g., an epitope which binds to a labeled antibody). Non-limiting examples of fluorescent compounds which may be used according to the invention include fluorochromes such as Fluorescein (FITC) or Alexa 488, Cy 3, or Cy 5 and green fluorescent protein, as well as phycoerythrin (PE) PE-Cy5, PerCP, ECD, and the like. In some embodiments, the antibody is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In such assays, the concentration of the detectably labeled anti-C1q antibody or the directly labeled C1q will generally be about 0.1 to 500 µ/ml, such as about 150 µ/ml. The solution containing the detectably labeled anti-C1q antibody is generally buffered in the range of about pH 6.5-9.5. The incubation time should be sufficient for the detectably labeled anti-C1q antibody to bind available autologous or exogenous C1q. Generally, from about 0.1 to 3 hours is sufficient, usually 40 minutes sufficing. After non-specifically bound material has been cleared, the signal produced by the bound detectably labeled anti-C1q antibody is detected by conventional means. For example, where the detectable label is a fluorescent compound, the presence of the label can be detected using flow cytometry or other similar techniques, such as the Luminex xMap system. Where an enzyme conjugate is used, an appropriate enzyme substrate is provided so that a detectable product is formed. More specifically, where a peroxidase is the selected enzyme conjugate, a preferred substrate combination is $H_2O_2$ and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490-495 nm is conveniently measured with a spectrophotometer.

Assays can also be conducted in solution, such that the AgI and antibodies present in a biological sample form complexes under precipitating conditions. In one particular embodiment, specific AgI can be immobilized to a solid phase particle (e.g., an agarose bead, latex bead, or the like) using coupling techniques known in the art, such as by direct chemical or indirect coupling. The AgI-coated particle and free cross-reactive antigen (e.g., not immobilized to a solid phase particle) are then contacted under suitable binding conditions with a biological sample suspected of containing anti-AgI complement fixing antibodies. Cross-linking between bound anti-AgI complement fixing antibodies and C1q (e.g., autologous or exogenous) causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above, including use of a detectably labeled anti-C1q antibody.

In a further embodiment, specific AgI can be immobilized to a first solid phase particle (e.g., an agarose bead or the like) and cross-reactive antigen can be immobilized to a second solid phase particle (e.g., a magnetic bead), where the first solid phase particle and the second solid phase particle are different. In such embodiments, the cross-reactive antigen-coated particle and specific AgI-coated particle are then contacted under suitable binding conditions with a biological sample suspected of containing anti-AgI complement fixing antibodies. Particle-cross-reactive antigen-antibody complexes can then be separated from the sample. For example, where the cross-reactive antigens are attached to a first particle, such as magnetic beads, the particle-cross-reactive antigen-antibody complexes can be separated from the solution using any of a number of standard methods. The reaction mixture can then be analyzed to determine the presence or absence of complement fixing antibody-specific AgI antigen complexes using the methods described above.

In yet another embodiment, a method for diagnosing infection (e.g., bacterial or viral) using the present invention involves the use of an assay device for detecting the presence or absence of anti-AgI complement fixing antibodies in a sample by first optionally contacting the sample with cross-reactive antigens to remove any antibodies that could cross-react with the specific AgI, and then contacting the sample with specific AgI to bind any anti-AgI complement fixing antibodies in the sample. In such embodiments, the assay device comprises at least a sample application region, a preabsorption zone, and a detection zone and will be composed of a membrane capable of conducting fluid flow, such as a nitrocellulose membrane strip. Optionally, the membrane may be provided on a rigid or semi-rigid supporting surface, such as a polyethylene strip. In representative embodiments, the preabsorption zone will be interposed between the sample application region and the detection zone. The location of the zones will be such that lateral flow of fluid along the membrane causes all the components of the sample to come into contact with the preabsorption zone first and then come into contact with the detection zone. As such, fluid flow along the membrane from the sample application region towards the preabsorption zone and then the detection zone is facilitated by capillary action across the membrane. Exemplary lateral flow assay devices and detection methods employing the lateral flow assay devices are provided in, for example, U.S. Pat. No. 6,146,589, the disclosure of which is incorporated herein by reference.

In representative embodiments, cross-reactive antigens are immobilized in the preabsorption zone and specific AgI are immobilized in the detection zone. Detection of the presence or absence of anti-AgI complement fixing antibodies is carried out by first adding the sample to the sample application region and allowing the sample to migrate by capillary action across the membrane strip. As the sample migrates across the membrane strip, the sample first comes into contact with the immobilized cross-reactive antigens in the preabsorption zone to provide a preabsorbed sample. The preabsorbed sample then migrates to the detection zone where it comes into contact with immobilized specific AgI. If present, the anti-AgI complement fixing antibodies bind specifically to the immobilized AgI, and the C1q (e.g., autologous or exogenous) then binds specifically to the bound anti-AgI complement fixing antibodies. A detectably labeled anti-C1q antibody can then be contacted with the detection zone to detect the presence of the C1q and anti-AgI complement fixing antibody complex as described above. The detectably labeled anti-C1q antibody molecule is allowed to react with any captured sample C1q, and the presence of the secondary binding molecule detected using methods described above and well known in the art.

In any of the above described embodiments, from one to six washes may be employed, with sufficient volume to thoroughly wash away any non-specifically bound proteins or other molecules present.

Kits

Also provided are kits that find use in practicing the subject methods, as described above. The kits for practicing the subject methods at least include reagents for assaying a sample derived from a human subject for the presence or absence of anti-AgI complement fixing antibodies, where such kits may include: specific AgIs and/or immunoassay devices comprising the specific AgIs, detectably labeled anti-C1q antibodies, directly labeled exogenous C1q, as well as members of a signal producing system, such as enzyme substrates, and the like; various buffers for use in carrying out the subject detection assays; a reference for determining the presence or absence of anti-AgI complement fixing antibodies in a sample; and the like.

In some embodiments, the compositions will be provided in a solution suitable for diluting a biological sample. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

The kits may further include one or more reagents that may be used in preparation of the patient derived sample, such as heparin, Ficoll-Hypaque, lysing buffer, protease inhibitor, and the like, etc. In addition, the subject kits may further include one or more components employed in fractionation of the sample, such as an electrophoretic medium or precursors thereof, e.g. dried precursors of polyacrylamide gels, one or more buffer mediums or components thereof, and the like.

In certain embodiments, the kits further include at least an information storage and presentation medium that contains reference data with which assay results may be compared in order to diagnose infection, e.g., reference data that positively or negatively correlate to the presence of anti-AgI complement fixing antibodies that bind specifically to an antigen of interest derived from a bacterial or viral source, as described above. The information storage and presentation medium may be in any convenient form, such as printed information on a package insert, an electronic file present on an electronic storage medium, e.g. a magnetic disk, CD-ROM, and the like. In yet other embodiments, the kits may include alternative means for obtaining reference data, e.g. a website for obtaining the reference data "on-line."

The kits may further include means for obtaining the patient sample, e.g. a syringe. The subject kits further typically include instructions for carrying out the subject methods, where these instructions may be present on a package insert and/or the packaging of the kit. Finally, the kit may further include one or more reagents from an additional biochemical assay which is used to detect the presence of anti-AgI complement fixing antibodies.

The kit components may be present in separate containers, or one or more of the components may be present in the same container, where the containers may be storage containers and/or containers that are employed during the assay for which the kit is designed.

Devices

Also provided are devices that find use in practicing the subject methods, as described above. Devices for practicing the subject methods at least include reagents for assaying a sample derived from a human subject for presence or absence of anti-AgI complement fixing antibodies, where such devices may include: the specific AgI and optionally cross-reactive antigens, immobilized on the surface of a solid support, such as a microtitre plate or a microbead, such as an agarose or latex bead.

In certain embodiments, a microtiter plate will be provided with a unique AgI immobilized to the surface of each well of the plate. In other embodiments, a microtitre plate will be provided with the same AgI immobilized to the surface of one or more wells of the plate. In certain embodiments, a population of microbeads will be provided with an AgI immobilized to the surface of the population of microbeads. In certain embodiments, a population of microbeads will be provided with a unique AgI immobilized to the surface of each sub-population of microbeads. For example, a population of microbeads will be provided that includes 10 sub-populations, where each sub-population includes a unique immobilized AgI. For example, thirty of the Class I HLA antigens (Table 1 and Table 3) and 30 of the Class II HLA antigens (Table 2 and Table 4) may be immobilized on the surface of microbeads, such as latex beads, in either single antigen form (Tables 1 and 2) or in sub-populations (Table 3 and 4) for use in identifying complement fixing antibodies that bind specifically to one HLA subtype.

TABLE 1

| Bead No. | HLA CLASS I Antigen Typing |
|---|---|
| 1 | A1 |
| 2 | A2 |
| 3 | A3 |
| 4 | A11 |
| 5 | A23 |
| 6 | A24 |
| 7 | A25 |
| 8 | A26 |
| 9 | A29 |
| 10 | A30 |
| 11 | A31 |
| 12 | A32 |
| 13 | A33 |
| 14 | A34 |
| 15 | A36 |
| 16 | A43 |
| 17 | A66 |
| 18 | A68 |
| 19 | A69 |
| 20 | A74 |
| 21 | A80 |
| 22 | B7 |
| 23 | B8 |
| 24 | B13 |
| 25 | B18 |
| 26 | B27 |
| 27 | B35 |
| 28 | B37 |
| 29 | B38 |
| 30 | B39 |
| 31 | B41 |
| 32 | B42 |
| 33 | B44 |
| 34 | B45 |
| 35 | B46 |
| 36 | B47 |
| 37 | B48 |
| 38 | B49 |
| 39 | B50 |
| 40 | B51 |
| 41 | B52 |
| 42 | B53 |
| 43 | B54 |
| 44 | B55 |
| 45 | B56 |
| 46 | B57 |
| 47 | B58 |
| 48 | B59 |
| 49 | B60 |
| 50 | B61 |
| 51 | B62 |
| 52 | B63 |
| 53 | B64 |
| 54 | B65 |
| 55 | B67 |
| 56 | B71 |
| 57 | B72 |
| 58 | B73 |

TABLE 1-continued

| Bead No. | HLA CLASS I Antigen Typing |
|---|---|
| 59 | B75 |
| 60 | B76 |
| 61 | B78 |
| 62 | B81 |
| 63 | B8201 |
| 64 | BW4 |
| 65 | BW6 |

TABLE 2

| Bead No. | HLA CLASS II Antigen Typing |
|---|---|
| 1 | DR1 |
| 2 | DR4 |
| 3 | DR7 |
| 4 | DR8 |
| 5 | DR10 |
| 6 | DR103 |
| 7 | DR11 |
| 8 | DR12 |
| 9 | DR13 |
| 10 | DR14 |
| 11 | DR15 |
| 12 | DR16 |
| 13 | DR17 |
| 14 | DR18 |
| 15 | DR51 |
| 16 | DR52 |
| 17 | DR53 |
| 18 | DR15, 17 |
| 19 | DQ2 |
| 20 | DQ4 |
| 21 | DQ5 |
| 22 | DQ6 |
| 23 | DQ7 |
| 24 | DQ8 |
| 25 | DQ9 |

TABLE 3

| Bead No. | HLA CLASS I Antigen Typing | |
|---|---|---|
| 1 | A11 | B27, 48 |
| 2 | A2, 29 | B39, 56 |
| 3 | A1, 29 | B8, 45 |
| 4 | A2, 24 | B7, 55 |
| 5 | A2, 25 | B18, 64 |
| 6 | A26, 24 | B52, 62 |
| 7 | A31, 68 | B53 |
| 8 | A2, 11 | B13, 62 |
| 9 | A23, 33 | B45, 63 |
| 10 | A23, 34 | B44 |
| 11 | A11, 23 | B49, 52 |
| 12 | A11, 24 | B59, 60 |
| 13 | A24, 33 | B44, 51 |
| 14 | A23, 26 | B41, 72 |
| 15 | A3, 32 | B50, 56 |
| 16 | A2, 24 | B54, 67 |
| 17 | A2 | B52, 73 |
| 18 | A26, 66 | B38, 75 |
| 19 | A11, 33 | B51, 54 |
| 20 | A30 | B13, 72 |
| 21 | A30, 36 | B35, 71 |
| 22 | A69 | B35, 61 |
| 23 | A1, 32 | B60, 64 |
| 24 | A2 | B7, 46 |
| 25 | A30 | B42 |
| 26 | A2 | B8, 58 |
| 27 | A2, 3 | B58, 65 |
| 28 | A1, 36 | B37, 57 |

TABLE 3-continued

| Bead No. | HLA CLASS I Antigen Typing | |
|---|---|---|
| 29 | A3, 68 | B7, 65 |
| 30 | A33, 36 | B53, 61 |

TABLE 4

| Bead No. | HLA CLASS II Antigen Typing | | |
|---|---|---|---|
| 1 | DR15, 9 | 53, 51 | DQ5, 9 |
| 2 | DR4, 15 | 53, 51 | DQ6, 7 |
| 3 | DR16, 4 | 53, 51 | DQ4, 5 |
| 4 | DR8, 14 | 52 | DQ4, 5 |
| 5 | DR4, 7 | 53 | DQ2, 8 |
| 6 | DR15, 18 | 51, 52 | DQ6, 4 |
| 7 | DR11, 12 | 52 | DQ5, 7 |
| 8 | DR103, 17 | 52 | DQ5, 2 |
| 9 | DR1, 13 | 52 | DQ5, 6 |
| 10 | DR9, 10 | 53 | DQ5, 9 |
| 11 | DR15, 12 | 51, 52 | DQ5, 7 |
| 12 | DR16, 14 | 51, 52 | DQ5 |
| 13 | DR13, 8 | 52 | DQ5, 6 |
| 14 | DR11, 13 | 52 | DQ5, 6 |
| 15 | DR17, 7 | 52, 53 | DQ2, 9 |
| 16 | DR15, 8 | 51 | DQ6, 8 |
| 17 | DR15, 4 | 51, 53 | DQ2, 6 |
| 18 | DR15, 17 | 51, 52 | DQ6, 2 |
| 19 | DR15, 7 | 51, 53 | DQ6, 2 |
| 20 | DR1, 7 | 53 | DQ2, 5 |
| 21 | DR15, 11 | 52 | DQ5, 6 |
| 22 | DR7, 13 | 52, 53 | DQ6, 9 |
| 23 | DR15, 13 | 51, 52 | DQ6, 2 |
| 24 | DR9, 14 | 52, 53 | DQ5, 9 |
| 25 | DR8, 9 | 53 | DQ2, 7 |
| 26 | DR17, 14 | 52 | DQ2, 5 |
| 27 | DR1, 11 | 52 | DQ5, 6 |
| 28 | DR17, 4 | 52, 53 | DQ2 |
| 29 | DR11, 4 | 52, 53 | DQ7, 8 |
| 30 | DR1, 14 | 52 | DQ5 |

A number of such devices are known in the art. In one non-limiting example, the device comprises an AgI immobilized to a solid phase particle (e.g., an agarose bead, latex bead, magnetic bead, and the like) using coupling techniques known in the art, such as by direct chemical or indirect coupling. The particle-AgI complex can then be used in the assays described above. In some embodiments, the AgI is immobilized to the solid phase particle by a linking moiety such as, for example, a polypeptide.

Additional items that are required or desired in the methods to be practiced with the devices may be present, which additional items include, but are not limited to: means for obtaining the patient sample, e.g. a syringe; one or more reagents necessary for preparation of the patient derived sample, such as heparin, Ficoll-Hypaque, lysing buffer, protease inhibitor, and the like; instructions for carrying out the subject methods using the subject devices; one or more reagents from an additional biochemical assay which is used to detect the presence or absence of anti-AgI complement fixing antibodies.

In some embodiments, the devices will also be provided with a solution suitable for diluting a biological sample. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

In another non-limiting example, the apparatus will generally employ a continuous flow-path of a suitable filter or membrane, such as a nitrocellulose membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the fluid transport region (e.g., the sample region is in fluid communication with the fluid transport region). The fluid transfer region may optionally have immobilized cross-reactive antigens in order to bind cross-reactive antibodies. After the fluid transport region receives the sample, it is brought into fluid transfer relationship with the measuring region (e.g., the fluid transport region is in fluid communication with the measuring region). The measuring region may have immobilized to it the specific AgI, and detectably labeled anti-C1q antibodies are then combined with the assayed sample and the assay performed as above.

In yet another non-limiting example, the device is a dipstick, to the surface of which is bound in distinct regions: (1) specific AgI and optionally (2) cross-reactive antigens an affinity reagent. In such an exemplary device, the dipstick is inserted directly into a test sample (e.g., blood, serum, or urine) derived from a human subject under conditions suitable to permit binding of anti-AgI complement fixing antibodies to the specific AgI and subsequent binding of C1q (e.g., autologous or exogenous) to the bound anti-AgI complement fixing antibodies. The dipstick is then withdrawn from the sample and, if necessary, washed to remove nonspecifically bound material. The dipstick is next inserted into a container containing a detectably labeled anti-C1q antibody, or fragment or mimetic thereof, which specifically binds human C1q. After incubation for a time sufficient for binding of the anti-C1q antibody to the human C1q and anti-AgI complement fixing antibody-AgI complexes, the dipstick may be washed and binding of the anti-C1q antibody is detected by standard means. Where necessary for detection of the second antibody, the dipstick may be inserted into a second container containing a reagent which activates the detectable label on the second antibody. Alternatively, similar embodiments my use directly labeled exogenous C1q instead of the anti-C1q antibody. In such embodiments, after the dipstick is withdrawn from the sample, the dipstick may be washed and binding of the directly labeled exogenous C1q can be detected by standard methods.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

C1q HLA Antibody Assay

Methods and Materials
The following methods and materials were used in the examples below.

Materials
LABScreen Single antigen and PRA kits were purchased from One Lambda (Canoga Park, Calif.). PE-conjugates of sheep anti-human C1q was purchased from Meridian Life Science, Inc. (Saco, Maine 04072). IVIG (Gamimmune-N); 10% in 0.2 M Glycine; pH 4.4; was provided by Bayer Corporation.

Methods
1. Cytotoxic-Dependent Cytotoxicity (CDC)
    10-S-150 Cytotoxicity Crossmatch—T Cells.
    10-S-151 Cytotoxicity Crossmatch—B Cells.
2. CDC In Vitro Intravenus Gammaglobulin (IVIG) Inhibition
    10-S-150 Cytotoxicity Crossmatch—T Cells.
    10-S-151 Cytotoxicity Crossmatch—B Cells
3. Luminex IgG (Single antigen beads and PRA beads):
    10-S-127 LUMINEX IgG Single Antigen Bead Assay.
4. Luminex C1q (Single antigen beads and PRA beads)

Experimental Procedure
The following procedure was used for the Luminex C1q experimental procedure for the single antigen beads and the PRA beads:
    4.1. Incubate 20 ul sera with 2.5 ul of HLA class I and/or II HLA-Ag coated beads (single antigen/mixed antigen beads) at room temperature for 20 minutes on the tray shaker;
    4.2. Without wash; add 10 ul of PE conjugated anti-human C1q and continue to incubate another 20 minutes on a tray shaker;
    4.3. Wash the beads with 200 ul Luminex wash buffer twice and resuspend in 60 ul PBS.
    4.4. Acquire the sample and collect data on a Luminex machine;
    4.5. Proceed to data analysis using LABScreen software.

Cutoff Setting
A positive HLA-Ab specificity has to meet both of following two criteria:
    a. The score should be >4 based on One Lambda provided formula; and
    b. The raw fluorescence signal of PE should be >100;
5. Sample Preparation for IVIG In Vitro Inhibition Luminex C1q Test
The following three samples were used in the in vitro IVIG inhibition test:
    a. Neat serum (of known anti-HLA specificity);
    b. Serum diluted 1:2 in [10% human albumin, 0.2 M Glycine/PBS] buffer; pH 7.4
    c. Serum diluted 1:2 in 10% IVIG (in 0.2 M glycine buffer as carrier); pH~4.4.
An AB negative unsensitized male serum prepared as above to serve as the IVIG inhibition assay control.
6. Sample Preparation for In Vitro Inhibition CDC Test
Except for 0.2 M Glycine/PBS buffer (pH 7.4) which was used as the diluent, the samples were prepared in the same manner as the above Luminex C1q samples preparation. The above described procedure is the one-Step procedure. The following procedures is multi-step procedure that may also be used:
    a). Two-Step-Wash with and without adding extra human C1q
    b). DTT treat serum prior to performing assay with and without adding extra human C1q.
    c). Use PE-anti-C3 as secondary antibody.
    d). Luminex PRA beads with One-Step procedure.
    e). Heat inactivation of sera with and without C1q addition.

7. Validation Experimental Design

All validation experiments were performed based on "Blinded Test" principle. All formal validation samples were simultaneously tested by AHG-CDC, Luminex IgG, and Luminex C1q assays.

8. Inter-/Intra-Assay QC Sample

The following pre-defined QC samples were used for method QC monitoring:

Positive Control for Inter-Assay QC:
PPS; broadly specific HLA antibody diluted 1:10 in 3% HBSA (kindly provided by Dr. Robert Bray).

Positive Control for Intra-assay QC:
Harbury; neat; with known HLA antibody specificity (in house typing serum).

Negative Control for Inter-assay QC:
A single AB negative male donor with no history of blood transfusion or transplantation.

All QC samples were pre-tested and frozen in small aliquots. Each aliquot was only used for a single batch assay. For Intra-assay QC, 10 replicates of Harbury serum were tested in a same batch assay; PPS and single AB QC sera were tested in each batch of assays for Inter-Assay QC. Three groups of data in three different fluorescence intensity levels (represented as relative numbers) were used for coefficient of variation (CV %) calculation. Each group contained five fluorescence intensity numbers.

9. Sample Resources

A total of 91 blinded samples were used in the Luminex-C1q validation study and compared with the CDC and/or Luminex-IgG results. All validation samples were obtained from the following sources:

1. Predefined HLA typing sera (N=16);
2. Random in house clinical sera (N=42);
3. Random clinical sera from Wisconsin (N=11); and
4. Random male AB sera (N=22).

The IVIG in vitro inhibition test was performed on 30 samples (in vitro samples), eleven Pre-IVIG and Post-IVIG sera (in vivo) were also collected and tested by the CDC, LMX-C1Q and LMX-IgG method.

Results

Formation of (Ab-Ag) complex and fixation of complement C1q are the early events of the classical pathway cascade and CDC. The amount of C1q fixation directly correlates with cell death, the terminal step of the classic pathway cascade and CDC. Instead of visually estimating the percent cell death under a microscope, Luminex-C1q was designed to detect C1q fixation by HLA-(Ab-Ag) complexes using a high throughput Luminex technology.

In the reaction, Luminex beads individually coated with single HLA antigens were incubated with serum to allow HLA-Ab (if any) to bind to the corresponding Ag beads and fix complement C1q from the serum, followed by adding fluorescently labeled anti-human C1q (PE-antiC1q). After an additional incubation, the beads were washed and the PE-fluorescence intensity on the each bead surface was measured by a Luminex machine.

The PE intensity on each HLA single antigen bead represents the complement fixation capability of the corresponding HLA (Ab-Ag) complex; which proportionately correlates with the CDC effect.

Luminex-C1q Methodology Design and Optimization

Two-Step Versus One-Step Procedure

One-Step and Two-Step procedures with/without adding extra human C1q were evaluated. The data showed that the One-Step procedure is much better than the Two-Step procedure with respect to the background noise, detection sensitivity, and method simplicity (FIG. 7).

Sample Diluent Effects

Five different diluents were evaluated in the One-Step Luminex-C1q:
a. 3% HBSA;
b. 0.2 M Glycine buffer; pH 4.4;
c. 0.2 M Glycine in PBS; pH 7.2;
d. 10% human albumin in Glycine buffer; pH 4.4; and
e. 10% human albumin in 0.2 M Glycine buffer/PBS; pH 7.2.

It is interesting to note that when the serum was diluted 1:2 in each of the above diluents, only the diluents with glycine dramatically increased the C1q fixing in pre-defined positive sera (2-8 fold increase compared with neat sera results) in the Luminex-C1q assay. The increase of C1q fixation by glycine buffer could result from (a) direct enhancement of C1q fixing and/or (b) indirectly enhancing CFAb binding, thereby increasing C1q fixing. The effect of glycine, 3% HBSA, and PBS on IgG binding was also evaluated in the Luminex-IgG assay. Instead of increasing IgG binding, all diluents proportionately decreased IgG binding. Therefore, glycine buffer directly enhances C1q fixation through an unknown mechanism.

Based on the results and consideration of both detection sensitivity and method stability, 10% human albumin in 0.2 M Glycine buffer/PBS (pH 7.2) was finally chosen as the best diluent to be used for Luminex-C1q IVIG inhibition assay.

C3 Fixation

Complement C3 fixation to HLA-Abs (Ab-Ag) complexes was also evaluated using PE-conjugated anti-human C3 Abs in both the one-step and two-step procedures. C3 fixation was not detectable in the assay. It is possible that the PE-anti-C3 was not optimized or that the antibody itself had insufficient avidity. If necessary, more C3 antibodies could be tested.

Correlation between CDC and Luminex-C1q

A total of 78 sera were tested by both CDC and Luminex-C1q and the results obtained highly correlated with each other (N=76, 97%; see attached "LMX-C1q Validation Sample-Regular Samples (FIG. 16A-N) and LMX-C1q Validation-IVIG Samples (FIG. 17A-J)"). Using the LMX-IgG to determine all binding Abs present in the serum, there were 22 sera in which LMX-C1Q identified the CF Abs better than the CDC (N=22; 28%). In all tested samples, the HLA, IgG specificities picked up by CDC were also positive by Luminex-C1q. The Luminex-C1q assay often picks up a limited set of additional CF HLA-Ab specificities not seen by CDC. All of the "extra" specificities detected by Luminex-C1q were also detected in the Luminex IgG assay confirming the higher sensitivity of the LMX-C1Q assay. In cases of sera with broad HLA-Ab specificity, the CDC could not call any specificities; however, Luminex-C1q was able to clearly identify the specificities (#2, #21, #36, #37, #40, #42, #64; N=7; 9%).

Another 5 sera (#6, #9, #18, #67, #70; 6.4%) were called "Unclear or undefined HLA-Abs specificity by CDC, but clear specificities were called by Luminex-C1q and Luminex-IgG. Misidentified specificities were called by CDC in samples #7, #10, #11, #27, and #28 (N=5; 6.4%) which were not found in either of the Luminex assays (C1q or IgG).

Four sera (samples #2, #3, #7, and #10; N=4; 5.1%) identified some specificities in CDC which were negative in the Luminex-C1q. Blinded samples were then retested by CDC and were negative on repeat confirming the wrong calls by CDC. There was one Rituxan treated patient serum in which Luminex-C1q was still able to identify both class I and II specificities but no specificities could be determined by CDC because all B cells were killed by the cytotoxic Rituxan in the serum.

It was noticed that any IgM specificities (#38, #41, #64, #67, and #76 in FIG. 16A-N and #7 in FIG. 17A-J) detected in DTT treated serum tested by CDC also had corresponding IgG detected in Luminex-IgG (only #38, #41, #64, and #67 were picked up by Luminex-C1q). This suggests that the coexistence of both IgM and IgG alloantibodies to the same Ag specificities might be a common phenomenon in vivo.

IgM specificities detected by CDC were negative in the Luminex-C1q assay (#76 in FIG. 16A-N and #7 FIG. 17A-J). [Subsequent work has confirmed this observation]. C1q might not be able to bind to the IgM (Ab-Ag) complex, or the anti-C1q antibody might be unable to access C1q in the complex because of steric hindrance.

Another two apparently uncorrelated samples (N=2; 2.6%) were found in the validation. Sample #13 had A23, B57, and B58 Ab detectable by both CDC and Luminex-IgG but not by Luminex-C1q; sample #24 had B54, 55, 56, 61, 81 detectable by CDC and LMX-IgG but not by Luminex-C1q. (Note B61=wrong call by CDC). These two questionable samples were repeated by "spiking" with exogenous human C1Q and complete concordance was observed. Taken altogether, 27% (N=21) of samples tested by CDC were called broad or wrong and/or had undefined specificities. All had clear specificities by Luminex-C1q.

While Luminex-C1q detects additional specificities (also observed in the LMX-IgG) compared with CDC, its inclusion correlation (LMX-C1q includes all specificities detected by CDC) was 100% (78/78).

Correlation between Luminex-IgG and Luminex-C1q

The results from the validated samples showed that all HLA-Ab specificities called by Luminex-C1q were also found by Luminex-IgG. In all the samples we tested, Luminex-IgG always defined more specificities than were detected by CDC and/or Luminex-C1q. This is due to the lack of detection of non-CF Abs and of IgM, which are not detectable by CDC and LMX-C1Q, respectively. It is likely that Luminex-IgG picks up non-CFAbs in samples #1, #5, #29, #30, #38, #65, #71, and #77 (N=8; 10%). LMX-IgG also detected specificities in normal unsensitized AB negative male donor sera (#27, #28, and #88), which should theoretically be negative in the assay.

CDC and Luminex-C1q are based on the same principle, namely detection of complement fixing antibodies, long appreciated to be clinically relevant in the immune response. However, Luminex-IgG is based on the principle of IgG-binding only without regard to the downstream effects of that binding. Therefore, comparisons of method sensitivity, while informative, are not a basis for test validation because the tests differ in principle. The standard to make a judgment for a better assay system is still to clearly identify those clinically relevant alloantibodies which provide reliable information for the best donor-recipient matching, prediction of acute rejection and post transplant monitoring. Since CDC has been well proven in its clinical significance, we mainly focused on the comparison with CDC in our Luminex-C1q validation study; and Luminex-IgG was used to be a reference to further confirm the results.

In vitro IVIG Inhibition Testing and In Vivo IVIG Treated Patient Testing

Figure 8:
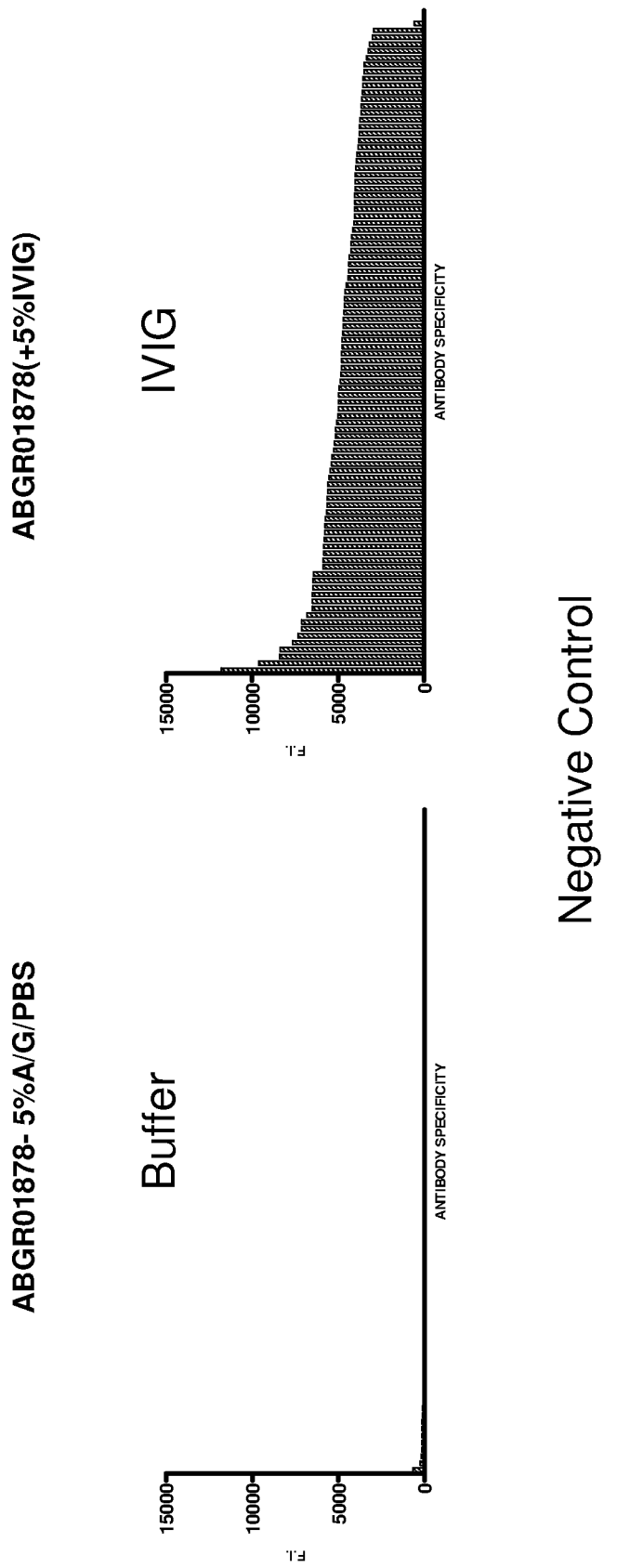
FIG. 8 shows the results of intravenous gammagobulin (IVIG) spiking using the usual LMX-IgG assay does not work. Figure represents testing the negative control serum diluted in buffer vs diluted in IVIG as would be done for the IVIG in vitro inhibition assay and using an anti-IgG labeled second step (the current commercial assay).
Figure 9:
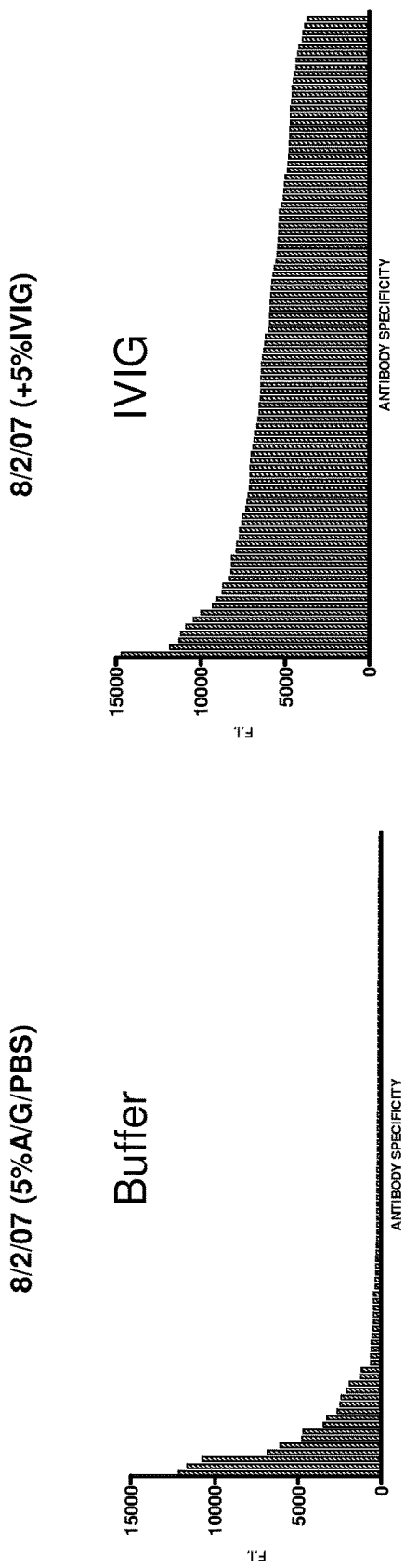
FIG. 9 is the same as FIG. 8 except a patient serum is spiked. Results show that it would be impossible to detect inhibition of the patient antibody (visible in the sample diluted in buffer) if IVIG were added to the serum and detected with an anti-IgG.
Figure 11:
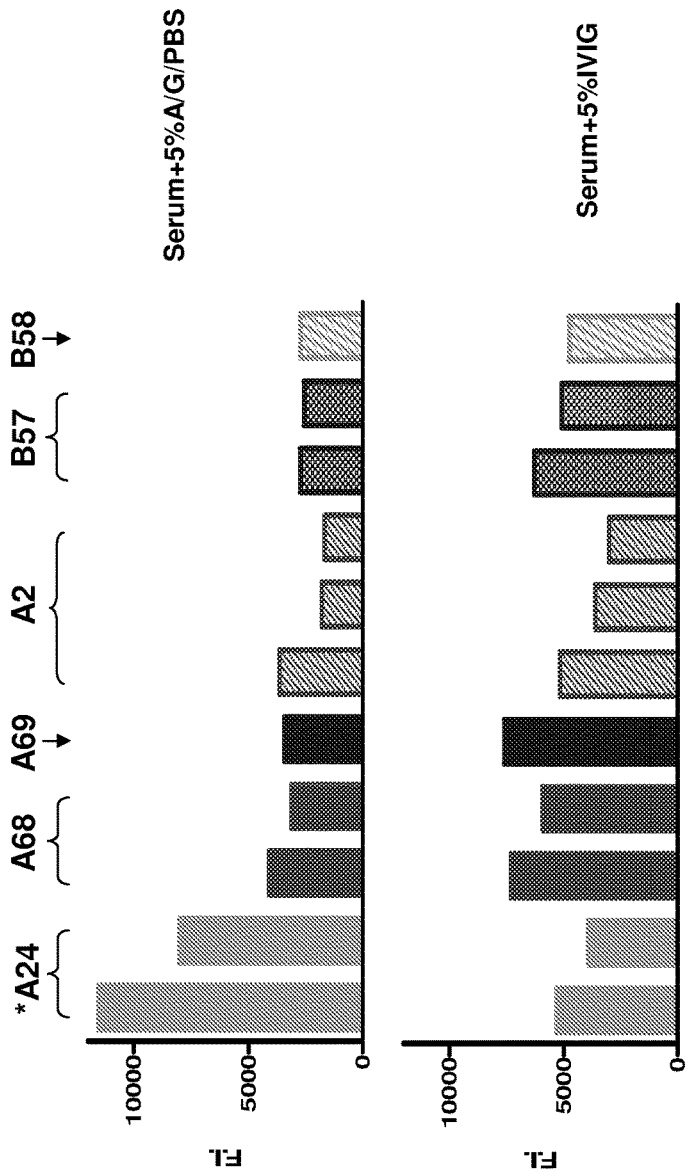
FIG. 11 shows actual IVIG in vitro inhibition C1q assay on Adult Heart patient serum suggesting that only the A24 would be able to be inhibited by IVIG if the patient were treated.
Figure 12A:
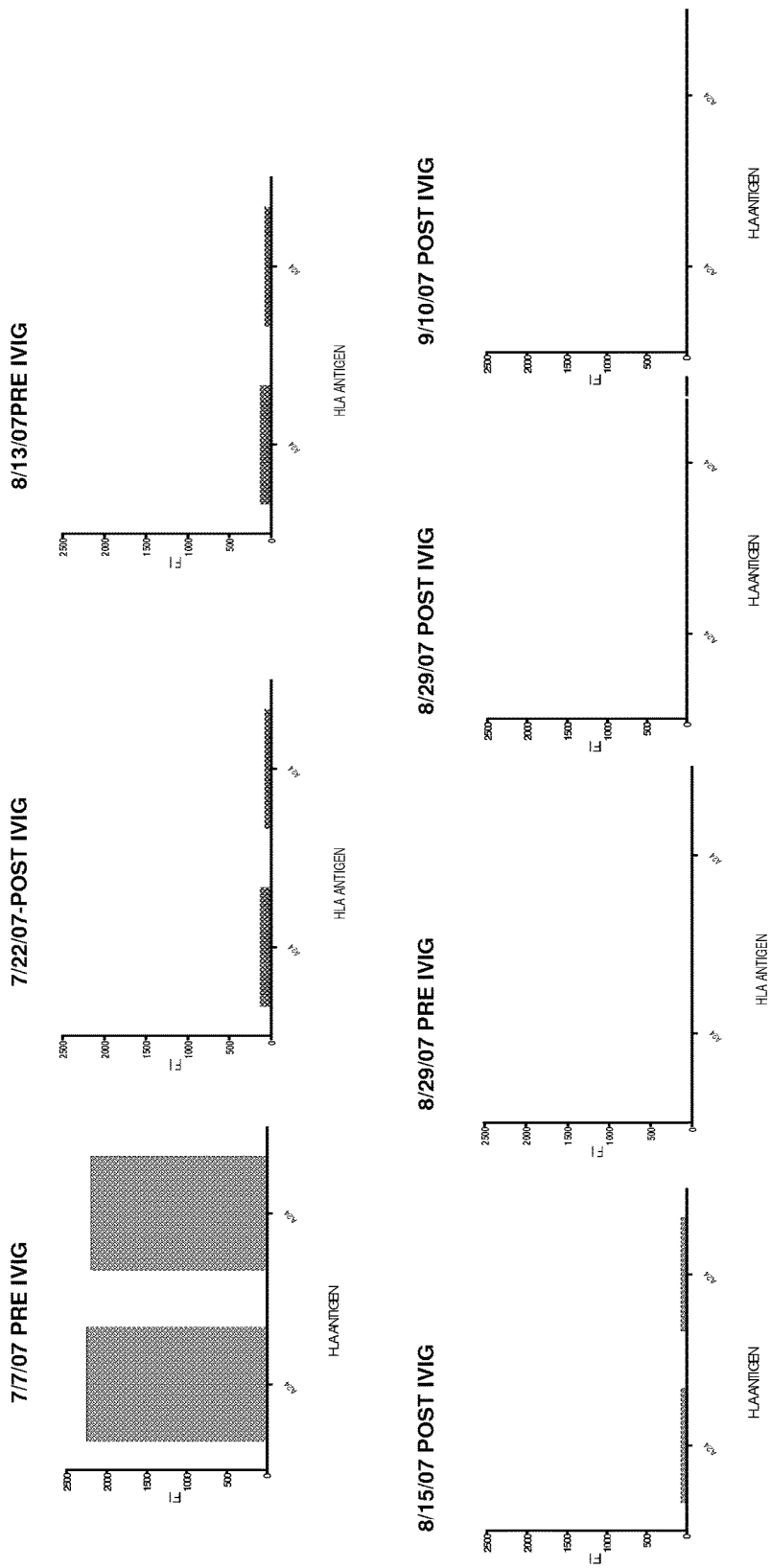
Figure 13A:
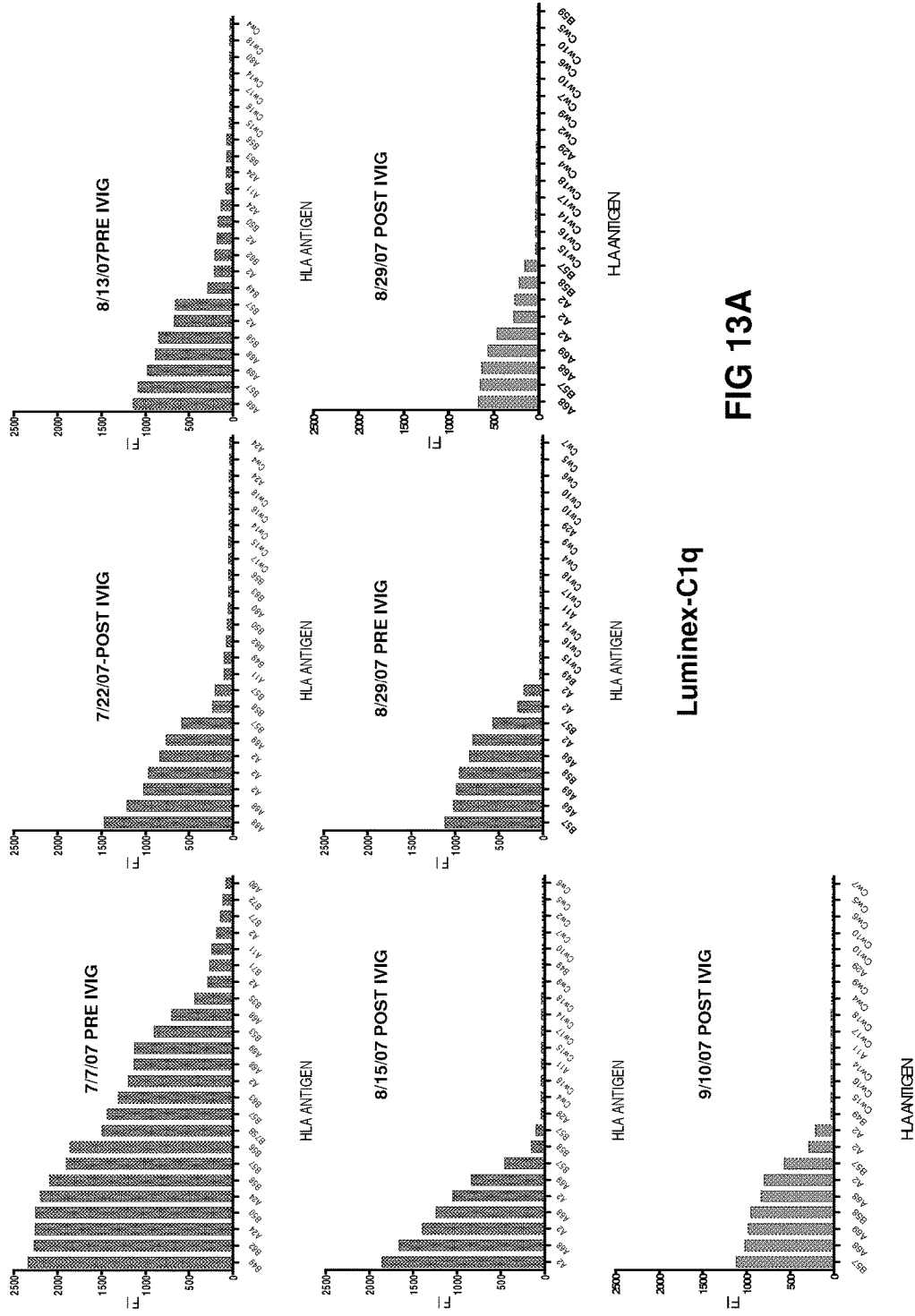
FIGS. 13A-13B show the monitoring of all of the patient's antibodies with subsequent treatments of IVIG the LMX-C1q (FIG. 12A) and LMX-IgG (FIG. 12B) assays. Note the difficulty in seeing the suppression/disappearance of antibodies using the LMX-IgG assay.
Figure 13B:
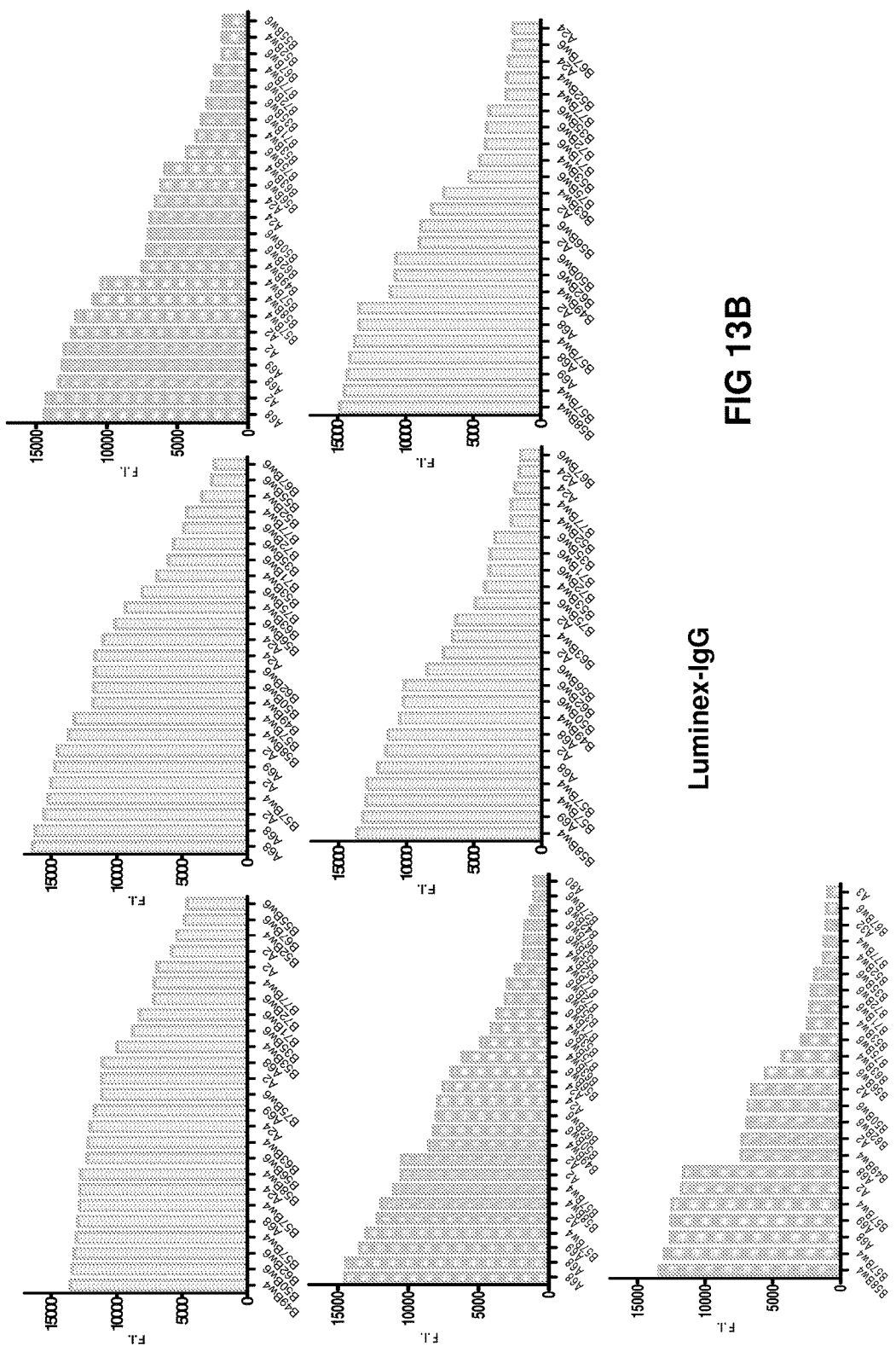
Figure 14:
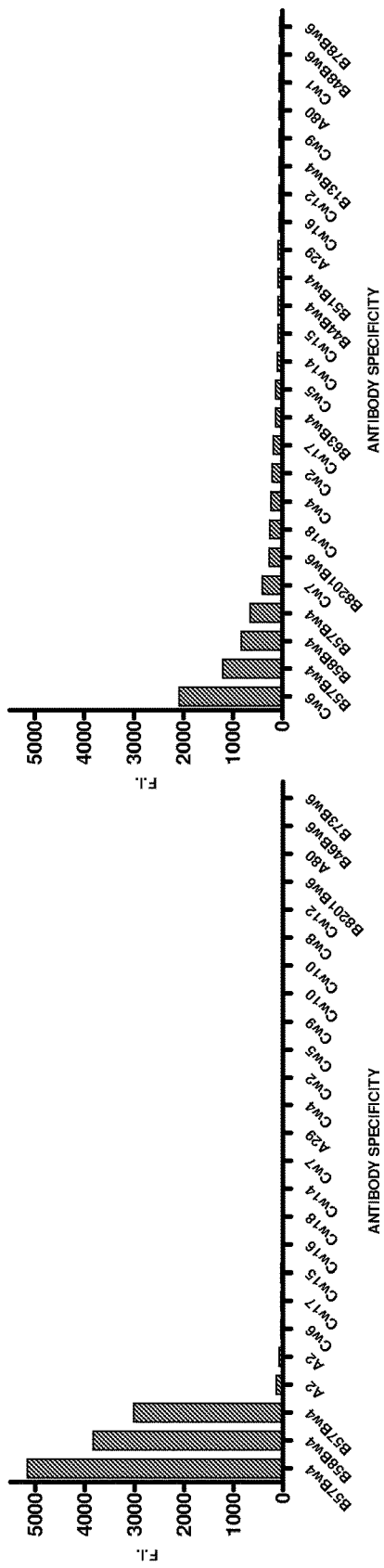
FIG. 14 shows results of an in vitro IVIG inhibition C1q assay, similar to FIG. 11, but results are for a Pediatric Kidney patient suggesting that the B57, B58 antibodies would be effectively suppressed by IVIG.
Figure 15:
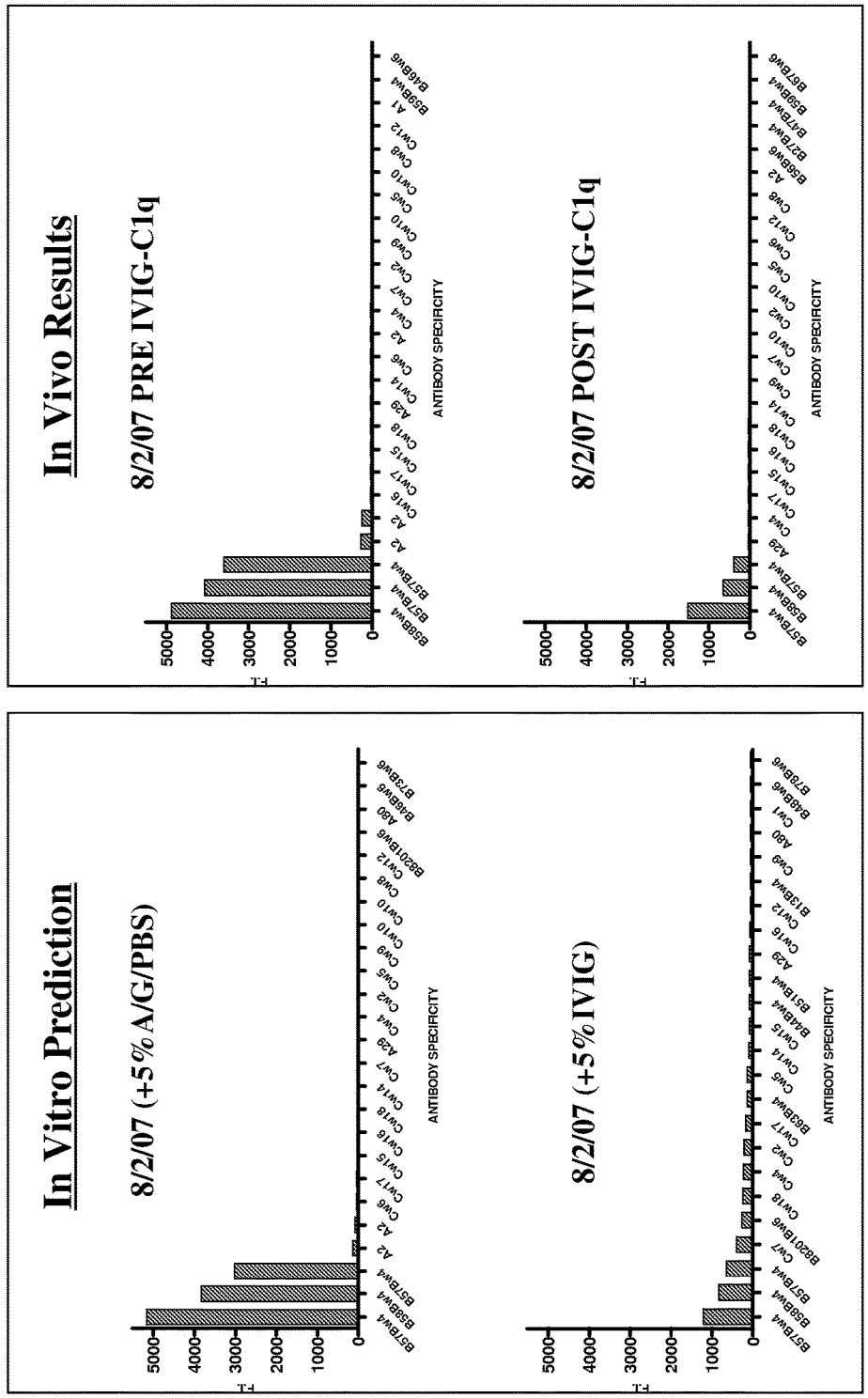
FIG. 15 shows a side by side comparison of in vitro and in vivo results. Left panel (same as FIG. 14) shows in vitro IVIG inhibition and right panel shows before and after IVIG infusion in the patient for the same serum date.

A total of 11 patient serum samples have been used in the IVIG inhibition study. Parallel experiments of Luminex-C1q, CDC and/or Luminex-IgG were performed simultaneously. The IVIG inhibition test was performed by CDC and Luminex-C1q but not Luminex-IgG, since the latter is not an appropriate assay for this purpose (see IVIG spiking results; FIGS. 8-9).

All results of the Luminex-C1q in vitro IVIG inhibition test perfectly matched the in vivo IVIG effects seen in the post-IVIG samples; even in those samples in which IVIG caused a differential inhibition of certain specificities and not of others (FIG. 10). Follow up samples of pre and post-IVIG sera were tested by Luminex-C1q in one patient who was treated multiple times with IVIG. The in vitro IVIG inhibition test exhibited a differential inhibition pattern: A24 was inhibited and A2, 68, 69 were not inhibited. After the patient received the IVIG treatments, follow-up post-IVIG samples were taken for Luminex-C1q assay and confirmed the same inhibition pattern (FIGS. 11-13B). In most cases, Luminex-C1q IVIG inhibition results also correlated with, or were better than, the results of the CDC IVIG inhibition test.

The validation data obtained from the IVIG study group clearly demonstrated the advantages of Luminex-C1q compared with CDC and Luminex-IgG (FIG. 16A-N and FIG. 17A-J).

Discussion

The correct identification of clinically relevant/detrimental HLA alloantibodies existing in the serum of a (potential) graft recipient is a critical step prior to transplantation. It is generally well accepted in the transplantation field that cytotoxic alloantibody (CFAbs) can cause a hyperacute rejection.

There are two major categories of HLA antibody (HLA-Ab) which could exist in a recipient serum based on their complement fixing characteristics, e.g., CFAbs and non-CFAbs. Only CFAbs are known to be detrimental and clinically relevant but the real immunological function of non-CFAbs is not clear. Flow crossmatch studies suggest that some binding antibodies are irrelevant and some detrimental. No distinction in the flow has heretofore been made with respect to the ability to bind complement. Some non-CF Abs may, in fact, be beneficial antibodies and play an important role in maintaining normal immune homeostasis. Our unpublished IVIG study data suggest that some IgGs naturally exist in normal human sera that can specifically bind to HLA-Ags. Instead of activating the CDC cascade to kill the cells, they exert a protective effect and inhibit CDC effects resulting from cytotoxic HLA alloantibodies. The mechanism is still under investigation. It is very important to differentiate the two types of antibodies in transplant practice.

Complement C1q is a key component of the classical complement pathway and acts as the first recognition molecule that interacts with antibody-antigen complexes to activate the complement cascade. The binding of C1 to antibody is via C1q and C1q must cross link at least two antibody molecules before it is firmly fixed. Complement 1 (C1) complex comprising three distinct proteins C1q, C1r, and C1s is the key initial activation step of the classical pathway of complement and plays an important role in the initiation of the inflammatory process. Complement C1q is a very stable protein molecule with a high serum concentration (150 ug/ml). In our study, the oldest serum tested was frozen in 1976 and it still had good C1q binding activity. Theoretically, the detection of C1q fixation by HLA alloantibodies is superior to the use of other later downstream complement elements in the classical pathway cascade. The method allows one to know that the screen donor can fix complement to particular antibody-antigen complexes, giving an estimation of risk for activating the sequential steps of the cascade post-transplant. Our presented Luminex-C1q method development and validation data have provided strong evidence for the rationale of this assay design.

During the Luminex-C1q methodology development and optimization, several different experimental designs for the procedure were evaluated including One-Step, Two-Step (with and without adding additional human C1q), DTT serum treatment, and different diluents. Based on method sensitivity, stability, accuracy, and simplicity, a final optimized One-Step procedure was determined and used in the validation study. For the Luminex C1q in vitro IVIG inhibition assay, 10% human albumin in 0.2 M Glycine/PBS buffer (pH: 7.4) was used as a sample diluent control to control for dilution effect.

This newly developed Luminex-C1q perfectly combines the features from both CDC and Luminex-IgG and, at the same time, eliminates the main drawbacks that exist in those two assays. On the one hand, unlike LMX-IgG but like CDC, it directly detects CFAbs to give a functional test result superior to CDC through a cell-free, solid phase binding system. Since it additionally has high sensitivity, Luminex-C1q is able to pick up low level cytotoxic antibodies missed by CDC. On the other hand, like LMX-IgG but unlike CDC, Luminex-C1q can easily simultaneously identify up to nearly a 100 different HLA-Abs in a single reaction due to the use of the Luminex high throughput multiplex detection system.

LMX-C1q actually can exclude false positive results from non-cytotoxic Abs that are often called by Luminx-IgG. Since the Luminex-C1q assay detects only CFAbs and has no interference from IVIG (i.e., non CF IgG existing in the serum from an IVIG treated patient), the LMX-C1q can be reliably used for the in vitro IVIG inhibition test. The Luminex-C1q assay has proved its reliability in the prediction and monitoring of IVIG in vivo effectiveness. (FIG. 17A-J and FIGS. 10-15). By analyzing and comparing the results of all three methods, the following patterns were found and are consistent with the theoretical principles of each test system:

1. Any specificity (except one due to IgM) called by CDC is included in Luminex-C1q; if not, then CDC was incorrectly interpreted and/or due to non-HLA antibodies;
2. Any specificity called by Luminex-C1q will also be included in the specificities detected by Luminex-IgG, but not necessarily by CDC; and
3. If Luminex-IgG is negative, then Luminex-C1q will be negative and the DTT treated sera in CDC will also be negative.

Example 2

Directly-Labeled C1q HLA Assay

The following provides an exemplary method of screening human serum to identify HLA complement fixing antibodies (HLA-CFAb) using the Luminex multiplex/single antigen bead technology. However, these methods may be carried out using any flow cytometry or ELISA system to identify any kind of complement fixing antibodies with any multiplex or single antigen system.

Sera to be tested were incubated with HLA single antigen coated Luminex (LMX) beads, such as the LABscreen Class I and LABscreen Class II single antigen bead mix (One Lambda, Canoga Park, Calif.) and biotin labeled C1q. Serum A was known to have complement fixing ability by both complement dependent cytotoxicity (CDC) and by the indirect C1q (anti-C1q) assay. It has a limited set of HLA antibody specificities. Serum B was a positive control serum known to have complement fixing ability by both CDC and the indirect C1q (anti-C1q) assay. It has a very broad set of HLA antibody specificities. The negative control was a non-transfused male AB negative (ABO/Rh blood group type) serum that was known not to fix complement in any assay. All sera were heat inactivated to "decomplement" them prior to testing.

Figure 18:
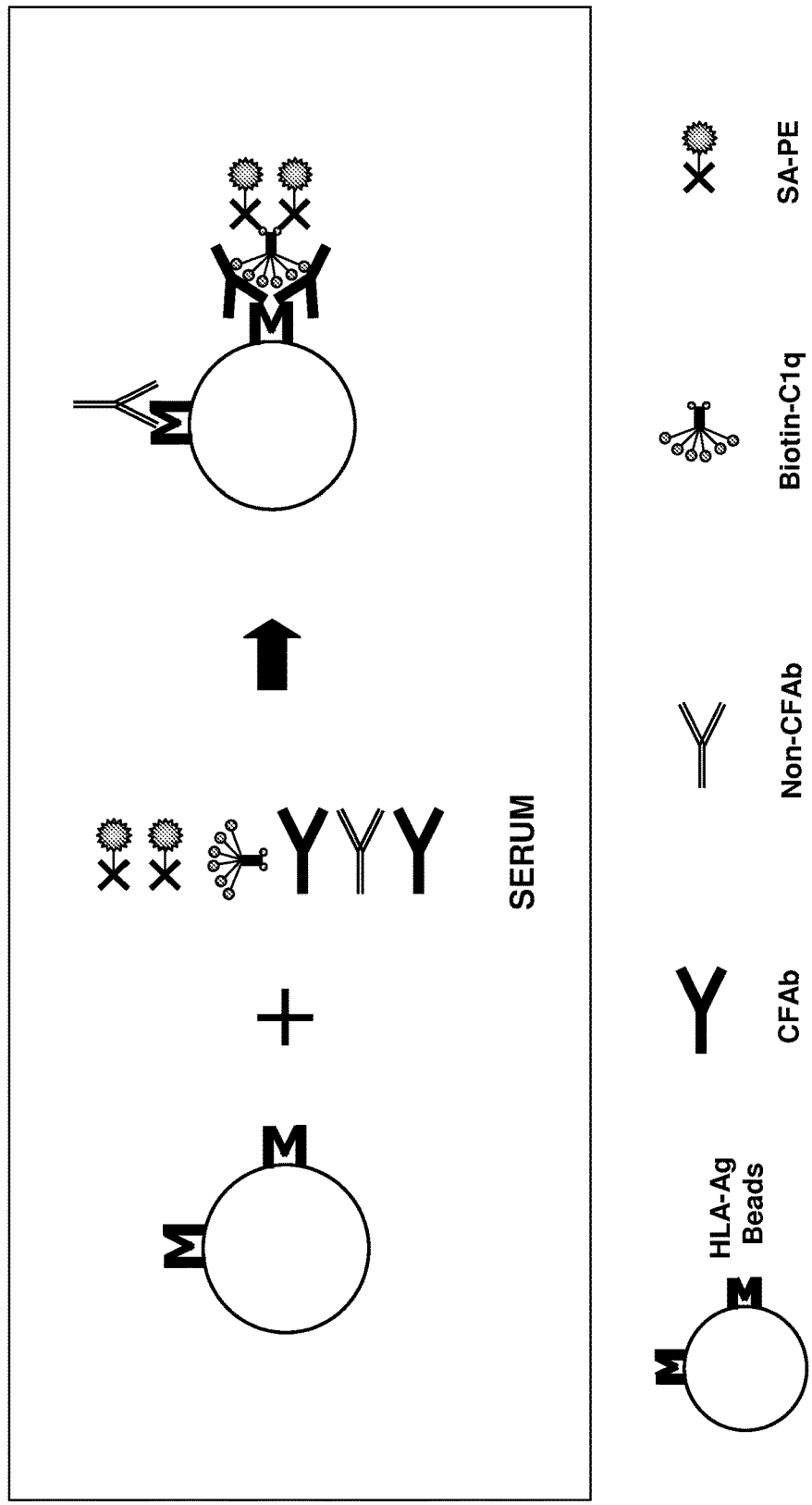
FIG. 18 provides a general schematic of a directly labeled C1q assay.

As exemplified in FIG. 18, HLA antibodies in the test serum (1) bind to the HLA antigens on the corresponding beads and (2) the bound HLA-CFAb fixed biotin labeled C1q (Bio-C1q) to (3) form a complex of HLA-CFAb/Ag/Bio-hC1q. R-Phycoerythrin-conjugated streptavidin (SA-PE) present in the reaction then bound to the Bio-hC1q of the complex. After washes with LAB screen wash buffer, the beads were acquired on a Luminex machine. The PE intensity on each HLA single antigen bead represented the complement fixation capability of the corresponding HLA-Ab/Ag complex, which proportionately correlated with the complement dependent cytotoxicity (CDC) effect of the antibodies.

The reaction pattern of the test serum was then compared to the antigen array worksheet associated with the antigen bead mix used in the assay, and the accompanying analysis program provided data for calculating panel reactive antibody (CPRA) and defining anti-HLA complement fixing antibody specificity.

Figure 19B:
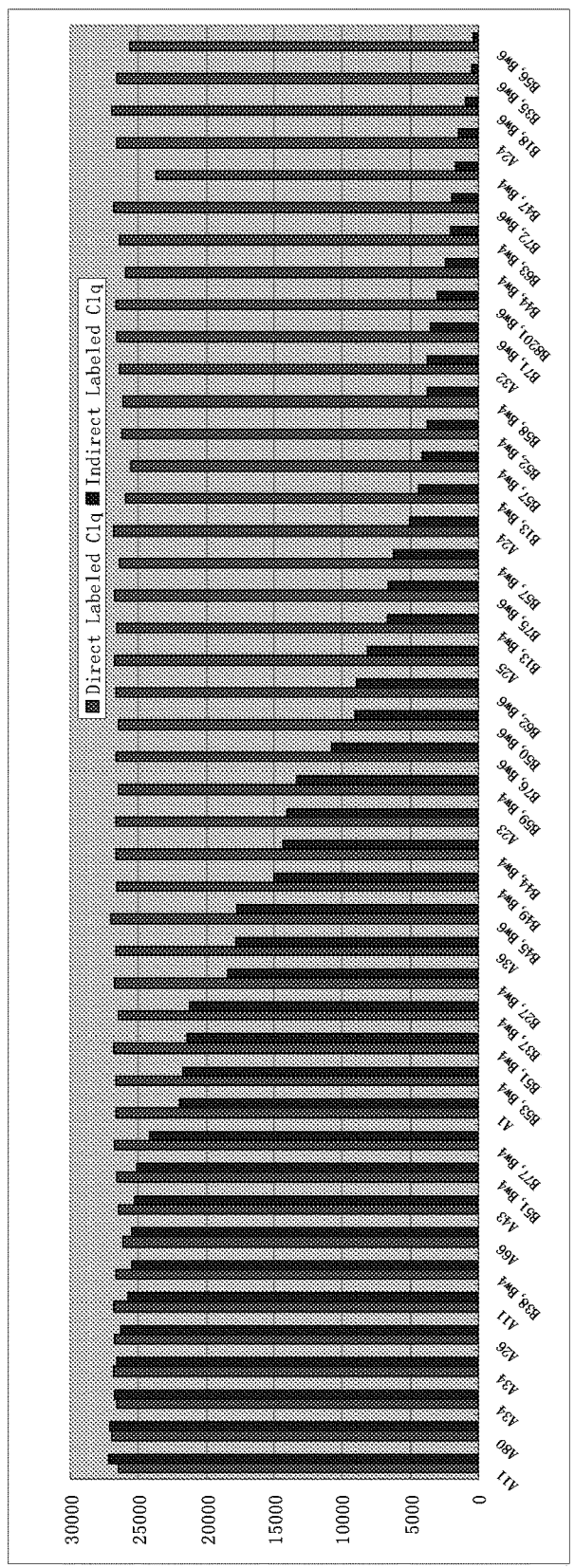

The specificity of HLA detection using the directly-labeled C1q in the LMX-C1q assay was compared to the specificity of carrying out the LMX-C1q assay using the indirectly-labeled C1q (anti-C1q antibody) as described in the earlier examples. As shown in FIG. 19A, detection with the directly-labeled C1q resulted in an increased number of true positives. FIG. 19B displays a subset of Serum B which included only the positive antibodies detected by the directly-labeled C1q and this subset is arranged by strength of indirectly labeled C1q reactions. The X axis in each case represents the specificities of the single antigen beads (i.e., each bar is a unique single antigen different than all other bars) The Y axis represents the MFI (mean fluorescence intensity) and is an indication of strength of the reaction.

The in vitro IVIG inhibition assay was also carried out with this method to demonstrate the correlation and reproducibility of carrying out the assay with anti-C1q antibody (FIG. 20A) and directly-labeled C1q (FIG. 20B). The IVIG assay was carried out as described above. As shown in FIG. 20B, directly-labeled C1q was similarly effective as the anti-C1q antibody in the IVIG inhibition assay. However, the assays carried out with directly-labeled C1q were more sensitive than the assays carried out with the anti-C1q method.

The above results successfully demonstrated that this newly developed assay is a simple, reliable, sensitive, objective, specific, high throughput multiplex HLA alloantibody test. It will be a replacement for the classic CDC assay. The principle of this assay could be a universal technique platform to be used for any cytotoxic antibody detection.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and That which is claimed is:

1. A method for determining the presence or absence of complement fixing antibodies in a biological sample from a subject that bind specifically to human leukocyte antigens (HLAs), the method comprising:
   incubating a biological sample from a subject with a collection of microparticles of different subtypes and exogenous complement factor C1q, wherein each microparticle is coated with a different purified HLA subtype and wherein the incubating is for a sufficient time to allow anti-HLA complement fixing antibodies in the biological sample to bind to the HLAs and to allow the exogenous complement factor C1q to bind the anti-HLA complement fixing antibodies in the biological sample;
   prior to performing any washing step, incubating the microparticles with at least one detectably labeled ligand that specifically binds directly to the exogenous complement factor C1q bound to the anti-HLA complement fixing antibodies bound to the HLAs; and
   detecting the presence or absence of the detectably labeled ligand bound to the exogenous complement factor C1q to determine the presence or absence of complement fixing antibodies.

2. The method of claim 1, wherein the microparticle is an agarose bead.

3. The method of claim 1, wherein the microparticle is a latex bead.

4. The method of claim 1, wherein the microparticle is a magnetic bead.

5. The method of claim 1, wherein the biological sample is blood, or blood products.

6. The method of claim 1, wherein the detectably labeled ligand is a detectably labeled antibody or binding fragment thereof.

7. The method of claim 1, wherein the detectable label is a fluorochrome, a chromophore, an enzyme, a linker molecule, a biotin molecule, an electron donor, an electron acceptor, a dye, a metal, or a radionuclide.

8. The method of claim 1, wherein the detecting is by flow cytometry.

9. A method for determining the presence or absence of complement fixing antibodies in a biological sample from a subject that bind specifically to human leukocyte antigens (HLAs), the method comprising:
   incubating a biological sample from a subject with a collection of microparticles of different subtypes and labeled exogenous complement factor C1q, wherein each microparticle is coated with a different purified HLA subtype and wherein the incubating is for a sufficient time to allow anti-HLA complement fixing antibodies in the biological sample to bind to the HLAs and to allow the labeled exogenous complement factor C1q to bind the anti-HLA complement fixing antibodies in the biological sample; and
   detecting the presence or absence of the labeled exogenous complement factor C1q bound to the anti-HLA complement fixing antibodies by, prior to performing any washing step, binding of an additional molecule to the labeled exogenous C1q to determine the presence or absence of complement fixing antibodies in the biological sample that bind specifically to HLAs.

10. The method of claim 9, wherein the microparticle is an agarose bead.

11. The method of claim 9, wherein the microparticle is a latex bead.

12. The method of claim 9, wherein the microparticle is a magnetic bead.

13. The method of claim 9, wherein the biological sample is blood, or blood products.

14. The method of claim 9, wherein the exogenous C1q is biotin-C1q (Bio-C1q).

15. The method of claim 9, wherein the detecting is by flow cytometry.

16. The method of claim 14, wherein the binding of an additional molecule comprises binding an R-Phycoerythrin-conjugated streptavidin to the biotin-C1q.

17. The method of claim 1, wherein the biological sample from a subject and the collection of microparticles are incubated at room temperature.

18. The method of claim 9, wherein the biological sample from a subject and the collection of microparticles are incubated at room temperature.

* * * * *